United States Patent
Leinonen et al.

(10) Patent No.: US 10,501,730 B2
(45) Date of Patent: *Dec. 10, 2019

(54) MANNANASE VARIANTS

(71) Applicant: AB Enzymes Oy, Rajamäki (FI)

(72) Inventors: Taija Leinonen, Riihimäki (FI); Leena Valtakari, Rajamäki (FI); Michael Seefried, Großostheim (DE); Kari Juntunen, Espoo (FI); Terhi Puranen, Nurmijärvi (FI)

(73) Assignee: AB ENZYMES OY, Rajamaki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/608,179

(22) Filed: May 30, 2017

(65) Prior Publication Data

US 2018/0346898 A1    Dec. 6, 2018

(51) Int. Cl.

| | |
|---|---|
| *C12N 9/24* | (2006.01) |
| *C12P 19/02* | (2006.01) |
| *C09K 8/03* | (2006.01) |
| *C09K 8/035* | (2006.01) |
| *A23K 20/189* | (2016.01) |
| *A23L 2/84* | (2006.01) |
| *C11D 3/386* | (2006.01) |
| *C09K 8/62* | (2006.01) |
| *A23K 20/147* | (2016.01) |
| *A23C 11/10* | (2006.01) |
| *C09K 8/68* | (2006.01) |
| *C09K 8/86* | (2006.01) |

(52) U.S. Cl.
CPC .......... *C12N 9/2494* (2013.01); *A23C 11/106* (2013.01); *A23K 20/147* (2016.05); *A23K 20/189* (2016.05); *A23L 2/84* (2013.01); *C09K 8/035* (2013.01); *C09K 8/62* (2013.01); *C09K 8/68* (2013.01); *C09K 8/86* (2013.01); *C11D 3/38636* (2013.01); *C12P 19/02* (2013.01); *C12Y 302/01078* (2013.01); *C09K 2208/24* (2013.01)

(58) Field of Classification Search
None
See application file for complete search history.

(56) References Cited

U.S. PATENT DOCUMENTS

| | | | |
|---|---|---|---|
| 8,844,629 B2 | 9/2014 | Armstrong | |
| 2004/0223961 A1* | 11/2004 | Anderson | ............ A61K 38/465 424/94.61 |
| 2008/0064064 A1 | 3/2008 | Kensch et al. | |

FOREIGN PATENT DOCUMENTS

| | | |
|---|---|---|
| WO | 2014/088940 A1 | 6/2014 |
| WO | 2017/079756 A1 | 5/2017 |
| WO | WO-2018206302 A1 * | 11/2018 ............... C12N 9/24 |

OTHER PUBLICATIONS

Indian Patent Application 201741016141, filed May 8, 2017.*
Dhawan et al., Microbial Mannanases: An Overview of Production and Applications, Critical Rev. Biotechnol., 2007 27, 197-216.*
Uniprot, Accession No. W4QLJ5, May 10, 2017, www.uniprot.org.*
Wahl et al., Molecular Hybridization of Immobilized Nucleic Acids: Theoretical Concepts and Practical Considerations, Methods Enz ., 1987, 152, 399-407.*
"Database UniProt", XP-002773470, Retrieved by EBI, Mar. 19, 2014, 1 page.
Extended European Search Report received for European Patent Application No. EP17173416.3, dated Sep. 20, 2017, 7 pages.

* cited by examiner

*Primary Examiner* — Robert B Mondesi
*Assistant Examiner* — Todd M Epstein
(74) *Attorney, Agent, or Firm* — Ziegler IP Law Group, LLC

(57) ABSTRACT

Variants of mannanase, compositions including the variants, to methods for their production and to methods of using the variants to degrade and modify mannan containing material.

20 Claims, 8 Drawing Sheets
Specification includes a Sequence Listing.

MANNANASE VARIANTS

FIELD OF THE INVENTION

This invention relates to variants of mannanase enzyme. The variants are useful in industrial applications wherein degradation or modification of mannan is desired, such as in laundry and cleaning applications, in feed, food, pulp and paper and oil industry. The invention also provides useful mannanases enzymes, polynucleotides encoding these enzymes, enzyme compositions and methods for their production and use.

BACKGROUND

Mannans are mannose containing polysaccharides found in various plants. Mannans are poorly soluble in aqueous environment and their physicochemical properties give rise to viscous dispersions. Additionally, mannans have high water binding capacity. All of these characteristics cause problems in several industries including brewing, baking, animal nutrition, and laundry and cleaning applications.

In plant-based diets different β-mannans are present and depending on their amounts and properties they can compromise nutrient digestion, microbial colonisation and growth performance. Enzymatic degradation of mannans reduces digesta viscosity of high water soluble mannans and leads to production of manno-oligosaccharides that may form water-insoluble linear mannans present in leguminoseae. Mannanase increases average daily gain, feed efficiency, weight uniformity and livability in all monogastric animals.

For animal feed applications, such as feed for monogastric animals with cereal diets, mannan is a contributing factor to viscosity of gut contents and it thereby adversely affects the feed digestibility and animal growth rate. For ruminants, mannan represents a substantial component of fiber intake and a more complete digestion of mannan would facilitate higher feed conversion efficiencies.

For laundry and cleaning applications enzyme compositions comprising mannanase can be used to degrade mannan. However, providing mannanases that are stable in varying storage and use conditions while still showing good mannan degrading activity is difficult.

Stability of industrial enzymes is an important property because the enzymes are often used in conditions that are very different from the natural environment of the enzymes. It is often that a wild type enzyme showing good performance in initial tests is not suitable for production in industrial scale, or is unstable in typical application or storage conditions.

N-linked glycosylation of proteins is a type of post-translational modification where a sugar molecule oligosaccharide known as glycan is attached to an amide nitrogen group of an asparagine (Asn, N) residue of a protein. This type of linkage is important for both the structure and function of enzymes and other proteins.

It is an object of the present invention to provide variants of mannanase having improved stability and exhibiting mannanase activity when applied in different industrial processes, as well as enzyme compositions for mannan degradation or modification.

SUMMARY

According to the first aspect is provided variant of mannanase comprising at least one substitution of an amino acid at a position corresponding to the position 123, 158, 180, 272, 307, or 316 wherein the variant has mannanase activity and is selected from the group consisting of
  1) a polypeptide having at least 85% sequence identity to residues 27-331 of SEQ ID NO: 2;
  2) a variant encoded by a polynucleotide that hybridizes under high stringency conditions with
     a) nucleotides 79-993 of SEQ ID NO: 1 (man7)
     b) the full-length complement of a); and
  3) a variant encoded by a polynucleotide having at least 95% sequence identity to the SEQ ID NO: 1 or the genomic DNA sequence thereof;
and wherein the amino acid numbering corresponds to the amino acid numbering of SEQ ID NO: 2 (Man7) full-length amino acid sequence containing a signal sequence.

The present variant of mannanase is advantageous in having good stability and mannanase activity. The variant has improved stability in detergents and in particular at high temperature. Thus, the present variant of mannanase may provide improved yield in production and better performance in use. The stability of the variant is particularly good in detergents and at temperatures typically used in applications where mannan degradation is used, such as in laundry detergents.

According to the second aspect of the invention is provided an enzyme composition comprising the variant of mannanase of the first aspect and
  a. at least one preservative selected for example from group consisting of organic acid, citric acid, ascorbic acid, benzoic acid and their salts and derivatives, sodium benzoate, benzoate, hydroxybenzoate and derivatives, sorbic acid, sodium sorbate, sorbate, salts, such as sodium chloride or potassium chloride, 1,2-Benzisothiazolin-3-one (BIT) or a combination thereof;
  b. optionally at least one stabilizer selected from polyol, propylene glycol, polyethylene glycol, hexylene glycol, glycerol, a sugar, sugar alcohol, polysaccharide, lactic acid, boric acid, boric acid derivative, aromatic borate ester, 4-formylphenyl boronic acid, phenyl boronic acid derivative, peptide, surfactant or a combination thereof;
  c. optionally at least one enzyme selected from proteases, amylases, cellulases, lipases, xylanases, mannanases, cutinases, esterases, phytases, DNAses, pectinases, pectinolytic enzymes, pectate lyases, carbohydrases, arabinases, galactanases, xanthanases, xyloglucanases, laccases, peroxidases and oxidases with or without a mediator, or a combination thereof; and
  d. optionally at least one filler selected from maltodextrin, flour, sodium chloride, sulfate, sodium sulfate, or a combination thereof.

As evidenced by the Examples, the variants comprised in the enzyme composition according to the invention have a structure and properties that allow production in recombinant host cells and make them useful in enzyme compositions for industrial applications. The enzyme composition is particularly good for detergent formulations because the variant of mannanase has good stability, wash performance and specific activity when used to degrade mannan in laundry and washing use.

According to the third aspect there is provided a detergent composition comprising the variant of mannanase of the first aspect or the enzyme composition of the second aspect.

The present detergent composition is advantageous in that it is stable, efficient and economical in removing mannan containing stains.

According to another aspect is provided a use of, and a method of using, the present enzyme composition or the present variant of mannanase in a detergent.

According to the fourth aspect is provided a recombinant host cell comprising genetic elements that allow producing at least one recombinant polypeptide comprising the variant of mannanase of the first aspect.

According to the fifth aspect is provided a method for producing a recombinant polypeptide having mannanase activity and comprising:
- a. cultivating a recombinant host cell of the fourth aspect, wherein
  - the genetic elements comprise at least one control sequence which controls the production of the recombinant polypeptide in the recombinant host cell;
  - the genetic elements optionally comprise at least one sequence encoding a signal sequence for transporting the recombinant polypeptide outside the host cell; and
  - cultivating is carried out in conditions allowing production of the recombinant polypeptide; and
- b. recovering the recombinant polypeptide.

The method provides an efficient way to produce a recombinant polypeptide comprising a variant of mannanase. Because the variant of mannanase is produced in a recombinant host cell, a production system is provided which can be optimized, tailored, and controlled in a desired manner. The variant of mannanase produced by the method may differ from natural mannanases at a structural and functional level.

According to another aspect is provided an enzyme preparation comprising a recombinant polypeptide having mannanase activity and obtainable by using the present host cell.

The enzyme preparation or the enzyme composition may further comprise other enzyme(s) selected from the group consisting of proteases, amylases, cellulases, lipases, xylanases, mannanases, cutinases, esterases, phytases, DNAses, pectinases, pectate lyases, pectinolytic enzymes, carbohydrases, arabinases, galactanases, xanthanases, xyloglucanases, laccases, peroxidases and oxidases with or without a mediator, as well as suitable additives selected from the group consisting of stabilizers, buffers, surfactants, bleaching agents, mediators, anti-corrosion agents, builders, anti-redeposition agents, optical brighteners, dyes, pigments, perfumes, caustics, abrasives and preservatives.

According to a sixth aspect is provided a method for degrading or modifying mannan containing material comprising treating said mannan containing material with an effective amount of the present enzyme composition or the present variant of mannanase.

According to the seventh aspect is provided an animal feed comprising the present enzyme composition or the present variant of mannanase, and at least one protein source of plant origin or a mannan containing product or by-product, and
- a. Optionally at least one enzyme selected from protease, amylase, phytase, xylanase, endoglucanase, beta-glucanase, or a combination thereof; and
- b. Optionally at least one filler selected from maltodextrin, flour, salt, sodium chloride, sulfate, sodium sulfate, or a combination thereof.

According to the eighth aspect is provided a feed supplement comprising the present enzyme composition or the present variant of mannanase, and
- a. Optionally at least one enzyme selected from protease, amylase, phytase, xylanase, endoglucanase, beta-glucanase, or a combination thereof; and
- b. Optionally at least one filler selected from maltodextrin, flour, salt, sodium chloride, sulfate, sodium sulfate, or a combination thereof.

The feed and the feed supplement improve nutritional value of feed compared to a feed without the variant. The present enzyme composition comprises the variant of mannanase, which has improved stability. The present enzyme composition and the present variant degrade mannan present in the feed and thereby make it more easily digestible for the animal. In particular for soybean meal containing feeds mannan-oligosaccharides that result from enzymatic digestion have a beneficial effects on the intestinal microbes, and consequently on the performance of the animals. The effect of the variants of mannanase can be enhanced by including xylanase to digest arabinoxylans present in corn soybean based diets. The present variants can also be used to modify rheological properties of wet feeds.

In an embodiment the feed may comprise animal protein, such as meat meal or bone meal.

According to another aspect is provided a use of, and a method of using, the present animal feed or the present feed supplement in:
- a. feeding animals;
- b. improving weight gain of animals.

In an embodiment the animal is a monogastric animal or a ruminant. In another embodiment the animal is a broiler chicken, egg-laying chicken, swine, turkey, or an aquaculture organism such as fish. In another embodiment the animal is a ruminant.

According to a ninth aspect is provided a use of, and a method of using, the present variant or the present enzyme composition in oil drilling or hydro-fracturing.

The present enzyme composition and the present variant are advantageous in modifying rheological properties of oil drilling fluids and hydro-fracturing fluids, and to improve oil recovery.

According to an tenth aspect is provided a use of, and a method of using, the present variant or the present enzyme composition in processing coffee extract, fruit juice, pineapple juice, or soya milk.

Using the present variant and the present enzyme composition is advantageous in processing coffee extract because it reduces viscosity of the coffee extract.

Using the present variant and the present enzyme composition is advantageous in processing and manufacturing fruit juice because it lowers viscosity and improves filtration rate, stability and helps to extract fruit components.

Using present variant and the present enzyme composition is advantageous in processing and manufacturing soya milk because it improves yield, colour, protein content and taste of soya milk.

In another aspect is provided a nucleic acid molecule encoding the present variant of mannanase.

In another aspect is provided a vector comprising the present nucleic acid molecule.

In another aspect is provided a functional fragment of the present variant of mannanase, and a polynucleotide encoding it.

In another aspect the disclosed sequence information herein relating to a polynucleotide sequence encoding a mannanase of the invention can be used as a tool to identify other homologous mannanases. For instance, polymerase chain reaction (PCR) can be used to amplify sequences encoding other homologous mannanases from a variety of biological sources. In addition, genome mining approaches can be used to identify sequences encoding other homologous mannanases from genome databases.

BRIEF DESCRIPTION OF THE FIGURES

FIG. 3A shows variants TBH1, TBH2, TBH3, TBH4, TBH5, TBH6, TBH7, TBH8, TBH9 and wild type.

FIG. 3B shows variants TBH6, TBH10, TBH11 and wild type.

FIG. 4A shows variants TBH1, TBH2, TBH3, TBH4, TBH5, TBH6, TBH7, TBH8, TBH9 and wild type.

FIG. 4B shows variants TBH6, TBH10, TBH11 and wild type.

FIG. 11A shows variants TBH1, TBH2, TBH3, TBH4, TBH5, TBH6, TBH7, TBH8, TBH9 and wild type.

FIG. 11B shows variants TBH6, TBH10, TBH11 and wild type.

DEPOSITS

Figure 1:
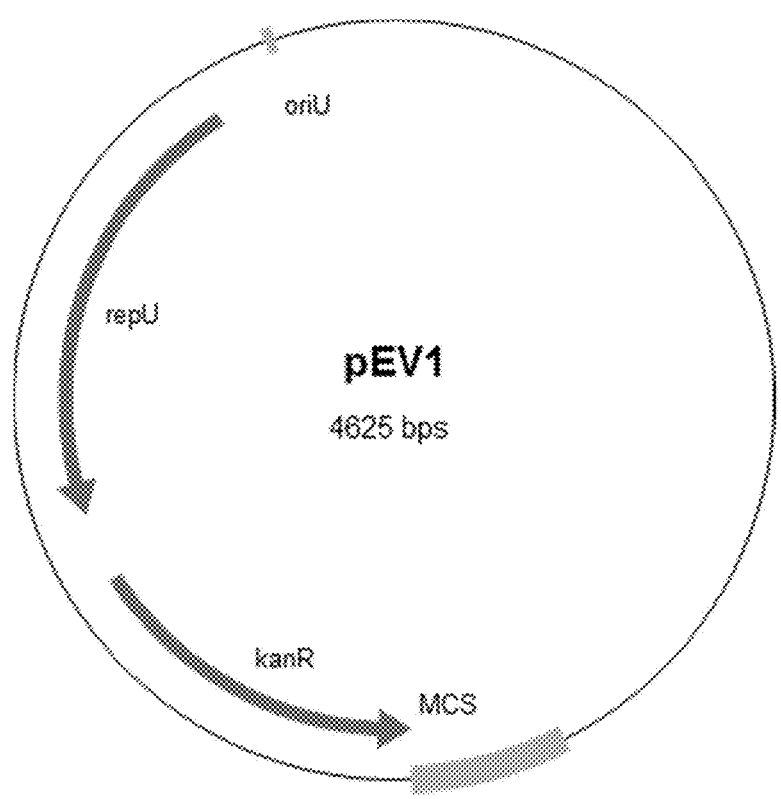
FIG. 1 shows schematic representation of vector pEV1 for replication in *Bacillus*.

The following strain depositions according to the Budapest Treaty on the International Recognition of Deposit of Microorganisms for the Purposes of Patent Procedure were made:

The *E. coli* strain RF12379 including the plasmid pALK4434 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32425.

The *E. coli* strain RF12380 including the plasmid pALK4435 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32426.

The *E. coli* strain RF12381 including the plasmid pALK4436 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32427.

The *E. coli* strain RF12382 including the plasmid pALK4437 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32428.

The *E. coli* strain RF12383 including the plasmid pALK4438 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32429.

The *E. coli* strain RF12384 including the plasmid pALK4439 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32430.

The *E. coli* strain RF12385 including the plasmid pALK4440 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32431.

The *E. coli* strain RF12386 including the plasmid pALK4441 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32432.

The *E. coli* strain RF12387 including the plasmid pALK4442 was deposited at the Deutsche Sammlung von Mikroorganismen und Zellkulturen GmbH (DSMZ), Inhoffenstrasse 7 b, D-38124 Braunschweig, Germany on 2 Mar., 2017 and assigned accession number DSM 32433.

The *E. coli* strain RF12456 including the plasmid pALK4432 was deposited at the Deutsche Sammlung von Mikroorganismen und Zellkulturen GmbH (DSMZ), Inhoffenstrasse 7 b, D-38124 Braunschweig, Germany on 18 May, 2017 and assigned accession number DSM 32518.

The *E. coli* strain RF12457 including the plasmid pALK4433 was deposited at the Deutsche Sammlung von Mikroorganismen and Zellkulturen GmbH (DSMZ), Inhoffenstrasse 7 b, D-38124 Braunschweig, Germany on 18 May, 2017 and assigned accession number DSM 32519.

SEQUENCE LISTINGS

SEQID NO: 1 DNA sequence of the man7
SEQID NO: 2 Full-length amino acid sequence of the Man7
SEQID NO: 3 Deduced amino acid sequence (mature) of the Man7
SEQID NO: 4 Core amino acid sequence of the Man7, no CMB
SEQID NO: 5 Synthetic gene sequence of the variant tbh1
SEQID NO: 6 Deduced amino acid sequence (mature) of the variant TBH1
SEQID NO: 7 Synthetic gene sequence of the variant tbh2
SEQID NO: 8 Deduced amino acid sequence (mature) of the variant TBH2
SEQID NO: 9 Synthetic gene sequence of the variant tbh3
SEQID NO: 10 Deduced amino acid sequence (mature) of the variant TBH3
SEQID NO: 11 Synthetic gene sequence of the variant tbh4
SEQID NO: 12 Deduced amino acid sequence (mature) of the variant TBH4
SEQID NO: 13 Synthetic gene sequence of the variant tbh5
SEQID NO: 14 Deduced amino acid sequence (mature) of the variant TBHS
SEQID NO: 15 Synthetic gene sequence of the variant tbh6
SEQID NO: 16 Deduced amino acid sequence (mature) of the variant TBH6
SEQID NO: 17 Synthetic gene sequence of the variant tbh7
SEQID NO: 18 Deduced amino acid sequence (mature) of the variant TBH7
SEQID NO: 19 Synthetic gene sequence of the variant tbh8
SEQID NO: 20 Deduced amino acid sequence (mature) of the variant TBH8
SEQID NO: 21 Synthetic gene sequence of the variant tbh9
SEQID NO: 22 Deduced amino acid sequence (mature) of the variant TBH9
SEQID NO: 23 Synthetic gene sequence of the variant tbh10
SEQID NO: 24 Deduced amino acid sequence (mature) of the variant TBH10
SEQID NO: 25 Synthetic gene sequence of the variant tbh11
SEQID NO: 26 Deduced amino acid sequence (mature) of the variant TBH11
SEQID NO: 27 DNA sequence of the variant bh18
SEQID NO: 28 Deduced amino acid sequence (mature) of the variant BH18
SEQID NO: 29 DNA sequence of the variant bh21
SEQID NO: 30 Deduced amino acid sequence (mature) of the variant BH21
SEQID NO: 31 DNA sequence of the variant bh23
SEQID NO: 32 Deduced amino acid sequence (mature) of the variant BH23
SEQID NO: 33 DNA sequence of the variant bh24
SEQID NO: 34 Deduced amino acid sequence (mature) of the variant BH24
SEQID NO: 35 DNA sequence of the variant bh25
SEQID NO: 36 Deduced amino acid sequence (mature) of the variant BH25
SEQID NO: 37 Sequence of the oligonucleotide primer Man7_Var1
SEQID NO: 38 Sequence of the oligonucleotide primer Man7_Var2
SEQID NO: 39 Sequence of the oligonucleotide primer Man7_Var3
SEQID NO: 40 Sequence of the oligonucleotide primer Man7_Var4
SEQID NO: 41 Sequence of the oligonucleotide primer Man7_Var5
SEQID NO: 42 Sequence of the oligonucleotide primer Man7_Var6
SEQID NO: 43 Sequence of the oligonucleotide primer Man7_Var7
SEQID NO: 44 Sequence of the oligonucleotide primer Man7_Var8
SEQID NO: 45 Sequence of the oligonucleotide primer Man7_Var9
SEQID NO: 46 Sequence of the oligonucleotide primer Man7_Var10
SEQID NO: 47 Sequence of the oligonucleotide primer Man7_Var11
SEQ ID NO: 48 Sequence of the oligonucleotide primer Man7_Var12

DETAILED DESCRIPTION

Mannan refers to polysaccharides consisting of a mannose backbone linked together by β-1,4-linkages with side-chains of galactose attached to the backbone by α-1,6-linkages. Mannans comprise plant-based material such as guar gum and locust bean gum. Glucomannans are polysaccharides having a backbone of more or less regularly alternating β-1,4 linked mannose and glucose, galactomannans and galactoglucomannans are mannans and so glucomannans with alpha-1,6 linked galactose side branches.

The term "functional fragment" or "effective fragment" means a fragment or portion of the SEQ ID NO: 2 variant that retains about the same enzymatic function or effect.

The term "mannanase variants" and "variant of mannanase" means any mannanase molecule obtained by site-directed or random mutagenesis, insertion, substitution, deletion, recombination and/or any other protein engineering method, which leads to mannanases that differ in their amino acid sequence from the parent mannanase, i.e. a wild-type mannanase. The terms "wild type mannanase", "wild type enzyme", "wild type", or "wt" in accordance with the disclosure describe a mannanase enzyme with an amino acid sequence found in nature or a fragment thereof.

The term "catalytic activity" or "activity" describes quantitatively the conversion of a given substrate under defined reaction conditions. The term "residual activity" is defined as the ratio of the catalytic activity of the enzyme under a certain set of conditions to the catalytic activity under a different set of conditions. Therefore the residual activity $a_i$ is given by $a_i = v_i/v_0$ where v denotes any measure of catalytic activity and $a_i*100$ is the relative activity in percent. The term "specific activity" describes quantitatively the catalytic activity per amount of enzyme under defined reaction conditions.

The term "proteolytic stability" describes the property of a protein to withstand a limited exposure to proteases under conditions where the proteases are active, without losing activity under conditions where its activity can be measured.

As used herein, the term "mannanase" or "galactomannanase" denotes a mannanase enzyme defined according to that known in the art as mannan endo-1,4-beta-mannosidase and having the alternative names beta-mannanase and endo-1,4-mannanase and catalysing hydrolysis of 1,4-beta-D-mannosidic linkages in mannans, galactomannans, glucomannans, and galactoglucomannans. Mannanases are classified according to the Enzyme Nomenclature as EC 3.2.1.78.

As used herein, "isolated" means a substance in a form or environment that does not occur in nature. Non-limiting examples of isolated substances include (1) any non-naturally occurring substance, (2) any substance including any enzyme, variant, nucleic acid, protein, peptide or cofactor, that is at least partially removed from one or more or all of the naturally occurring constituents with which it is associated in nature; (3) any substance modified by the hand of man relative to that substance found in nature, such as a variant; or (4) any substance modified by increasing or decreasing the amount of the substance relative to other components with which it is naturally associated (e.g., recombinant production in a host cell; one or multiple copies of a gene encoding the substance; and use of an alternative promoter to the promoter naturally associated with the gene encoding the substance). In an embodiment a polypeptide, enzyme, variant, polynucleotide, host cell or composition of the invention is isolated.

As used herein, the term "comprising" includes the broader meanings of "including", "containing", and "comprehending", as well as the narrower expressions "consisting of" and "consisting only of".

As used herein, "variant" means a sequence or a fragment of a sequence (nucleotide or amino acid) inserted, substituted or deleted by one or more nucleotides/amino acids, or which is chemically modified. In an embodiment the term variant also includes a recombinant mannanase enzyme.

As used herein, "conservative amino acid substitution" is one in which the amino acid residue is replaced with an amino acid residue having a similar side chain. Families of amino acid residues having similar side chains have been defined in the art. In an embodiment the conservative amino acids in the present description refer to the amino acids within following groupings: Hydrophobic (F W Y H K M I L V A G C); Aromatic (F W Y H); Aliphatic (I L V); Polar (W Y H K R E D C S T N Q); Charged (H K R E D); Positively charged (H K R); Negatively charged (E D); Small (V C A G S PT N D); Tiny (A G S). Thus, a conservative substitution occurs when an amino acid is substituted with an amino acid in the same group.

In an embodiment the substitution is a substitution with at least one amino acid residue. In a further embodiment the at least amino acid is Ala.

As used herein, a "non-conservative amino acid substitution" is one in which an amino acid is substituted with an amino acid in a different group as defined above. The non-conservative substitution may result into a change of an amino acid to another amino acid with different biochemical properties, such as charge, hydrophobicity and/or size. In an embodiment the non-conservative substitution changes at least one property of the variant, such as stability, glycosylation pattern, folding, structure, activity, or affinity.

N-linked glycosylation process occurs in eukaryotes, but very rarely in bacteria. The attachment of a glycan residue to a protein requires the recognition of a consensus sequence. N-linked glycans are almost always attached to an asparagine (Asn) side chain that is present as a part of Asn-X-Ser/Thr consensus sequence, wherein X is any amino acid except for proline (Pro). The inventors have also found that a non-glycosylated Asn side chain structurally close to the active site of the mannanase is important for obtaining a variant with good mannan degrading performance. Without being bound to any theory, glycan sugars are polar molecules and when attached to an Asn, they locate on the surface of the protein causing structural changes in the glycosylated Asn and in its vicinity. Site directed mutagenesis of Asn or Ser/Thr residues in the Asn-Xaa-Thr(Ser) consensus sequence can be used to prevent glycosylation of the desired N-linked glycosylation sites in the variant of the first aspect of the invention.

In an embodiment the variant has a substitution of an amino acid by a residue which prevents N-linked glycosylation of the residue 283 when expressed in a host cell capable of N-linked glycosylation.

In an embodiment the present variant comprises at least one Asn-X-Ser/Thr consensus sequence.

In an embodiment the present variant comprises Pro residue in the location X of the at least one Asn-X-Ser/Thr consensus sequence.

In an embodiment the substitution is either a conservative or a non-conservative substitution.

As used herein, a "peptide" and a "polypeptide" are amino acid sequences including a plurality of consecutive polymerized amino acid residues. For purpose of this invention, peptides are molecules including up to 20 amino acid residues, and polypeptides include more than 20 amino acid residues. The peptide or polypeptide may include modified amino acid residues, naturally occurring amino acid residues not encoded by a codon, and non-naturally occurring amino acid residues. As used herein, a "protein" may refer to a peptide or a polypeptide of any size. A protein may be an enzyme, a protein, an antibody, a membrane protein, a peptide hormone, regulator, or any other protein.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

As used herein, "modification", "modified", and similar terms in the context of polynucleotides refer to modification in a coding or a non-coding region of the polynucleotide, such as a regulatory sequence, 5' untranslated region, 3' untranslated region, up-regulating genetic element, down-regulating genetic element, enhancer, suppressor, promoter, exon, or intron region. The modification may in some embodiments be only structural, having no effect on the biological effect, action or function of the polynucleotide. In other embodiments the modification is a structural modification, which provides a change in the biological effect, action or function of the polynucleotide. Such a modification may enhance, suppress or change the biological function of the polynucleotide.

As used herein, "identity" means the percentage of exact matches of amino acid residues between two aligned sequences over the number of positions where there are residues present in both sequences. When one sequence has a residue with no corresponding residue in the other sequence, the alignment program allows a gap in the alignment, and that position is not counted in the denominator of the identity calculation. Identity is a value determined with the Pairwise Sequence Alignment tool EMBOSS Needle at the EMBL-EBI website (www.ebi.ac.uk/Tools/psa/emboss_needle/).

As used herein, low stringency conditions mean for probes of at least 100 nucleotides in length conditions corresponding to hybridizing at prehybridisation and hybridisation at 55° C. in 5×SSC, 0.1% N-lauroylsarcosine, 0.02% SDS, 1% blocking reagent (Roche 11 096 176 001), following standard Southern blotting procedures for 12 to 24 hours. The carrier material is finally washed two to three times each for 15 minutes using 2×SSC, 0.1% SDS at 55° C.

As used herein, high stringency conditions mean for probes of at least 100 nucleotides in length conditions corresponding to hybridizing at prehybridisation and hybridization at 65° C. in 5×SSC, 0.1% N-lauroylsarcosine, 0.02% SDS, 1% blocking reagent (Roche 11 096 176 001), following standard Southern blotting procedures for 12 to 24 hours. The carrier material is finally washed two to three times each for 15 minutes using 0.1×SSC, 0.1% SDS at 65° C.

As used herein, "host cell" means any cell type that is susceptible to transformation, transfection, transduction, mating, crossing or the like with a nucleic acid construct or expression vector comprising a polynucleotide. The term "host cell" encompasses any progeny that is not identical due to mutations that occur during replication. Non-limiting examples of a host cell are fungal cells, filamentous fungal cells from Division *Ascomycota*, Subdivision *Pezizomycotina*; preferably from the group consisting of members of the Class *Sordariomycetes*, Subclass *Hypocreomycetidae*, Orders *Hypocreales* and *Microascales* and *Aspergillus, Chrysosporium, Myceliophthora* and *Humicola*; more preferably from the group consisting of Families *Hypocreacea, Nectriaceae, Clavicipitaceae, Microascaceae*, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium*, and *Scedosporium*, more preferably from the group consisting of *Trichoderma reesei* (Hypocrea jecorina), T. citrinoviridae, T. longibrachiatum, T. virens, T. harzianurn, T. asperellum, T. atroviridae, T. parareesei, Fusarium oxysporum, F. gramineanum, F. pseudograminearum, F. venenaturn, Gibberella fujikuroi, G. moniliformis, G. zeaea, Nectria (Haematonectria) haematococca, Stachybotrys chartarum, S. chlorohalonata, Claviceps purpurea, Metarhizium acridum, M. anisopliae, Villosiclava virens, Ophiocordyceps sinensis, Acremonium (Cephalosporium) chrysogenum, and Scedosporium apiospermum, and Aspergillus niger, Aspergillus awamori, Aspergillus oryzae, Chrysosporium lucknowense, Myceliophthora thermophila, Humicola insolens, and *Humicola grisea*, most preferably *Trichoderma reesei*. Non-limiting examples of a host cell are bacterial cells, preferably gram positive Bacilli (e.g. *Bacillus subtilis, B. licheniformis, B. megaterium, B. amyloliquefaciens, B. pumilus*), gram-negative bacteria (e.g. *Escherichia coli*), actinomycetales (e.g. *Streptomyces* sp.) and yeasts (e.g. *Saccharomyces cerevisiae, Pichia pastoris, Yarrowia lipolytica*).

In an embodiment the host cell is a fungal cell, preferably a filamentous fungal cell, such as *Trichoderma* or *Trichoderma reesei*. In an embodiment the host cell is a bacterial cell, preferably a gram positive *Bacillus* cell, such as *B. subtilis, B. licheniformis, B. megaterium, B. amyloliquefaciens, B. pumilus.*

In an embodiment the host cell is capable of N-linked glycosylation.

A "recombinant cell" or "recombinant host cell" refers to a cell or host cell, which has been genetically modified or altered to comprise a nucleic acid sequence which is not native to said cell or host cell. The genetic modification may comprise integrating the polynucleotide in the genome of the host cell. The polynucleotide may also be exogenous in the host cell. In an embodiment the present host cell is a recombinant host cell.

As used herein, "expression" includes any step involved in the production of a polypeptide in a host cell including, but not limited to, transcription, translation, post-translational modification, and secretion. Expression may be followed by harvesting, i.e. recovering, the host cells or the expressed product.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, carrier and the like. Expression vectors are generally derived from plasmid or viral DNA, or may contain elements of both. The expression vector may be any expression vector that is conveniently subjected to recombinant DNA procedures, and the choice of vector will often depend on the host cell into which the vector is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. In an embodiment the present vector is an expression vector.

The term "recombinant produced" or "recombinantly produced" used herein in connection with production of a polypeptide or protein is defined according to the standard definition in the art.

The term "obtained from" and "obtainable" as used herein in connection with a specific microbial source means that the polynucleotide is expressed by the specific source (homologous expression), or by a cell in which a gene from the source has been inserted (heterologous expression).

The term "enzyme composition" means either a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species or the fermentation product of a microorganism which acts as a host cell for production of a recombinant mannanase, but which microorganism simultaneously produces other enzymes.

The term "operably linked", when referring to DNA segments, denotes that the segments are arranged so that they function in concert for their intended purposes, e.g. transcription initiates in the promoter and proceeds through the coding segment to the terminator.

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" or "signal sequence" denotes a DNA sequence that encodes a polypeptide (a "secretory peptide") that, as a component of a larger polypeptide, directs the larger polypeptide through a secretory pathway of a host cell in which it is produced. The secretory signal sequence can be native or it can be replaced with secretory signal sequence or carrier sequence from another source. Depending on the host cell, the larger peptide may be cleaved to remove the secretory peptide during transit through the secretory pathway.

The term "core region" or "catalytic domain" denotes a domain of an enzyme, which may or may not have been modified or altered, but which has retained at least part of its original activity. The core region of a mannanase according to the invention corresponds to the amino acids aligned with the amino acids 27-331 of Man7, SEQ ID NO: 2.

By the term "linker" or "spacer" is meant a polypeptide comprising at least two amino acids which may be present between the domains of a multidomain protein, for example an enzyme comprising an enzyme core and a binding domain such as a carbohydrate binding module (CBM) or any other enzyme hybrid, or between two proteins or polypeptides produced as a fusion polypeptide, for example a fusion protein comprising two core enzymes. For example, the fusion protein of an enzyme core with a CBM is provided by fusing a DNA sequence encoding the enzyme core, a DNA sequence encoding the linker and a DNA sequence encoding the CBM sequentially into one open reading frame and expressing this construct.

Efficient amount means an amount, which is sufficient to degrade mannose in the selected application.

The following abbreviations are used for amino acids:

| A | Ala | Alanine |
|---|-----|---------|
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Substitutions are described using of the following nomenclature: amino acid residue in the protein scaffold; position; substituted amino acid residue(s). According to this nomenclature the substitution of, for instance, a serine residue for a glycine residue at position 20 is indicated as Ser20Gly or S20G.

The terms "detergent composition" and "detergent" include, unless otherwise indicated, solid, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners; metal cleaners; as well as cleaning auxiliaries such as bleach additives and "stain-stick" or pre-treat types. The terms "detergent", "detergent composition" and "detergent formulation" are used in reference to mixtures, which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the mannanases according to the invention, the term encompasses detergents that may contain e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anticorrosion agents, hydrotropes, fabric hueing agents, dispersants, dye transfer inhibiting agents, fluorescent whitening agents, soil release polymers, anti-redepositions agents, anti-shrink agents, anti-wrinkling agents, bactericides, binders, carriers, dyes, enzyme stabilizers, fabric softeners, fillers, foam regulators, perfumes, pigments, sod suppressors, solvents, and structurants for liquid detergents, structure elasticizing agents, enzyme inhibitors or stabilizers, enzyme activators, transferase(s), hydrolytic enzymes, oxido reductases, bluing agents and fluorescent dyes, antioxidants, and solubilizers.

The term "textile" means any textile material including yarns, yarn intermediates, fibers, non-woven materials, natural materials, synthetic materials, and any other textile material, fabrics made of these materials and products made from fabrics (e.g., garments, linen and other articles). The textile or fabric may be in the form of knits, wovens, denims, non-wovens, felts, yarns, and towelling. The textile may be cellulose based, such as natural cellulosics including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

The term "stability" includes storage stability and stability during use, e.g. during a wash process (in wash stability) and reflects the stability of the mannanase according to the invention as a function of time, e.g. how much activity is retained when the mannanase is kept in solution, in particular in a detergent solution. The stability is influenced by many factors, e.g. pH, temperature, detergent composition e.g. proteases, stabilizers, builders, surfactants etc. The mannanase stability may be measured using the 'activity assay' as described in examples.

"Mannanase activity" as used herein refers to the mannan degrading activity of a polypeptide. Degrading or modifying as used herein means that mannose units are hydrolyzed from the mannan polysaccharide by the mannanase. The mannan degrading activity of the polypeptides according to present invention can be tested according to standard test procedures known in the art. Example 5 provides an example of a standard method for determining mannanase activity.

In an embodiment the present variant comprises at least one further substitution at the position M123, A158, F180, G272, T307, or L316, or a combination thereof.

In an embodiment the substitution comprises a substitution at said position to an amino acid selected from Ala, Arg, Asn, Asp, Cys, Gln, Glu, Gly, His, Ile, Leu, Lys, Met, Phe, Pro, Ser, Thr, Trp, Tyr, and Val.

In an embodiment the variant comprises at least one set of substitutions at the position(s):
M123 and G272; or
A158 and T307; or
L316; or
T307; or
M123, A158 and T307; or
M123 and L316;
A158, T307, and L316;
F180 and L316; or
M123, A158, G272; T307, and L316;
or a combination thereof.

In an embodiment the substitution is a substitution resulting into an improved stability of the variant.

In an embodiment the variant comprises at least one additional substitution selected from:
a substitution which prevents glycosylation of N283;
a substitution of 283, or 285; or
a substitution of N283, T285, or S285; or
a substitution of T285 or S285 to a residue other than T or S
a substitution of T285 or S285 to the residue A.

In an embodiment the additional substitution results into an altered glycosylation of the variant when produced in a host cell capable of N-linked glycosylation.

In an embodiment the variant has mannanase activity and comprises at least one further substitution of an amino acid at a position corresponding to the position 123, 158, 180, 272, 307, or 316, wherein the variant has mannanase activity and is selected from the group consisting of 1) a variant having at least 85% sequence identity to residues 27-331 of SEQ ID NO: 2; 2) a variant encoded by a polynucleotide that hybridizes under high stringency conditions with a) nucleotides 79-993 of SEQ ID NO: 1 (man7) b) the full-length complement of a); and 3) a variant encoded by a polynucleotide having at least 95% sequence identity to the SEQ ID NO: 1 or the genomic DNA sequence thereof; and wherein the amino acid numbering corresponds to the amino acid numbering of SEQ ID NO: 2 (Man7).

In an embodiment the variant comprises a P residue in the position 284 and/or 286. A substitution to a P residue in any or both of the above positions may cause a structural change in the variant, which prevents N-linked glycosylation.

In an embodiment in the present variant the position T285 or S285 is substituted to a residue other than T or S.

In an embodiment in the present variant the position T285 or S285 is substituted to an alanine.

In an embodiment the variant has at least 85% sequence identity to residues 27-331 of SEQ ID NO: 2, and a non-glycosylated Asn residue at position 283 when produced in a host cell capable of N-linked glycosylation.

In an embodiment the present variant comprises at least one additional glycosylated N site, wherein the position corresponding to the N283 is not glycosylated. Such a variant is obtainable by producing the variant in a host cell which is capable of N-glycosylation, resulting into at least partial glycosylation of the other N-glycosylation sites, but wherein the N-glycosylation of N283 is inhibited.

In a further embodiment the present variant does not comprise any glycosylated N site. Such a variant is obtainable by producing the variant in a host cell which is capable of N-glycosylation, resulting into inhibited glycosylation of the variant.

In an embodiment the variant has a predicted molecular weight between 50000 and 51000, preferably between 50800 and 50970, without including the signal sequence.

In an embodiment the variant has a predicted pI between 4.5 and 4.8, preferably between 4.6 and 4.75.

Prediction of pI or molecular weight of a variant can be carried out as described in the Table 3.

In a further embodiment of the invention the variant has mannanase activity. In an embodiment the variant has a non-glycosylated Asn residues at position 283 when produced in a host cell capable of N-linked glycosylation, and increased specific activity compared to a wild type mannanase when produced in a eukaryotic host cell.

In one embodiment of the present enzyme composition, the enzyme composition further comprises one or more additional enzymes selected from the group consisting of protease, lipase, cutinase, amylase, carbohydrase, cellulase, pectinase, pectatelyase, pectinolytic enzyme, esterase, phytase, mannanase, so arabinase, galactanase, xylanase, oxidase, xanthanase, xyloglucanase, DNAse, laccase, and/or peroxidase, preferably selected from the group consisting of proteases, amylases, cellulases and lipases.

The present enzyme composition comprising mannanase and an additional enzyme is advantageous in providing synergistic effect. Such additional enzymes are desired when the present enzyme composition comprising mannanase is used in detergents e.g. when washing stains. Particularly advantageous synergistic enzymes that work with mannanase in detergents are amylases, proteases and cellulases, or a combination thereof, such as a composition comprising mannanase, amylase and protease.

In one embodiment the present enzyme composition is provided in the form of a liquid composition or a solid composition such as solution, dispersion, paste, powder, granule, granulate, coated granulate, tablet, cake, crystal, crystal slurry, gel, or pellet.

In an embodiment the present detergent composition is in the form of a liquid detergent or a solid detergent, preferably in the form of a bar, a homogenous tablet, a tablet having two or more layers, a pouch having one or more compartments, a regular or compact powder, a granule, granulate, a paste, a gel, or a regular, compact or concentrated liquid.

In one embodiment the present detergent composition further comprises one or more additional enzymes selected from the group consisting of protease, lipase, cutinase, amylase, carbohydrase, cellulase, pectinase, pectatelyase, pectinolytic enzyme, esterase, mannanase, arabinase, galactanase, xylanase, oxidase, xanthanase, xyloglucanase, laccase, DNAse and/or peroxidase, preferably selected from the group consisting of proteases, amylases, cellulases and lipases.

The present enzyme composition can also be used in cleaning agents or boosters that are added on top of the detergent during or before the wash and that are for example in the form of liquid, gel, powder, granules or tablets. Enzyme composition and detergent components may also be soaked in a carrier like textiles.

The present invention furthermore relates to the use of, and a method of using, the enzyme composition or the detergent composition as herein disclosed for degrading mannan.

In a further embodiment the present invention relates to the use of, and a method of using, the enzyme composition or the detergent composition as herein disclosed in a laundry process.

The present invention furthermore relates to a method for removing a stain from a surface, comprising contacting the surface with the enzyme composition or the detergent composition as herein disclosed.

The present invention also relates to a method for degrading mannan comprising applying the enzyme composition or the detergent composition as herein disclosed to mannan, preferably wherein the mannan is on a surface of a textile, or at least partially embedded in a textile.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

A composition for use in solid laundry detergent, for example, may include 0.000001%-5%, such as 0.000005-2%, such as 0.00001%-1%, such as 0.00001%-0.1% of enzyme protein by weight of the composition.

A composition for use in laundry liquid, for example, may include 0.000001%-3%, such as 0.000005%-1%, such as 0.00001%-0.1% of enzyme protein by weight of the composition.

A composition for use in automatic dishwash, for example, may include 0.000001%-5%, such as 0.000005%-2%, such as 0.00001%-1%, such as 0.00001%-0.1% of enzyme protein by weight of the composition.

The additional components a-d of the second aspect of the invention provide improved properties for the present enzyme composition. The enzyme composition is compatible with the additional components and improves applicability of the enzyme composition in various uses.

Salts, such as sodium chloride and sodium sulfate function as drying aids.

The present invention furthermore relates to different uses of the present enzyme composition, such as for degrading mannan and for use in a laundry process.

In an embodiment the variant of mannanase comprises a core region.

In an embodiment the variant of mannanase comprises a CBM.

Providing mannanases that retain activity in temperatures above ambient temperature is advantageous for applications wherein mannan degradation is required in such conditions. Further, the mannanases according to invention may have good stability and activity in alkaline conditions, which is advantageous in detergent use and in biomass processing.

In an embodiment the variant of mannanase has an amino acid sequence with at least, or about, 85%, 86%, 87%, 88%, 89%, 90%, 91%, 92%, 93%, 94%, 95%, 96%, 97%, 98%, 99% or 100% sequence identity to SEQ ID NO:2.

In an embodiment the variant of mannanase has an amino acid sequence with at least 90% sequence identity to SEQ ID NO:2.

In an embodiment the mannanase enzyme has an amino acid sequence which is not 100% identical to SEQ ID NO: 2 [Man7].

In an embodiment of the third aspect the host cell is selected from the group consisting of:
fungal cells,
filamentous fungal cells from Division *Ascomycota*, Subdivision *Pezizomycotina*; preferably from the group consisting of members of the Class *Sordariomycetes*, Subclass *Hypocreomycetidae*, Orders *Hypocreales* and *Microascales* and *Aspergillus, Chrysosporium, Myceliophthora* and *Humicola*,
more preferably from the group consisting of Families *Hypocreacea, Nectriaceae, Clavicipitaceae, Microascaceae*, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium,* and *Scedosporium*,
more preferably from the group consisting of *Trichoderma reesei* (*Hypocrea jecorina*), *T. citrinoviridae, T. longibrachiatum, T. virens, T. harzianum, T. asperellum, T. atroviridae, T. parareesei, Fusarium oxysporum, F. gramineanum, F. pseudograminearum, F. venenaturn, Gibberella fujikuroi, G. moniliformis, G. zeaea, Nectria* (*Haematonectria*) *haematococca, Stachybotrys chartarum, S. chlorohalonata, Claviceps purpurea, Metarhizium acridum, M. anisopliae, Villosiclava virens, Ophiocordyceps sinensis, Acremonium* (*Cephalosporium*) *chrysogenum,* and *Scedosporium apiospermum,* and *Aspergillus niger, Aspergillus awamori, Aspergillus oryzae, Chrysosporium lucknowense, Myceliophthora thermophila, Humicola insolens,* and *Humicola grisea,*
bacterial cells, preferably gram positive Bacilli such as *B. subtilis, B. licheniformis, B. megaterium, B. amyloliquefaciens, B. pumilus*, gram negative bacteria such as *Escherichia coli*, actinomycetales such as *Streptomyces* sp., and
yeasts, such as *Saccharomyces cerevisiae, Pichia pastoris, Yarrowia lipolytica,*
most preferably *Trichoderma reesei* or *Bacillus*.

In an embodiment the host cell is a eukaryotic host cell capable of N-linked glycosylation. In a preferred embodiment the host cell is *Trichoderma reesei*.

The recombinant host cell can be used to produce the variant of mannanase and to carry a polynucleotide encoding it. The recombinant host cell is useful also in preparation of variants of mannanase with different properties. For example, a host cell can be selected, which provides post-translational modifications beneficial for stability or activity, or which facilitates post-processing and formulation of the variant of mannanase produced in the host cell.

In an embodiment the present enzyme composition comprises the recombinant host cell of the second aspect.

In an embodiment the present variant of mannanase is a recombinant polypeptide, which is a fusion protein.

In an embodiment the present recombinant polypeptide is a fusion protein, which further comprises at least one of:
an amino acid sequence providing a secretory signal sequence;
so an amino acid sequence which facilitates purification, such as an affinity tag, His-tag;
an amino acid sequence which enhances production, such as an amino acid sequence which is a carrier, such as CBM;
an amino acid sequence having an enzyme activity; and
an amino acid sequence providing for the fusion protein with binding affinity, such as a carbohydrate binding moiety.

The CBM, carbohydrate binding moiety, as a carrier is advantageous e.g. in *Trichoderma* production.

In an embodiment the host cell is non-pathogenic. This is particularly advantageous for using the host cell in feed, and in detergent applications such as in home laundry detergents.

In an embodiment of the fifth aspect the mannan containing material is selected from plant based material, textile, waste water, sewage, oil or a combination thereof.

In an embodiment the mannan containing material is textile material or fabric.

In another embodiment the mannan containing material is recycled waste paper; mechanical pulp, chemical pulp, semi chemical pulp, Kraft or other paper-making pulps; fibres subjected to a retting process; or guar gum or locust bean gum containing material.

In another embodiment degradation or modifying is carried out in an aqueous environment wherein mannanase shows activity.

In a preferred embodiment the mannan containing material, which is degraded or modified in the method, is on a textile or a fabric optionally with mannan stains. By degrading mannan attached to the textile or fabric, dirt or soil bound to mannan is released and not capable of binding again to the mannan or mannan stains. The textile or fabric can be of any material, for example cotton, flax/linen, jute, ramie, sisal or coir or manmade cellulosics (e.g. originating from wood pulp) including viscose/rayon, modal, cellulose acetate fibers (tricell), lyocell, cupro or blends thereof.

In an embodiment the present feed comprises or consists of maize and soybean meal.

In an embodiment the protein source of plant origin comprises or consist of soy, cereal such as barley, wheat, rye, oats, or maize.

In an embodiment the mannan containing product or by-product comprises or consists of palm kernel, guar meal or copra meal.

In an embodiment the present animal feed or the present feed supplement is formulated in the form of a wet composition or a dry composition.

In an embodiment the composition comprising at least one variant of mannanase enzyme is used in pulp and paper industry, biobleaching, fiber modification, drainage improvement and in the oil industry, i.e. in oil drilling or oil-servicing industry for hydro-fracturing or controlling the viscosity of drilling fluids.

In an embodiment the composition comprising at least one variant of mannanase is used in textile and detergent industry, biomass processing and biomass hydrolysis, preferably in biofuel, starch, pulp and paper, food, baking, feed or beverage industries.

In an embodiment the variant of mannanase hydrolyses endo-beta-1,4-mannosidic linkages randomly.

In an embodiment the variant of mannanase, or the nucleotide sequence encoding the corresponding wild type mannanase, is obtainable or derivable from a bacterial source.

In an embodiment the variant of mannanase is fused with at least one further polypeptide, thus forming a fusion polypeptide. The fusion polypeptide or the further polypeptide may have other catalytic or binding activities in addition to those of mannanase. In an embodiment the further polypeptide comprises or consists of carbohydrate binding module, which is optionally a fragment of another protein or enzyme derived from the same or different organism as the mannanase.

In an embodiment the variant of mannanase is connected to the further polypeptide with a linker.

In an embodiment is provided a process for machine treatment of fabrics which process comprises treating fabric during a washing cycle of a machine washing process with a washing solution containing the variant of mannanase of the first aspect or the enzyme composition of the second aspect.

In an embodiment is provided a use of the enzyme composition of the second aspect or the variant of mannanase of the first aspect, together with an enzyme selected from protease, amylase, cellulase, lipase, xylanase, mannanase, cutinase, esterase, phytase, DNAse, pectinase, pectinolytic enzyme, pectate lyase, carbohydrase, arabinase, galactanase, xanthanase, xyloglucanase, laccase, peroxidase and oxidase with or without a mediator in a cleaning composition for fabric cleaning and/or fabric stain removal.

In an embodiment is provided a use of the variant of mannanase of the first aspect, or the enzyme composition of the second aspect, together with an enzyme selected from protease, amylase, cellulase, lipase, xylanase, mannanase, cutinase, esterase, phytase, DNAse, pectinase, pectinolytic enzyme, pectate lyase, carbohydrase, arabinase, galactanase, xanthanase, xyloglucanase, laccase, peroxidase and oxidase with or without a mediator in a cleaning composition for cleaning hard surfaces such as floors, walls, bathroom tile and the like.

In an embodiment is provided a use of the variant of mannanase of the first aspect, or the enzyme composition of the second aspect, together with an enzyme selected from protease, amylase, cellulase, lipase, xylanase, mannanase, cutinase, esterase, phytase, DNAse, pectinase, pectinolytic enzyme, pectate lyase, carbohydrase, arabinase, galactanase, xanthanase, xyloglucanase, laccase, peroxidase and oxidase with or without a mediator in a cleaning composition for hand and machine dishwashing.

EXAMPLES

The following examples are provided to illustrate various aspects of the present invention. They are not intended to limit the invention, which is defined by the accompanying claims.

Example 1

Variant Design

To improve the stability and specific activity of the wild type Man7 mannanase, variant sets were designed based on structural analysis of wild type enzyme. The structural model of Man7 was created using Bioluminate software (Schrödinger LCC) with coordinates from *Bacillus* sp. Endo-Beta-D-1,4-Mannanase (1WKY). The design included two or more specific mutations per variant. Table 1 shows list of variants. The amino acid numbering corresponds to the amino acid numbering of SEQ ID NO: 2 (Man7) full length amino acid sequence containing a signal sequence.

TABLE 1

| List of Man7 variants | |
|---|---|
| Variant | Mutations |
| TBH1: | M123I, S229A G272Q T285A |
| TBH2: | A158S, S229A, T285A, T307R |
| TBH3: | S229A, T285A, L316K |
| TBH4: | M123I A158S, S229A G272Q T285A, T307R |
| TBH5: | M123I, S229A G272Q T285A, L316K |
| TBH6: | A158S, S229A, T285A, T307R L316K |
| TBH7: | F180L S229A, T285A, L316K |
| TBH8: | S229A, T285A |
| TBH9: | S229A, T285A N300Q, N340Q S400A N419A S433A N446Q |
| TBH10: | A158S, S229A, T307R L316K |
| TBH11: | A158S, T285A, T307R L316K |
| BH18: | M123I, G272Q |
| BH21: | A158S, T307R |
| BH23: | M123I A158S, G272Q, T307R |
| BH24: | M123I, G272Q, L316K |
| BH25: | A158S, T307R L316K |

Example 2

Cloning of Synthetic Mannanase Variant Genes

Standard molecular biology methods were used in the isolation and enzyme treatments of DNA (e.g. isolation of plasmid DNA, digestion of DNA to produce DNA fragments), in *E. coli* transformations, sequencing etc. The basic methods used were as described by the enzyme, reagent or kit manufacturer.

Variants tbh1-tbh11 were ordered from GenScript as synthetic constructs without their own signal peptide encoding sequences and with codon optimization for *Trichoderma reesei*. Plasmid DNAs obtained from GenScript including the genes tbh1-tbh11 were resuspended in sterile water, digested with NruI and BamHI restriction enzymes (Thermo Fisher Scientific) according to manufacturer's instructions and cloned into an expression vector cleaved with NruI and BamHI. Ligation mixtures were transformed into *Escherichia coli* XL1-Blue or XL10-Gold cells (AH Diagnostics) and plated on LB (Luria-Bertani) plates containing 50-100 µg/ml ampicillin. Several *E. coli* colonies were collected from the plates and DNA was isolated with GenJet Plasmid Miniprep Kit (Thermo Fisher Scientific). Positive clones were screened using restriction digestions and they were shown to contain inserts of expected sizes. The fusion sites to the expression plasmid of tbh1-tbh11 mannanase genes were sequenced and the plasmids were named pALK4415-pALK4423, pALK4430 and pALK4431, respectively (For details see Example 4). The plasmid DNAs including the thb genes delivered by GenScript were also transformed into XL10-Gold *E. coli* cells (Agilent) and deposited into DSMZ strain collection. The relevant information on the genes and the deduced amino acid sequences (SEQ ID NOs: 5-36) are summarized in Table 2 and Table 3, respectively. The *E. coli* strains RF12379-RF12387, RF12456 and RF12457 including the plasmids pALK4434-pALK4442, pALK4432 and pALK4433, respectively were deposited to the DSMZ collection under the accession numbers DSM 32425, DSM 32426, DSM 32427, DSM 32428, DSM 32429, DSM 32430, DSM 32431, DSM 32432, DSM32433, DSM 32518 and DSM 32519, respectively.

TABLE 2

The summary on the mannanase variant encoding synthetic genes tbh1-tbh11

| Gene | Length (bp)[a] | SEQ ID NO |
|---|---|---|
| tbh1 | 1395 | 5 |
| tbh2 | 1395 | 7 |
| tbh3 | 1395 | 9 |
| tbh4 | 1395 | 11 |
| tbh5 | 1395 | 13 |
| tbh6 | 1395 | 15 |
| tbh7 | 1395 | 17 |
| tbh8 | 1395 | 19 |
| tbh9 | 1395 | 21 |
| tbh10 | 1395 | 23 |
| tbh11 | 1395 | 25 |

[a] The STOP codon is included

TABLE 3

The summary of the amino acid sequences deduced from the mannanase variant encoding gene sequences.

| Man protein | No of aas [b] | Length of s s[a] | CBM | Core (aa-aa) | Predicted (Da), ss not included [b] | Predicted pI, ss not included [b] | SEQ ID NO |
|---|---|---|---|---|---|---|---|
| TBH1 | 464 | 26 | Yes | 27-331 | 50886 | 4.62 | 6 |
| TBH2 | 464 | 26 | Yes | 27-331 | 50904 | 4.67 | 8 |
| TBH3 | 464 | 26 | Yes | 27-331 | 50848 | 4.67 | 10 |
| TBH4 | 464 | 26 | Yes | 27-331 | 50957 | 4.67 | 12 |
| TBH5 | 464 | 26 | Yes | 27-331 | 50901 | 4.67 | 14 |
| TBH6 | 464 | 26 | Yes | 27-331 | 50919 | 4.72 | 16 |
| TBH7 | 464 | 26 | Yes | 27-331 | 50814 | 4.67 | 18 |
| TBH8 | 464 | 26 | Yes | 27-331 | 50833 | 4.62 | 20 |
| TBH9 | 464 | 26 | Yes | 27-331 | 50800 | 4.62 | 22 |
| TBH10 | 464 | 26 | Yes | 27-331 | 50949 | 4.72 | 24 |
| TBH11 | 464 | 26 | Yes | 27-331 | 50935 | 4.72 | 26 |

[a] The prediction on the signal sequence was made using the program SignalP v3.0, NN/HMM (Nielsen et al., 1997; Nielsen & Krogh, 1998; Bendtsen et al., 2004).

[b] The predicted signal sequence was not included. The prediction was made using Clone Manager Professional version 9 for Windows, Sci-Ed Software.

Example 3

Site Directed Mutagenesis of Man7 Gene

Unless otherwise stated, the standard molecular biological methods including DNA manipulations and transformations were used. Mutations were introduced by site directed mutagenesis as described in Kunkel 1985. Mutations generated are listed in Table 4. The amino acid numbering corresponds to the amino acid numbering of SEQ ID NO: 2 (Man7).

TABLE 4

List of mutations introduced in Man7 by site directed mutagenesis

| Variant Nr. | Mutation | SEQ ID NO (nt) | SEQ ID NO (aa) |
|---|---|---|---|
| BH18 | M123I, G272Q | 27 | 28 |
| BH21 | A158S, T307R | 29 | 30 |
| BH23 | M123I, A158S, G272Q, T307R | 31 | 32 |
| BH24 | M123I, G272Q, L316K | 33 | 34 |
| BH25 | A158S, T307R, L316K | 25 | 36 |

For amplification Pfx Accu Prime Polymerase (Invitrogen) was used. PCRs were performed according to manufacturer's instructions. Following PCR conditions were used for construction of the expression plasmids: 120 sec initial denaturation at 94° C., followed by 35 cycles of 15 sec at 94° C., 30 sec annealing at one of the following 50/55° C., 110/290 sec extension at 68° C. and the final extension at 68° C. for 10 min. The pEV1 man7 was used as template for PCR. Sequences of primers used for cloning are shown in Table 5. Overhangs for hybridization are underlined.

TABLE 5

List of primers used for generation of man7 variants

| Template | Primer | Length | Sequence | Seq ID No |
|---|---|---|---|---|
| pEV1 man7 | Man7_Var1 | 30 | GATGCAACAGGATCTAATTCTATTGCTGAC | 37 |
| pEV1 man7 | Man7_Var2 | 34 | GCTAGCCAACCGACTTGTCTTTGTTGCGAGTAGC | 38 |
| pEV1 man7 | Man7_Var3 | 21 | GATCCTGTTGCATCGTGAACC | 39 |
| pEV1 man7 | Man7_Var4 | 20 | GTCGGTTGGCTAGCTTGGTC | 40 |
| pEV1 man7/pEV1 BH18 | Man7_Var5 | 25 | ATGAATGGTATGGATCATGGGACGG | 41 |
| pEV1 man7/pEV1 BH18 | Man7_Var6 | 25 | GGCCCGTGGACAATTCTATTTCCCC | 42 |
| pEV1 man7/pEV1 BH18 | Man7_Var7 | 22 | TCCATACCATTCATTGGCAATG | 43 |
| pEV1 man7/pEV1 BH18 | Man7_Var8 | 20 | ATTGTCCACGGGCCTAATGG | 44 |
| pEV1 Var1/pEV1 BH21 | Man7_Var9 | 21 | GAAACATCCATTCCAAGCTCG | 45 |
| pEV1 Var1/pEV1 BH21 | Man7Var_10 | 31 | AATGGATGTTTCTTTTAATCCATTAGGCCCG | 46 |
| pEV1 Var1/pEV1 BH21 | Man7Var_11 | 36 | CGGTATATCTCTGTCTTATTGGATTGTTACATGATC | 47 |
| pEV1 Var1/pEV1 BH21 | Man7Var_12 | 21 | GACAGAGATATACCGACAGTG | 48 |

For cloning purposes NEBuilder®Hifi DNA Assembly Master Mix (NEB, Frankfurt) was used according to kit manufacturer's instructions. Generated expression plasmids (FIG. 1) were transformed by induced competence in *Bacillus subtilis* SCK6 as described in Zhang & Zhang 2011. The transformed cells were plated onto LB (Luria-Bertani) plates supplemented with 10 mg/l Kanamycin. Plates were incubated for 20 h at 37° C. Growing colonies were picked and plasmid was isolated using QiaPrep MiniPrep Kit (Qiagen, Germany). The isolation procedure was carried out according to the manufacturer's recommendations for Gram positives plasmid preparations. Inserts were sequenced via Sanger sequencing (GATC, Germany) and revealed the DNA sequences corresponding to the mature parts of the variants 1 to 5. Sequence comparisons were done using ClustalW sequence alignment (Thompson et al 1994). Finally, expression plasmids were transformed in a *Bacillus* production strain via electroporation. *Bacillus* production strain was grown in electroporation medium containing 20 g/l Trypton, 10g/l yeast extract, 10 g NaCl and 2 M sucrose and 10 ml were harvested at an OD(600nm) of 0.4. Cells were washed with electroporation buffer containing 0.272 M sucrose, 1 mM MgCl$_2$ and 7 mM KH$_2$PO4 and finally resuspended in 250 µl electroporation buffer. Electroporation was performed using following conditions: 1.2 kV, 150 Ω, 50 µF. 1 ml electroporation medium was added afterwards and cells were incubated for 3 h at 37° C. Cells were plated on LB plates supplemented with 20 mg/l kanamycin and incubated for 18 h at 37° C. Clones were verified as described above and used for generation of material for analytic tests. Therefore, strains were inoculated in a standard expression under protein inducing conditions and incubated for 30 h at 37° C. Supernatants were harvested and used for analytical and application tests.

Example 4

Production of Recombinant Mannanase Variant Proteins in *Trichoderma reesei*

Figure 2:
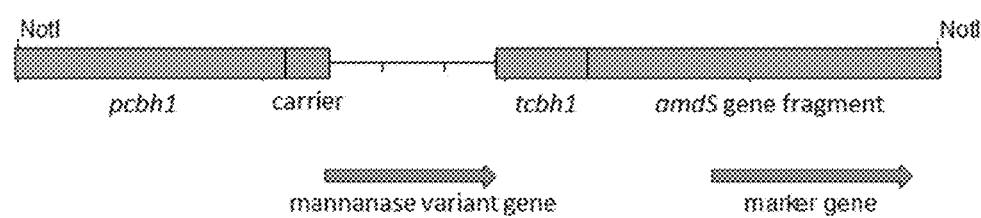
FIG. 2 schematically shows the expression cassettes used in the transformation of *Trichoderma* reesei.

Expression plasmids were constructed for production of recombinant mannanase TBH1-TBH11 (SEQ ID NO: 6, 8, 10, 12, 14, 16, 18, 20, 22, 24 and 26) proteins in *Trichoderma reesei*. The expression plasmids constructed are listed in Table 6. The recombinant mannanase genes without their own signal sequences were fused to the *T. reesei* cel7A/cbh1 promoter with *T. reesei* cel6A/cbh2 CBM carrier and linker followed by Kex2 protease recognition site. The transcription termination was ensured by the *T. reesei* cel7A/cbh1 terminator and the *A. nidulans* amdS marker gene was used for selection of the transformants as described in Paloheimo et al. (2003). The linear expression cassettes (FIG. 2) were isolated from the vector backbones after NotI digestions and were transformed into *T. reesei* protoplasts. The host strains used, do not produce any of the four major *T. reesei* cellulases (CBHI, CBHII, EGI, EGII). The transformations were performed as in Penttilä et al. (1987) with the modifications described in Karhunen et al. (1993), selecting acetamidase as a sole nitrogen source (amdS marker gene). The transformants were purified on selection plates through single conidia prior to sporulating them on PD.

TABLE 6

The expression cassettes constructed to produce TBH1-TBH11 (SEQ ID NO: 6, 8, 10, 12, 14, 16, 18, 20, 22, 24 and 26), recombinant proteins in *Trichoderma reesei*. The overall structure of the expression cassettes was as described in FIG. 2.

| Mannanase protein | Expression plasmid | Expression cassette [a] |
|---|---|---|
| TBH1 | pALK4415 | 7.5 kb NotI |
| TBH2 | pALK4416 | 7.5 kb NotI |
| TBH3 | pALK4417 | 7.5 kb NotI |
| TBH4 | pALK4418 | 7.5 kb NotI |
| TBH5 | pALK4419 | 7.5 kb NotI |
| TBH6 | pALK4420 | 7.5 kb NotI |
| TBH7 | pALK4421 | 7.5 kb NotI |
| TBH8 | pALK4422 | 7.5 kb NotI |
| TBH9 | pALK4423 | 7.5 kb NotI |
| TBH10 | pALK4430 | 7.5 kb NotI |
| TBH11 | pALK4431 | 7.5 kb NotI |

[a] The expression cassette for *T. reesei* transformation was isolated from vector backbone by using NotI digestions.

The mannanase production of the transformants was analyzed from the culture supernatants of the shake flask cultivations. The transformants were inoculated from the PD slants to shake flasks containing 50 ml of complex lactose-based cellulase inducing medium (Joutsjoki at al. 1993) buffered with 5% $KH_2PO_4$. The mannanase protein production of the transformants was analyzed from culture supernatants after growing them for 7 days at 30° C., 250 rpm. Heterologous production of recombinant proteins was analyzed by SDS-PAGE with subsequent Coomassie staining. The supernatants were recovered also for application tests by centrifugation.

The best producing transformants were chosen to be cultivated in laboratory scale bioreactors. The transformants were cultivated in bioreactors either on batch or by additional feeding type of process under protein inducing conditions at a typical mesophilic fungal cultivation temperature and slightly acidic conditions. The cultivation was continued until depletion of the medium sugars or until suitable yield was reached. The supernatants were recovered for application tests by centrifugation or by filtration.

Example 5

Assay of Galactomannanase Activity by DNS-Method

Mannanase activity (MNU) was measured as the release of reducing sugars from galactomannan (0.3 w/w-%) at 50° C. and pH 7.0 in 5 min. The amount of released reducing carbohydrates was determined spectrophotometrically using dinitrosalicylic acid.

Substrate (0.3 w/w-%) used in the assay was prepared as follows: 0.6 g of locust bean gum (Sigma G-0753) was in 50 mM sodium citrate buffer pH 7 (or citrate phosphate buffer pH 7) at about 80° C. using a heating magnetic stirrer and heated up to boiling point. The solution was cooled and let to dissolve overnight in a cold room (2-8° C.) with continuous stirring and insoluble residues were removed by centrifugation. After that solution was filled up to 200 ml by buffer. Substrate was stored as frozen and melted by heating in a boiling water bath to about 80° C., cooled to room temperature and mixed carefully before use.

DNS reagent used in the assay was prepared by dissolving 50 g of 3.5-dinitrosalisylic acid (Sigma D-550) in about 4 liter of water. With continuous magnetic stirring 80.0 g of NaOH was gradually added and let to dissolve. An amount of 1500 g of Rochelle Salt (K—Na-tartrate, Merck 8087) was added in small portions with continuous stirring. The solution that was cautiously warmed to a maximum temperature of 45° C., was cooled to room temperature and filled up to 5000 ml. After that it was filtered through Whatman 1 filter paper and stored in a dark bottle at room temperature.

The reaction was first started by adding 1.8 ml of substrate solution to each of the two test tubes and let to equilibrate at 50° C. for 5 minutes, after which 200 µl of suitably diluted enzyme solution was added to one of the tubes, mixed well with vortex mixer and incubated exactly for 5 min at 50° C. Enzyme blanks didn't need to be equilibrated or incubated. The reaction was stopped by adding 3.0 ml of DNS reagent into both tubes and mixed. 200 µl of sample solution was added to the enzyme blank tubes. Both tubes were placed in a boiling water bath. After boiling for exactly 5 minutes, the tubes were placed in a cooling water bath and allow them to cool to room temperature. The absorbance of sample was measured against the enzyme blank at 540 nm and activity was read from the calibration curve and multiplied by the dilution factor. A suitable diluted sample yielded an absorbance difference of 0.15-0.4.

Standard curve was prepared 20 mM from mannose stock solution by dissolving 360 mg of mannose (SigmaM-6020, stored in a desiccator) in assay buffer and diluted to solutions containing 3, 6, 10 and 14 pmol/ml of mannose. Standards were handled like the samples except for incubating at 50° C. The absorbances were measured against the reagent blank (containing buffer instead of standard dilution of mannose) at 540 nm. Calibration curve was constructed for every series of assays.

One mannanase unit (MNU) was defined as the amount of enzyme that produces reductive carbohydrates having a reductive power corresponding to one nmol of mannose from galactomannan in one second under the assay conditions (1 MNU=1nkat).

Example 6

Stain Removal Performance of Mannanase Variants Produced in *Trichoderma* with Commercial Detergents Cultivation samples of TBH1-TBH11 variants produced in *Trichoderma* (as described in Example 4) were tested for their ability to remove mannanase sensitive standard stains at 40° C. and water hardness of 16° dH with commercial detergents and compared to wild type enzyme. The following artificially soiled test cloths from Center for testmaterial B.V. (the Netherlands) were used: Chocolate pudding mannanase sensitive on cotton (E-165), Locust bean gum, with pigment on cotton (C-S-73) and Guar gum with carbon black on cotton (C-S-43). The fabric was cut in 6 cm×6 cm swatches and 2 pieces of each were used in test.

Commercial heavy duty liquid detergent A containing all other enzymes except mannanase was used at concentration of 4.4 g per liter of wash liquor, Commercial Color detergent powder without enzymes was used at 3.8 g/l and Commercial bleach detergent powder without enzymes was used at 4.2 g/l. Detergent containing wash liquors we prepared in synthetic tap water with hardness of 16° dH. Protease Savinase® 16 L (0.5 w/w %) and amylase Stainzyme® 12 L (0.4 w/w %) was added into hard water used with commercial commercial color and bleach detergent powders, the liquid detergent already contained amylase and protease. pH of the wash liquor of liquid detergent was approximately 8.3, with color detergent powder approx. 10 and with the bleach detergent approx. 9.5.

Mannanases were dosed as 0.025 and/or 0.05 MNU activity per ml of wash liquor. Activity was measured as described in Example 5. Control sample contained the detergent solution without mannanase.

For synthetic tap water with hardness of 16° dH the following stock solutions were prepared in deionized water (Milli-Q or equivalent):

Stock solution with 1000° d Calcium-hardness: CaCl2×2 H2O (1.02382.1000, Merck KGaA, Germany) 26,22 g/l Stock solution with 200° d Magnesium-hardness: MgSO4×7 H2O (1.05886.1000, Merck KGaA, Germany) 8,79 g/l H2O NaHCO3 stock solution: NaHCO3 (1.06329.1000 Merck KGaA, Germany) 29,6 g/l 13,3 ml CaCl2 solution, 13,3 ml MgSO4 solution and 10,0 ml of freshly made NaHCO3 solution were added in volumetric flask in the given order, made up to 1 liter with deionized water and mixed. The hardness of water was determined by complexometric titration and found correct.

Stain removal treatments were performed in Atlas LP-2 Launder-Ometer as follows. Launder-Ometer was first preheated to 40° C. Then detergent, 250 ml synthetic tap water with hardness of 16° dH and diluted enzyme (<1.0 ml) were added into 1,2 liter containers. Stains were added and the Launder-Ometer was run at 40° C. for 60 min with a rotation speed of 42 rpm. After that the swatches were carefully rinsed under running water and dried overnight at indoor air, on a grid protected against daylight.

The stain removal effect was evaluated by measuring the colour as reflectance values with Konica Minolta CM-3610A spectrophotometer using L*a*b* color space coordinates (illuminant D65/10°, 420 nm cut). Fading of the stains, indicating mannanase performance (stain removal efficiency) was calculated as ΔL* (delta L*), which means lightness value L* of enzyme treated fabric minus lightness value L* of fabric treated with washing liquor without mannanase (control).

Final results (total stain removal effect) were shown as sum of ΔL* of each 3 stains. Color values of each stains were average of 2 swatches.

Figure 3A:
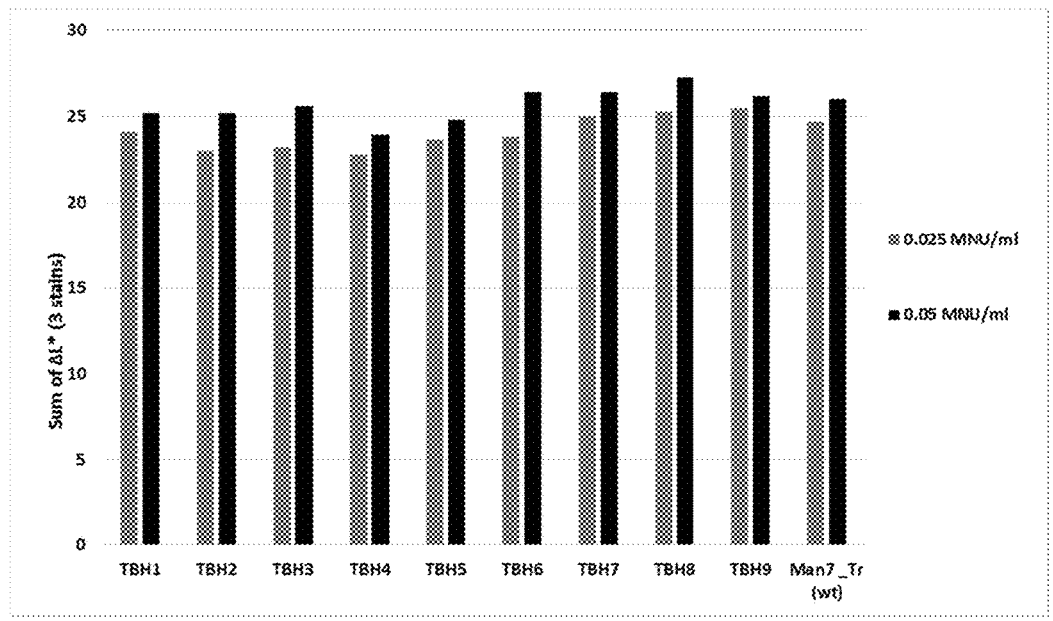
FIG. 3A-B describe the stain removal performance of variants and wild type Man7 (produced in *Trichoderma*) as an increase of lightness (sum of ΔL*of 3 stains) in the presence of 4.4 g/l of Commercial heavy duty liquid detergent A at 40° C., 16° dH, 60 min, pH approx. 8.3 and enzymes dosed as activity units (MNU) per wash liquor.
Figure 3B:
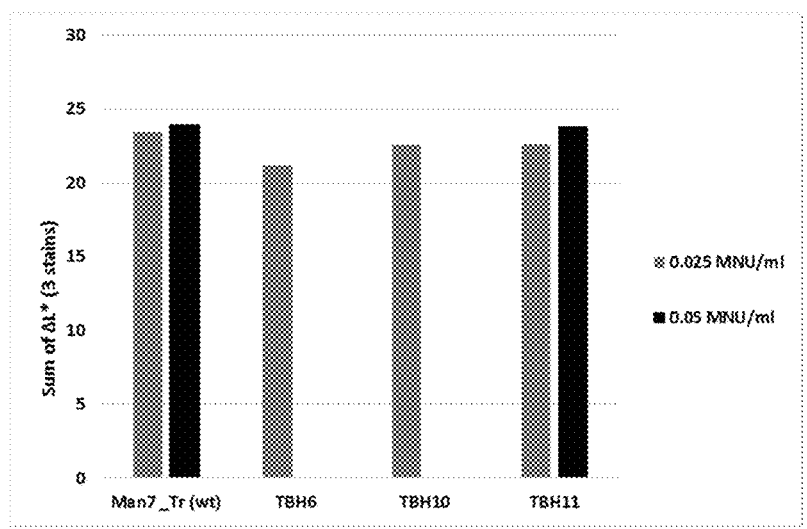
Figure 4A:
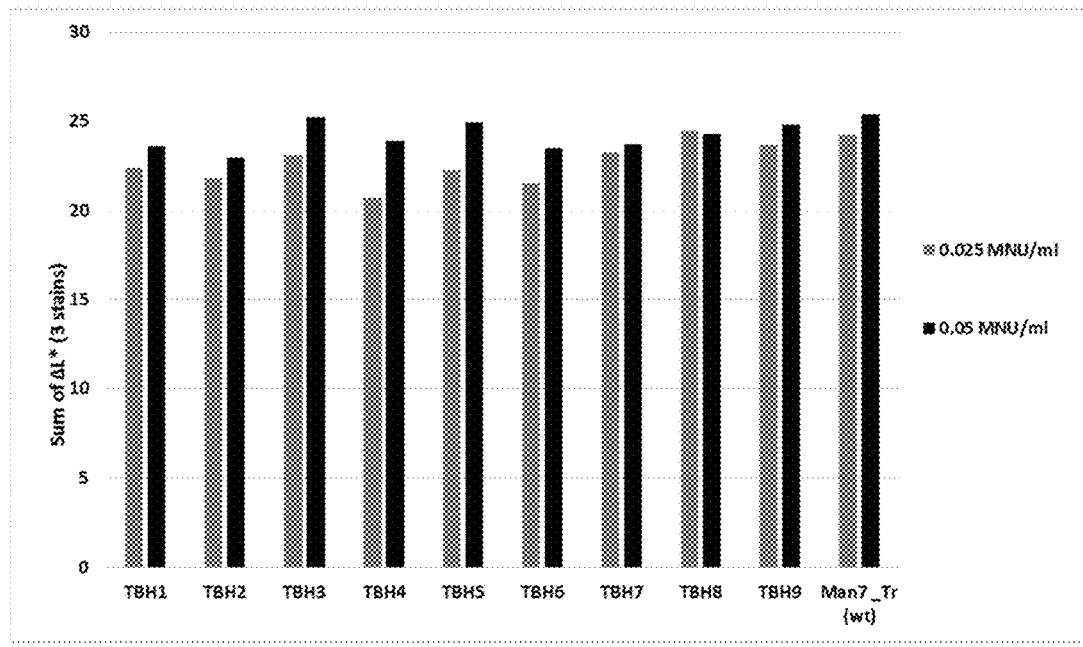
FIG. 4A-B describe the stain removal performance of variants and wild type Man7 (produced in *Trichoderma*) as an increase of lightness (sum of ΔL*of 3 stains) in the presence of 3.8 g/l of Commercial color detergent powder at 40° C., 16° dH, 60 min, pH approx. 10 and enzymes dosed as activity units (MNU) per wash liquor.
Figure 4B:
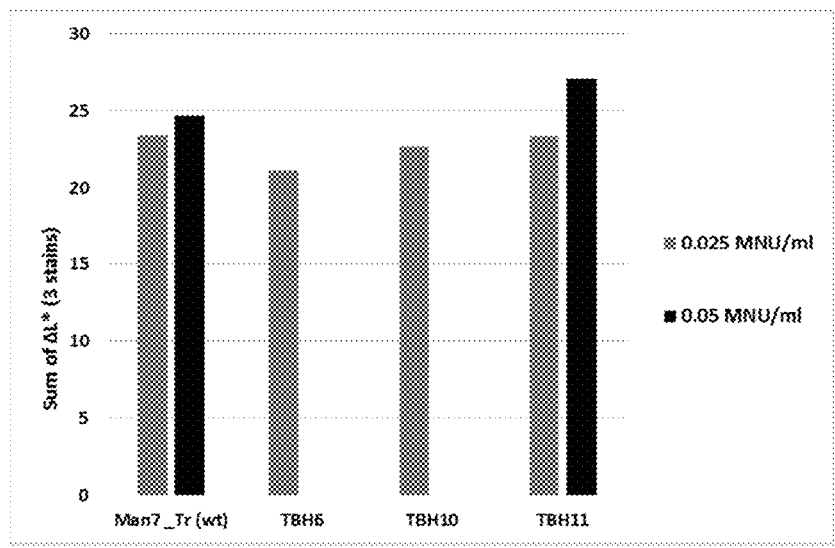
Figure 5:
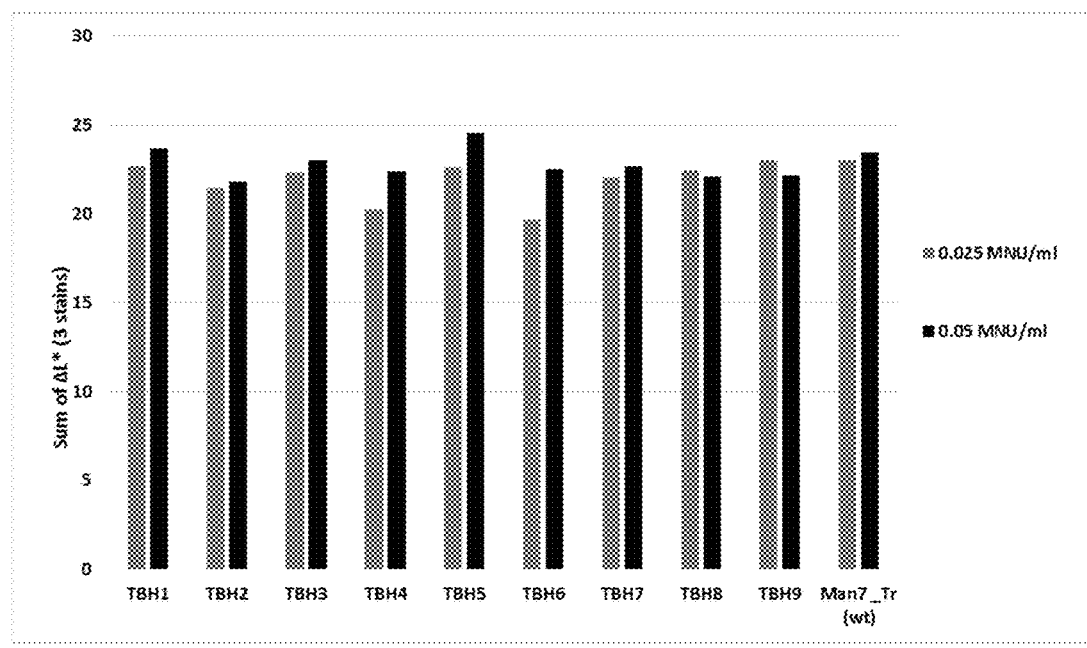
FIG. 5 describes the stain removal performance of variants TBH1, TBH2, TBH3, TBH4, TBH5, TBH6, TBH7, TBH8, TBH9 and wild type Man7 (produced in *Trichoderma*) as an increase of lightness (sum of ΔL*of 3 stains) in the presence of 3.8 g/l of Commercial bleach detergent powder at 40° C., 16° dH, 60 min, pH approx. 9.5 and enzymes dosed as activity units (MNU) per wash liquor.

The results obtained with commercial liquid detergent are shown in FIG. 3, the results with commercial color detergent powder in FIG. 4 and the results with commercial bleach detergent in FIG. 5. All variants (TBH1-TBH11) showed excellent stain removal performance with commercial detergents of different types. Performance of variants was similar to the wild type.

Example 7

Stain Removal Performance of Mannanase Variants Produced in *Bacillus* with Commercial Detergent Cultivation supernatants of variants BH18, BH21, BH23, BH24 and BH25 produced in *Bacillus* (as described in Example 3) were tested for their ability to remove mannanase sensitive standard stains at 40° C. and water hardness of 16° dH with commercial detergents and compared to wild type enzyme. Similar test system than described in Example 6 was used.

Figure 6:
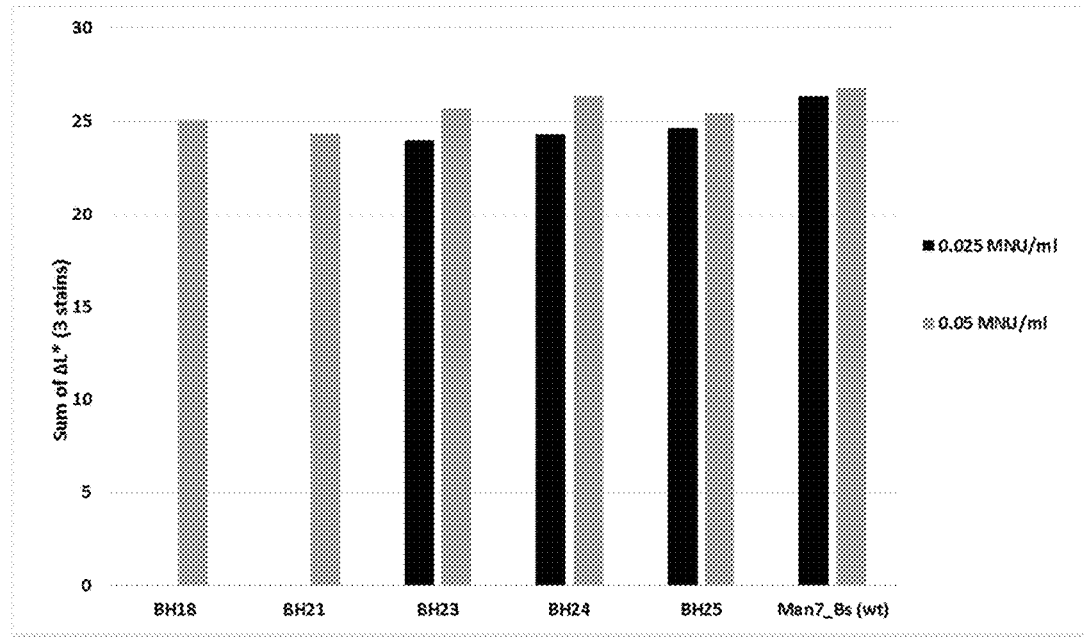
FIG. 6 describes the stain removal performance of variants BH18, BH21, BH23, BH24, BH25 and wild type Man7 (produced in *Bacillus*) as an increase of lightness (sum of ΔL*of 3 stains) in the presence of 4.4 g/l of Commercial heavy duty liquid detergent A at 40° C., 16° dH, 60 min, pH approx. 8.3 and enzymes dosed as activity units (MNU) per wash liquor.
Figure 7:
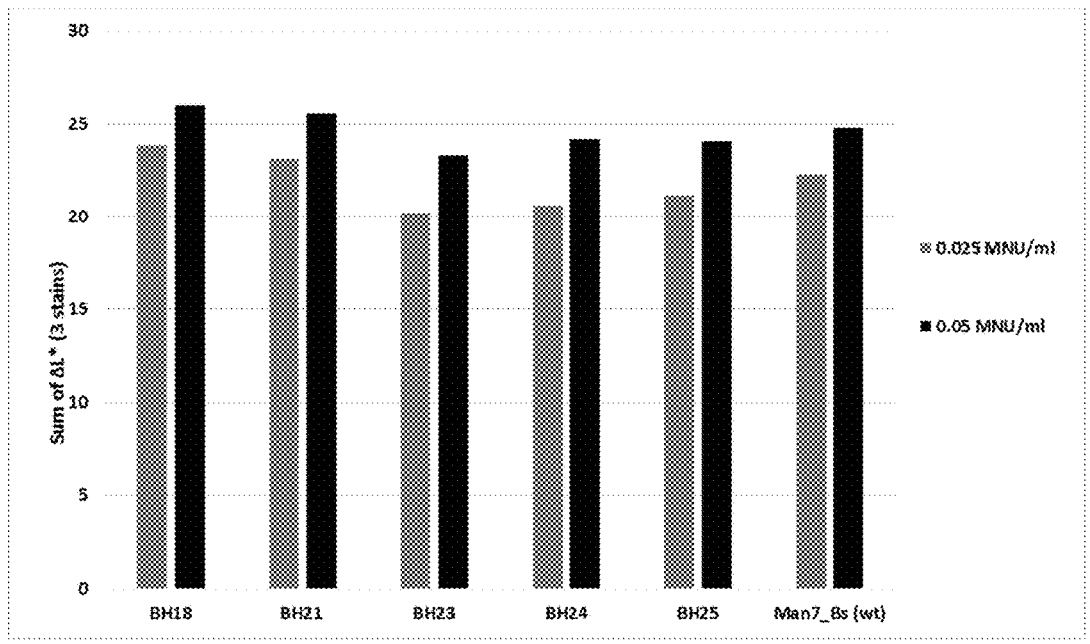
FIG. 7 describes the stain removal performance of variants BH18, BH21, BH23, BH24, BH25 and wild type Man7 (produced in *Bacillus*) as an increase of lightness (sum of ΔL*of 3 stains) in the presence of 3.8 g/l of Commercial color detergent powder at 40° C., 16° dH, 60 min, pH approx. 10 and enzymes dosed as activity units (MNU) per wash liquor.
Figure 8:
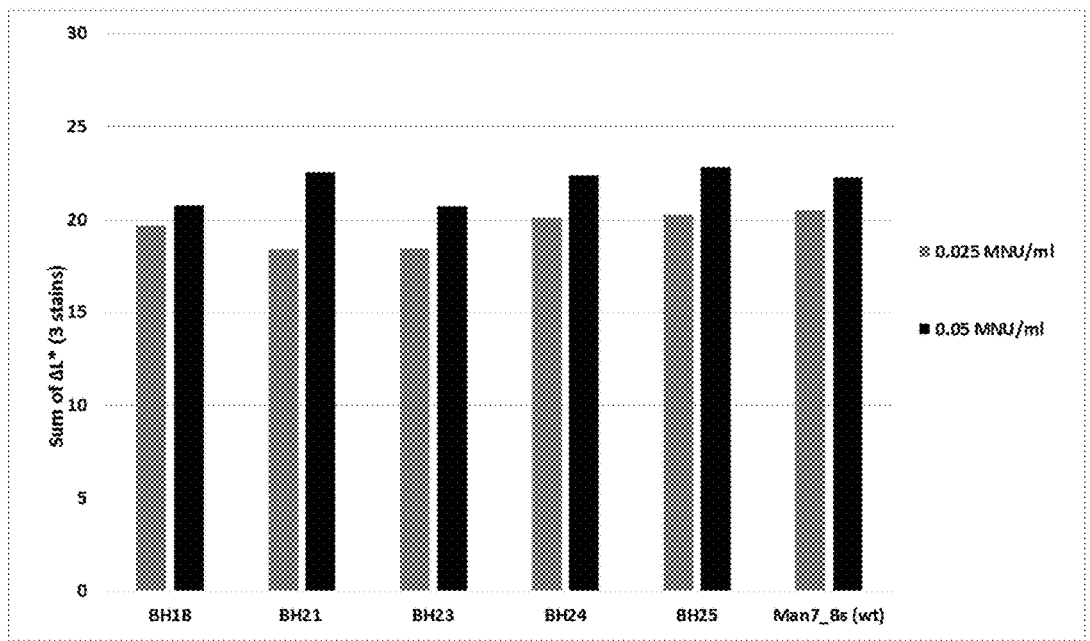
FIG. 8 describes the stain removal performance of variants BH18, BH21, BH23, BH24, BH25 and wild type Man7 (produced in *Bacillus*) as an increase of lightness (sum of ΔL*of 3 stains) in the presence of 3.8 g/l of Commercial bleach detergent powder at 40° C., 16° dH, 60 min, pH approx. 9.5 and enzymes dosed as activity units (MNU) per wash liquor.

The results obtained with commercial liquid detergent are shown in FIG. 6, the results with commercial color detergent powder in FIGS. 7 and the results with commercial bleach detergent in FIG. 8. All variants (BH18, BH21, BH23, BH24, BH25) showed excellent stain removal performance with commercial detergents of different types. Performance of variants was similar to wild the type.

Example 8

Stability of Mannanase Variants in Commercial Liquid Detergent at 37° C.

The stability of cultivation supernatants of several mannanase variants produced in *Trichoderma* (as described in Example 4) or *Bacillus* (as described in Example 3) was tested in commercial liquid heavy duty detergent A containing protease and all other enzymes except mannanase and compared to the wild type enzymes. Mannanase preparations were added 4 w/w-% in detergent and samples were incubated in plastic tubes with caps at 37° C. for about 16 or 24 weeks. The activity was measured at certain intervals by activity assay described in Example 5 except using 30 min incubation time. Results were calculated as residual activity (%), which was obtained by dividing the activity of a sample taken at certain time point by initial activity of the sample.

Figure 9:
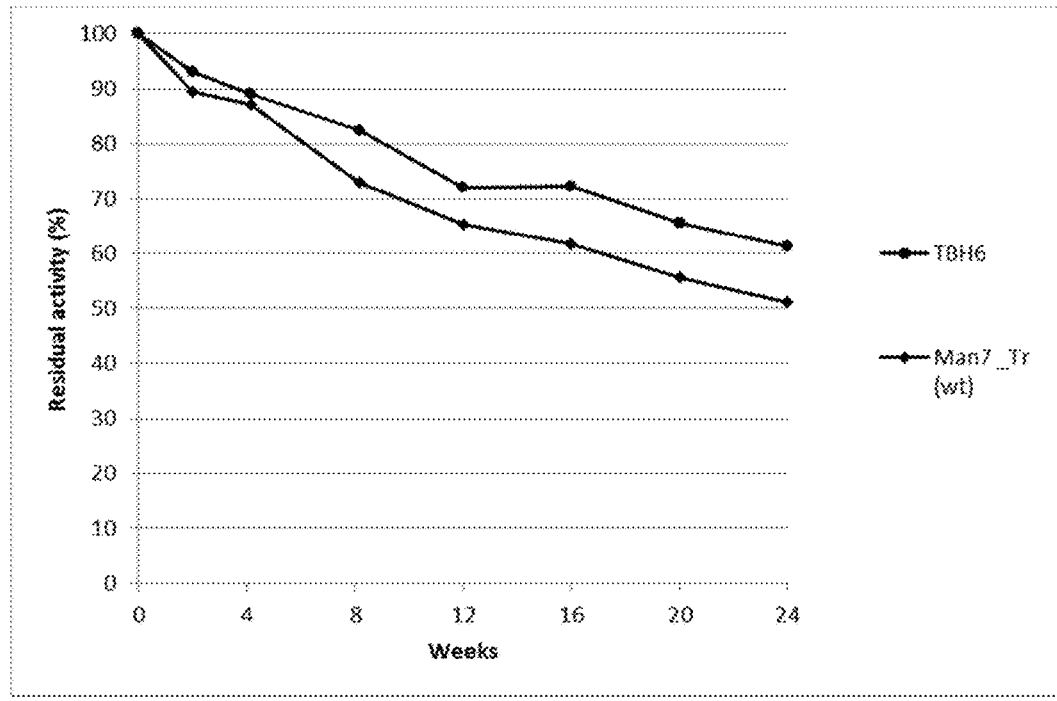
FIG. 9 shows the stability of variant TBH6 in Commercial heavy duty liquid detergent at 37° C. compared to wild type enzyme produced in *Trichoderma*.

The stability of variants TBH2, TBH3, TBH4, TBH5 and especially TBH6 was improved compared to the wild type enzyme of Man7 produced in *Trichoderma*, when stored at high temperature like 37° C. for 24 weeks. Results of stability tests with TBH6 compared to wild type are shown in FIG. 9.

Figure 10:
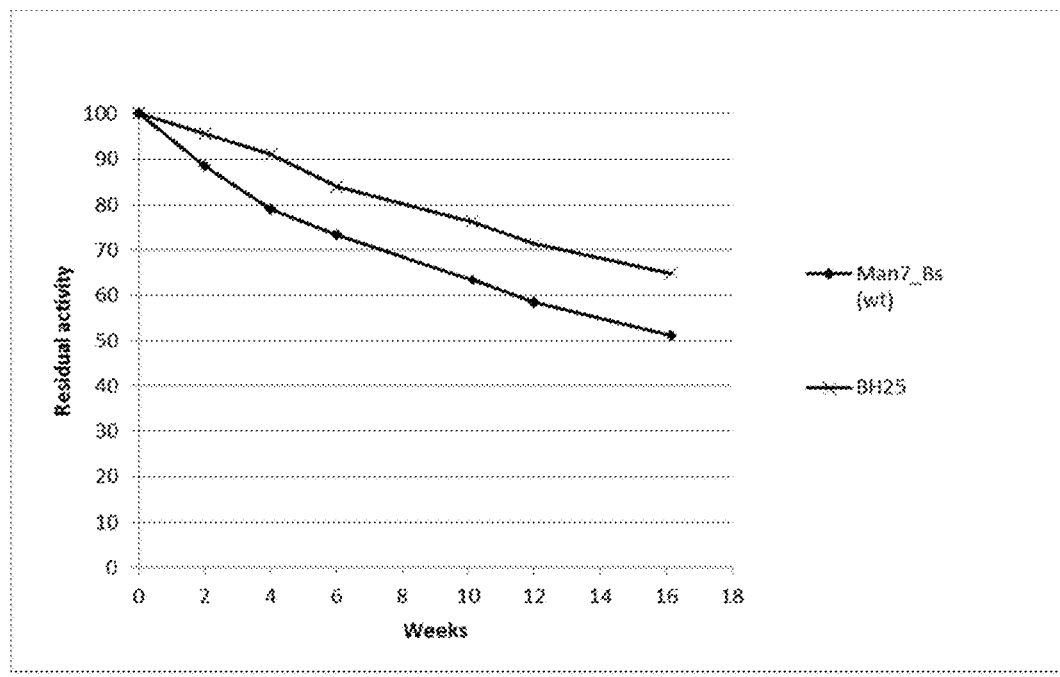
FIG. 10 shows the stability of variant BH25 in Commercial heavy duty liquid detergent at 37° C. compared to wild type enzyme produced in *Bacillus*.

The stability of variants BH21, BH23, BH24 and especially BH25 was improved compared to the wild type enzyme of Man7 produced in *Bacillus* when stored at high temperature like 37° C. for several weeks. Results of stability tests with BH25 compared to the wild type are shown in FIG. 10.

Example 9

Stability of Mannanase Variants in Commercial Liquid Detergent at 50° C.

The stability of cultivation supernatants of TBH1-TBH11 variants produced in *Trichoderma* (as described in Example 4) was tested in commercial liquid heavy duty detergent A containing protease but no mannanase and compared to the wild type enzyme at extreme conditions. Mannanase preparations were added 4 w/w-% in detergent and samples were incubated in plastic tubes with caps at 50° C. for 7 days. The activity was measured by activity assay described in Example X except using 30 min incubation time. Results were calculated as residual activity (%), which was obtained by dividing the activity of a sample taken at certain time point by initial activity of the sample.

Figure 11A:
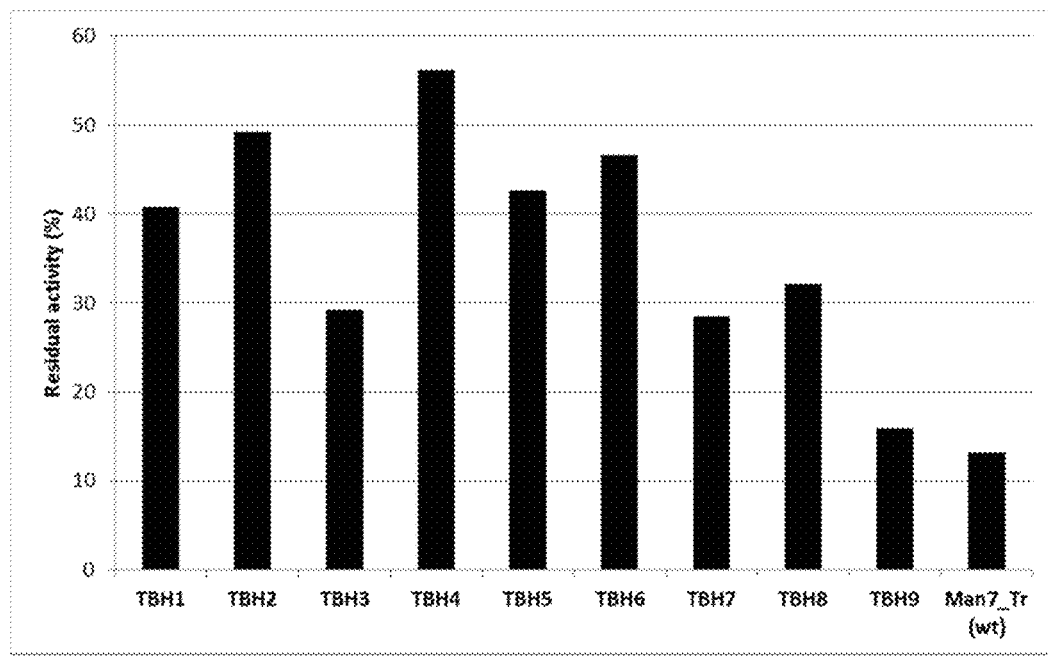
FIG. 11A-B show the stability of variants and wild type produced in *Trichoderma* in Commercial heavy duty liquid detergent at 50° C. and 7 days.
Figure 11B:
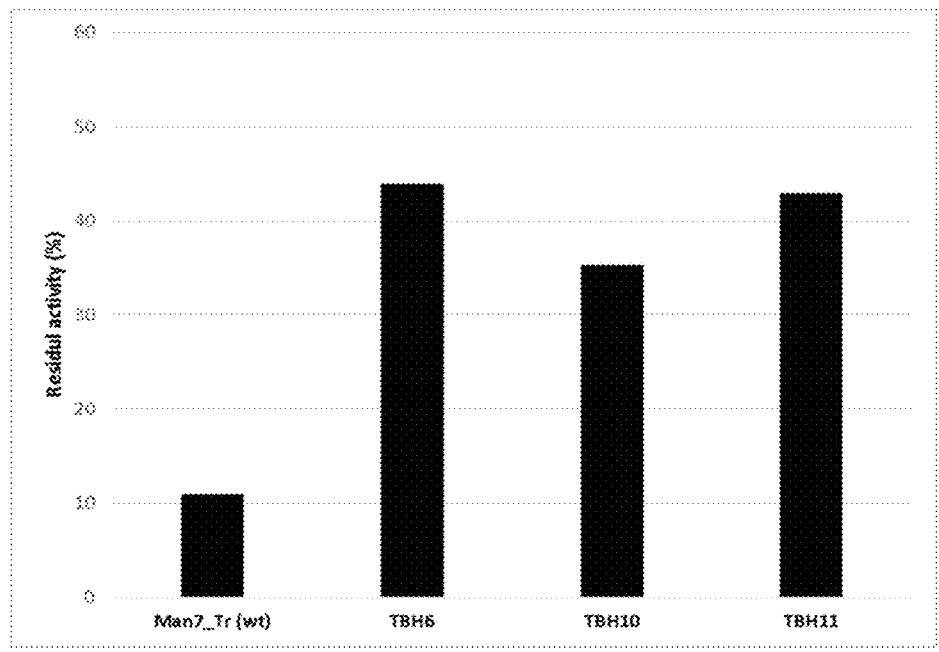

Based on the results shown in FIG. 11, the stability of all variant enzymes was better compared to the wild type at 50° C. for 7 days. The stability at extreme conditions was considerably improved especially with TBH1, TBH2, TBH4, TBH5 TBH6, TBH10 and TBH11 compared to the wild type enzyme.

Some of the best producing variants were cultivated in laboratory scale bioreactors and the stability was retested using similar test system as described above except the amount of mannanase preparation was 1 w/w-% in detergent. The stability of mannanase variants TBH5 and TBH6 was considerably better than the wild type also when laboratory scale cultivation material was used (data not shown).

The results show that mannanase variants have excellent stain removal performance and considerably improved stability compared to the wild type enzyme especially at elevated temperatures. They can also be produced more economically due to their higher specific activity and production yield (data not shown).

Example 10

Combination of Variants TBH5 and TBH6

To further improve the mannanase properties, the mutations in TBH5 and TBH6 variants are combined (M123I, A158S, G272Q, T285A, T307R and L316K). The combination variant is ordered as synthetic construct, cloned into the expression vector and produced in *Trichoderma* reesei as described in Examples 2 and 4. Stain removal performance and stability of the TBH5 and TBH6 combination variant is tested as described in Examples 6, 8 and 9. The combination variant shows excellent stain removal performance with commercial detergents of different types. Performance of the variant is similar to the wild type. The stability of the combination variant is improved compared to the wild type enzyme produced in *Trichoderma* when stored in high temperatures like 50° C. for several days.

Example 10

Efficiency Study with Mannanase Alone and in Combination with a Non-Starch Polysaccharide (NSP) Degrading Enzyme in Broilers Effects of recombinant mannanase variants of the invention are studied on growth in broilers. Ultrafiltrate of the fermentation broth including the recombinant mannanase is dried and target levels applied to a pelleted broiler diet alone or in combination with a commercial available xylanase based product.

A control diet based on corn and dehulled solvent extracted soybean meal is fed without enzyme or added by different levels of the recombinant mannanase of the invention alone or in combination with a standard dose of a commercial xy-lanase.

Initial weight of the broilers is between 30 g and 50 g. The trial lasts between three and five weeks. Each treatment consists at minimum of six replicates with 10 broilers each. In each case the diet is analysed for moisture, crude protein, crude fibre, fat, ash, and enzyme protein.

Five diets are prepared:
1) unsupplemented control (BD)
2) BD+mannanase 1-500 mg/kg
3) BD+mannanase 1-1000 mg/kg
4) BD+mannanase 1-500 mg/kg +xylanase 1-10 mg/kg
5) BD+xylanase 1-10 mg/kg Health status and mortality of the animals is checked daily by visual inspection. At days 0, 14, and 35 body weight gain (BW), feed intake (FI), and feed-conversion ratio (FCR) are measured. FCR is calculated as the total feed consumed divided by the weight gain during the same period. Determination of the effect of the recombinant mannanase variants is based on the comparison to those animals fed the same diet or the same diet but added by xylanase.

Example 11

Instant Coffee Production

Pure mannan is the main storage polysaccharide component of coffee endosperms and is responsible for their high viscosity, which negatively affects the technological processing of instant coffee and increases energy consumption during drying. Those effects are attributed to mannan forming hard, insoluble crystalline structures. β-mannanase, often together with other enzymes such as pectinase and cellulase, is added during the concentration step of instant coffee production to reduce viscosity in coffee extracts. Mannanase is also be employed for hydrolyzing galactomannans present in a liquid coffee extract in order to inhibit gel formation during freeze drying of instant coffee. Furthermore, due to the use of enzymatic treatment the coffee bean extracts can be concentrated by a low cost procedure such as evaporation.

Figure 12:
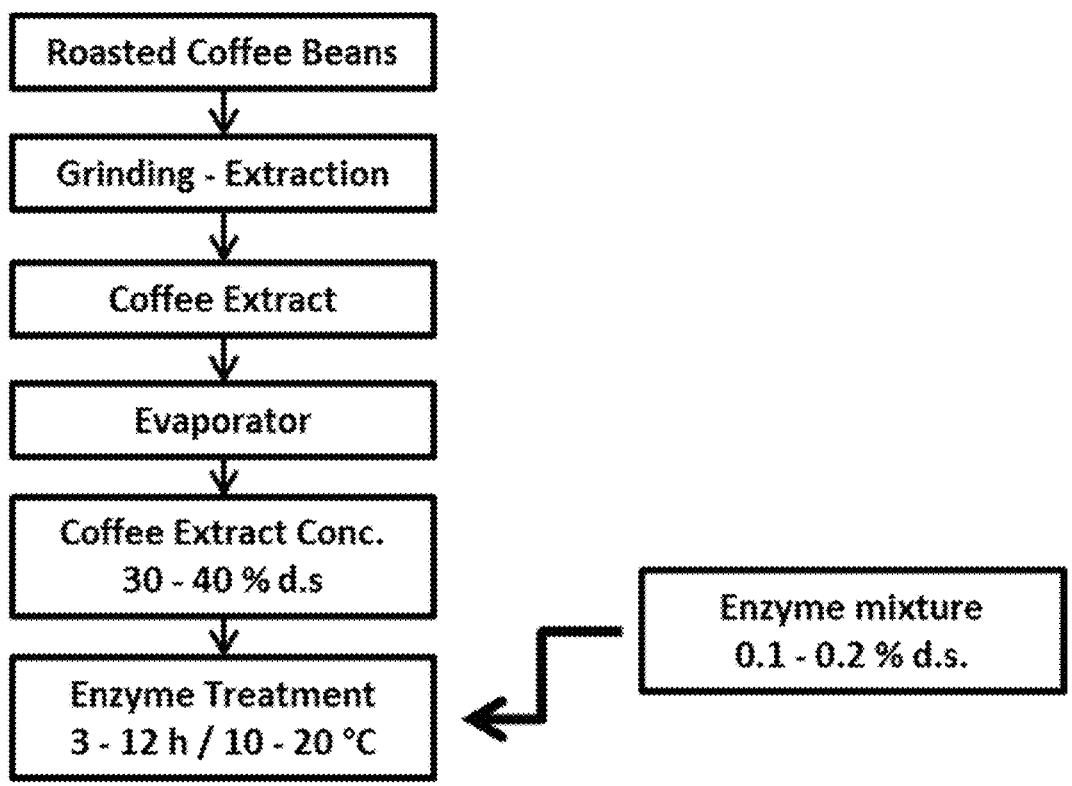
FIG. 12 shows a flow chart of instant coffee production involving use of the mannanase variants of the invention.

The test is performed according the following flow-chart of FIG. 12 at temperatures of 10° C. and an enzyme dosage of 0.15% d.s.

Mannanase variants of the invention are tested in mixture composed of different enzymes, such as pectinases and cellulases.

The viscosity of the coffee extract increases significantly over time under standard process conditions. However, the viscosity is significantly reduced using the enzyme mixture containing the mannanase variants of the invention resulting an improved downstream processing such as spray- or freeze drying.

Example 12

Pineapple Processing

In particular, mannanase is useful for pineapple mill juice extraction and clarification, as pineapple contains a large fraction of mannans, including glucomannans and galactomannans.

Mannanase helps to improve extraction of valuable fruit components, lower the viscosity of fruit juice prior to concentration, and increase filtration rate and stability of the final product.

The pineapples are crushed in a meat grinder and fill 500 g mash in a 1000 ml beaker. The enzyme is applied at 21° C. with a reaction time of 60 minutes. The mash is then pressed with a small Hafico press according to the press protocol: 0 bar 2 min-50 bar 2 min-100 bar 2 min-150 bar 2 min-200 bar 1 min-300 bar 1 min-400 bar 1min. The obtained juice is then centrifuged at 4500 rpm for 5 minutes and analyzed for turbidity and viscosity.

Mannanase variants of the invention are tested in enzyme mixtures A, B and C (Table 7).

The enzymes are first diluted with tab water before being added to the pineapple mash

TABLE 7

| Enzyme mixtures | | | |
|---|---|---|---|
| | Enzyme activity | Dosage [ppm] | 5 ml of [% enzyme solution] |
| blank | | | 5 ml H2O |
| Mixture A | Pectinase | 50 | 0.50% |
| Mixture B | Pectinase + Arabanase | 50 | 0.50% |
| Mixture C | Pectinase + Mannanase | 50 | 0.50% |

Applying mannanase variants of the invention leads to increased yield and lower turbidity of juice in pineapple processing.

Example 13

Mannanase Treatment of Soya Beans for Soya Milk Production

For the enzymatic treatment of soya beans to get soya milk the "hot process" is commonly used. For the hot soya milk process the dried soya beans were mixed and crushed in a mixer with boiling tap water in a ratio of 1:7 (soaked beans: water). The whole soya slurry is cooled down to 50-55° C. before enzyme addition. The pH level for the soya slurry should be around pH 6.5 and can be adjusted with $NaHCO_3$. The mannanase enzyme is dosed at 1 kg/t of dried soya beans into the slurry and stirred for 30 min. After completion of the reaction time, the slurry is pressed using a laboratory press to obtain the final product: soya milk. In order to ensure the same pressing profile, the pressure as well as the corresponding pressing time is specified, as shown in Table 8. Besides the sample for enzymatic reaction, a control sample without any enzyme is prepared, in which the enzyme solution was replaced with water.

TABLE 8

| Press scheme | | | | |
|---|---|---|---|---|
| | pressure [bar] | | | |
| | 0 | 50 | 100 | 300 |
| time [min] | 2 | 2 | 2 | 1 |

After pressing the soya milk is heated in a microwave until boiling to stop the enzyme reaction. Analysis of the soya milk:
- Yield in gram/time
- ° Brix, which gives a direct correlation of the amount of sugar in the soy milk, is determined with a refractometer
- The turbidity of the juice is measured with a NTU-photometer, which measures the nephelometric turbidity.
- The brightness will be measured with a LAB-measurement
- Protein content is determined with a CN-Analyser (combustion method)
- Flavour Soya milk treated with the mannanase variants of the invention shows a increased yield, brighter colour, increased ° Brix, a lower turbidity, a higher protein content and a better taste (off flavour removal).

Without limiting the scope and interpretation of the patent claims, certain technical effects of one or more of the aspects or embodiments disclosed herein are listed in the following: A technical effect is degradation or modification of mannan. Another technical effect is provision of mannanase which has good storage stability.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means without deviating from the characteristics of the invention.

Furthermore, some of the features of the above-disclosed aspects and embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

In an embodiment at least one component of the compositions of the invention has a different chemical, structural or physical characteristic compared to the corresponding natural component from which the at least one component is derived from. In an embodiment said characteristic is at least one of uniform size, homogeneous dispersion, different isoform, different codon degeneracy, different post-translational modification, different methylation, different tertiary or quaternary structure, different enzyme activity, different affinity, different binding activity, and different immunogenicity.

REFERENCES

Bendtsen J D, Nielsen H, von Heijne G, and Brunak S. (2004) Improved prediction of signal peptides: SignalP 3.0. J. Mol.Biol. 340:783-795.

Joutsjoki W, Torkkeli T K, and Nevalainen K M H. (1993) Transformation of *Trichoderma reesei* with the *Hormoconis resinae* glucoamylase P (gamP) gene: production of a heterologous glucoamylase by *Trichoderma reesei*. Curr. Genet. 24: 223-228.

Karhunen T, Mäntylä M, Nevalainen K M H, and Suominen P L. (1993) High frequency one-step gene replacement in *Trichoderma reesei*. I. Endoglucanase I overproduction. Mol. Gen. Genet. 241: 515-522.

Kunkel, T. A. (1985): Rapid and efficient site-specific mutagenesis without phenotypic selection. In Proc Natl Acad Sci USA 82 (2), pp. 488-492.

Nielsen H, Engelbrecht J, Brunak S, and von Heijne G. (1997) Identification of prokaryotic and eykaryotic signal peptides and prediction of their cleavage sites. Protein. Eng. 10: 1-6.

Nielsen H, and Krogh A. (1998) Prediction of signal peptides and signal anchors by a hidden Markov model. In: Proceedings of the Sixth International Conference on Intelligent Systems for Molecular Biology (ISMB 6), AAAI Press, Menlo Park, Calif., p. 122-130.

Paloheimo M, Mäntylä A, Kallio J, and Suominen P. (2003) Highyield production of a bacterial xylanase in the filamentous fungus *Trichoderma reesei* requires a carrier polypeptide with an intact domain structure. Appl. Env. Microbiol. 69: 7073-7082.

Penttilä M, Nevalainen H, Rättö M, Salminen E, and Knowles J. (1987) A versatile transformation system for the cellulolytic filamentous fungus *Trichoderma reesei*. Gene 61: 155-164.

Thompson J D, Higgins D G, Gibson T J (1994) CLUSTAL W. Improving the sensitivity of progressive multiple sequence alignment through sequence weighting, position-specific gap penalties and weight matrix choice. Nucleic Acids Research 22 (22): 4673-4680. DOI: 10.1093/nar/22.22.4673.

Zhang, Xiao-Zhou; Zhang, Y-H Percival (2011): Simple, fast and high-efficiency transformation system for directed evolution of cellulase in *Bacillus* subtilis. In *Microb Bio-technol* 4 (1), pp. 98-105. DOI: 10.1111/j.1751-7915.2010.00230.x.

The invention claimed is:

1. A variant of mannanase comprising at least one substitution of an amino acid at a position corresponding to the position 123, 158, 180, 272, 307, or 316 wherein the variant has mannanase activity and is selected from the group consisting of
   1) a polypeptide having at least 85% sequence identity to residues 27-331 of SEQ ID NO: 2;
   2) a variant encoded by a polynucleotide that hybridizes under high stringency conditions with
      a) nucleotides 79-993 of SEQ ID NO: 1 (man 7) or
      b) the full-length complement of a); and
   3) a variant encoded by a polynucleotide having at least 95% sequence identity to the SEQ ID NO: 1;
and wherein the amino acid numbering corresponds to the amino acid numbering of SEQ ID NO: 2 full length amino acid sequence containing a signal sequence; and wherein the variant comprises at least one additional substitution selected from:
   a substitution which prevents glycosylation of N283;or
   a substitution of 283 or 285; or
   a substitution of N283, T285, or S285; or
   a substitution of T285, or S285 to a residue other than T or S; or
   a substitution of T285, or S285 to the residue A.

2. The variant of claim 1 comprising at least one further substitution at the position M123, A158, F180, G272, T307, or L316, or a combination thereof.

3. The variant of claim 1 comprising at least one set of substitutions at the position(s):

M123 and G272; or
A158 and T307; or
L316; or
T307; or
M123, A158 and T307; or
M123 and L316; or
A158, T307, and L316; or
F180 and L316; or
M123, A158, G272; T307, and L316;
or a combination thereof.

4. The variant of claim 1 wherein the substitution results into an improved stability of the variant.

5. The variant of claim 1 wherein the additional substitution results into an altered glycosylation of the variant when produced in a host cell capable of N-linked glycosylation.

6. An enzyme composition comprising the variant of claim 1 and
   a. at least one preservative selected from organic acid, citric acid, ascorbic acid, benzoic acid and their salts and derivatives, sodium benzoate, benzoate, hydroxybenzoate and derivatives, sorbic acid, sodium sorbate, sorbate, salts, sodium chloride, potassium chloride, 1,2-Benzisothiazolin-3-one (BIT) or a combination thereof;
   b. optionally at least one stabilizer selected from polyol, propylene glycol, polyethylene glycol, hexylene glycol, glycerol, a sugar, sugar alcohol, polysaccharide, lactic acid, boric acid, boric acid derivative, aromatic borate ester, 4-formylphenyl boronic acid, phenyl boronic acid derivative, peptide, surfactant or a combination thereof;

c. optionally at least one enzyme selected from proteases, amylases, cellulases, lipases, xylanases, mannanases, cutinases, esterases, phytases, DNAses, pectinases, pectinolytic enzymes, pectate lyases, carbohydrases, arabinases, galactanases, xanthanases, xyloglucanases, laccases, peroxidases and oxidases with or without a mediator, or a combination thereof; and d. optionally at least one filler selected from maltodextrin, flour, sodium chloride, sulfate, sodium sulfate, or a combination thereof.

7. The enzyme composition of claim 6 in the form of a liquid composition, solid composition, solution, dispersion, paste, powder, granule, granulate, coated granulate, tablet, cake, crystal, crystal slurry, gel, or pellet.

8. A detergent composition comprising the variant of mannanase of claim 1.

9. The detergent composition of claim 8 in the form of a liquid detergent, solid detergent, a bar, a homogenous tablet, a tablet having two or more layers, a pouch having one or more compartments, a regular or compact powder, a granule, a granulate, a paste, a gel, or a regular, compact or concentrated liquid.

10. The detergent composition of claim 8 further comprising one or more additional enzymes selected from the group consisting of protease, lipase, cutinase, amylase, carbohydrase, cellulase, pectinase, pectatelyase, pectinolytic enzyme, esterase, mannanase, arabinase, galactanase, xylanase, oxidase, xanthanase, xyloglucanase, laccase, DNAse and/or peroxidase.

11. A method for degrading or modifying mannan containing material comprising treating said mannan containing material with an effective amount of the enzyme composition of claim 6.

12. The method of claim 11 wherein the mannan containing material is plant based material, textile, waste water, sewage, oil, or a combination thereof.

13. An animal feed comprising the enzyme composition of claim 6, and at least one protein source of plant origin or a mannan containing product or by-product, and a. Optionally at least one enzyme selected from protease, amylase, phytase, xylanase, endoglucanase, beta-glucanase, or a combination thereof; and b. Optionally at least one filler selected from maltodextrin, flour, salt, sodium chloride, sulfate, sodium sulfate, or a combination thereof.

14. A feed supplement comprising the enzyme composition of claim 6; and a. Optionally at least one enzyme selected from protease, amylase, phytase, xylanase, endoglucanase, beta-glucanase, or a combination thereof; and b. Optionally at least one filler selected from maltodextrin, flour, salt, sodium chloride, sulfate, sodium sulfate or a combination thereof.

15. A recombinant host cell comprising genetic elements that allow producing at least one recombinant polypeptide comprising the variant of claim 1.

16. The recombinant host cell of 15, wherein the host cell is selected from the group consisting of:

fungal cells, filamentous fungal cells from Division Ascomycota, Subdivision Pezizomycotina; from the group consisting of members of the Class Sordariomycetes, Subclass Hypocreomycetidae, Orders Hypocreales and Microascales and Aspergillus, Chrysosporium, Myceliophthora and Humicola;

Families Hypocreacea, Nectriaceae, Clavicipitaceae, Microascaceae, and Genera *Trichoderma* (anamorph of *Hypocrea*), *Fusarium, Gibberella, Nectria, Stachybotrys, Claviceps, Metarhizium, Villosiclava, Ophiocordyceps, Cephalosporium,* and *Scedosporium;*

*Trichoderma reesei* (Hypocrea jecorina), *T. citrinoviridae, T. longibrachiatum, T. virens, T. harzianum, T. asperellum, T. atroviridae, T. parareesei, Fusarium oxysporum, F. gramineanum, F. pseudograminearum, F. venenatum, Gibberella fujikuroi, G. monihformis, G. zeaea, Nectria* (Haematonectria) *haematococca, Stachybotrys chartarum, S. chlorohalonata, Claviceps purpurea, Metarhizium acridum, M. anisopliae, Villosiclava virens, Ophiocordyceps sinensis, Acremonium (Cephalosporium) chrysogenum,* and *Scedosporium apiospermum,* and *Aspergillus niger, Aspergillus awamori, Aspergillus oryzae, Chrysosporium lucknowense, Mycellophthora thermophila, Humicola insolens,* and *Humicola grisea,* bacterial cells, gram positive Bacilli *B. subtilis, B. licheniformis, B. megaterium, B. amyloliquefaciens, B. pumilus,* gram negative bacteria, *Escherichia coli,* actinomycetales, *Streptomyces* sp., and yeasts, *Saccharomyces cerevisiae, Pichia pastoris, Yarrowia lipolytica,*

*Trichoderma reesei* or *Bacillus.*

17. The recombinant host cell of claims 15, wherein the recombinant polypeptide is a fusion protein which, in addition to having the amino acid sequence having mannanase activity, comprises at least one of:

an amino acid sequence providing a secretory signal sequence;

an amino acid sequence which facilitates purification, or is an affinity tag or His-tag;

an amino acid sequence which is a carrier or CBM;

an amino acid sequence having an enzyme activity; and an amino acid sequence providing for the fusion protein with binding affinity, or a carbohydrate binding moiety.

18. A method for producing a recombinant polypeptide comprising a variant of mannanase comprising:

a. cultivating a recombinant host cell of claim 15, wherein the genetic elements comprise at least one control sequence which controls the production of the recombinant polypeptide in the recombinant host cell;

the genetic elements optionally comprise at least one sequence encoding a signal sequence for transporting the recombinant polypeptide outside the host cell; and cultivating is carried out in conditions allowing production of the recombinant polypeptide; and b. recovering the recombinant polypeptide.

19. A process of controlling viscosity of a drilling fluid in oil drilling or hydro-fracturing, comprising providing a composition comprising the variant of claim 1 in contact with the drilling fluid.

20. A process of controlling viscosity in manufacturing of coffee extract, fruit juice, pineapple juice, or soya milk, comprising providing a composition comprising the variant of claim 1 in contact with the coffee extract, fruit milk or soya milk.

* * * * *

SEQUENCE LISTING

<160> NUMBER OF SEQ ID NOS: 48

<210> SEQ ID NO 1
<211> LENGTH: 1395
<212> TYPE: DNA
<213> ORGANISM: Bacillus hemicellulosilyticus

<400> SEQUENCE: 1

```
cagacccact cgggcttcta catcgagggc tcgacgctct acgacgctaa cggcgagcct      60
tttgtcatgc gcggcatcaa ccacggccac gcctggtaca agcacgactc caacgtcgct     120
atccctgcta tcgctaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggct ccaacagcat ggccgacctc     300
aaccgcgccg tcgactactg gatcgagatg aaggacgccc tgatcggcaa ggaagaccgc     360
gtcatcatca acatcgctaa cgagtggtac ggcgcttggg acggccaggg ctgggccaac     420
ggctacaagg aagtcatccc tcgcctgcgc aacgctggct tcacccacac cctcatggtc     480
gacgctgccg ctggggccca gtaccctcag agcatccacg actacggcca agaggtcttc     540
aacgccgacc ctctggccaa caccatgttc tccatccaca tgtacgagta cgctggcggc     600
aacgcctcca tggtccagag caacatcgac ggcgtcgtcg accagggcct cgctctggtc     660
atcggcgagt tcggccacat gcacacggac ggcgacgtcg acgaggctac catcctgagc     720
tactcgcagc agcgcggcgt cggctggctg gcctggtcgt ggaagggcaa cggcaccccag     780 tgggagtacc tcgacctgag ctacgactgg cagggcacca acctcacgtc gtggggcaac     840
acgatcgtcc acgccctaa cggcctcctg gagacgtcca tcccttccag catctttcac     900
accgctccta caacggcga ccctcctccc cacaacggca cgagacgat cctgtacgac     960 ttcgagcacg gcacgcaggg ctggtcgggc tcgtccctgc tgggcggccc ttggaccacc    1020
aacgagtggt cgaccaacgg caaccactcc ctcaaggccg acatcttcct gtccgccaac    1080
agcaagcacg agctcgccaa ggtcgagaac cgcaacctca gcggctactc gacgctgcag    1140
gctaccgtcc gccacgctca ctggggcaac gtcggcaacc tgacggctcg catgtacgtc    1200
aagacgggca gcaactactc gtggttcaac ggcgacccca tccctgtcaa ctcggctaac    1260
ggcaccaccg tcaccctccc tctgagctcg atccccaacc tcaacgacgt caaggagatc    1320
ggcgtcgagt tcatcggcgc tagcaacagc aacggccaga ccgccatcta cctggaccac    1380
gtcacgatcc agtaa                                                      1395
```

<210> SEQ ID NO 2
<211> LENGTH: 490
<212> TYPE: PRT
<213> ORGANISM: Bacillus hemicellulosilyticus

<400> SEQUENCE: 2

```
Met Arg Asn Phe Gly Lys Leu Ile Val Ser Ser Cys Leu Leu Phe Ser
1               5                   10                  15

Phe Phe Leu Phe Ala Ser Asp Gly His Ser Gln Thr His Ser Gly Phe
                20                  25                  30

Tyr Ile Glu Gly Ser Thr Leu Tyr Asp Ala Asn Gly Glu Pro Phe Val
            35                  40                  45

Met Arg Gly Ile Asn His Gly His Ala Trp Tyr Lys His Asp Ser Asn
        50                  55                  60

Val Ala Ile Pro Ala Ile Ala Asn Gln Gly Ala Asn Thr Ile Arg Ile
```

-continued

```
                65                  70                  75                  80
        Val Leu Ser Asp Gly Gly Gln Trp Ala Lys Asp Asp Ile Asn Thr Leu
                        85                  90                  95
        Asn Gln Val Leu Asp Leu Ala Glu Glu His Glu Met Ile Ala Val Val
                        100                 105                 110
        Glu Val His Asp Ala Thr Gly Ser Asn Ser Met Ala Asp Leu Asn Arg
                        115                 120                 125
        Ala Val Asp Tyr Trp Ile Glu Met Lys Asp Ala Leu Ile Gly Lys Glu
                        130                 135                 140
        Asp Arg Val Ile Ile Asn Ile Ala Asn Glu Trp Tyr Gly Ala Trp Asp
        145                 150                 155                 160
        Gly Gln Gly Trp Ala Asn Gly Tyr Lys Glu Val Ile Pro Arg Leu Arg
                        165                 170                 175
        Asn Ala Gly Phe Thr His Thr Leu Met Val Asp Ala Ala Gly Trp Gly
                        180                 185                 190
        Gln Tyr Pro Gln Ser Ile His Asp Tyr Gly Gln Glu Val Phe Asn Ala
                        195                 200                 205
        Asp Pro Leu Ala Asn Thr Met Phe Ser Ile His Met Tyr Glu Tyr Ala
        210                 215                 220
        Gly Gly Asn Ala Ser Met Val Gln Ser Asn Ile Asp Gly Val Val Asp
        225                 230                 235                 240
        Gln Gly Leu Ala Leu Val Ile Gly Glu Phe Gly His Met His Thr Asp
                        245                 250                 255
        Gly Asp Val Asp Glu Ala Thr Ile Leu Ser Tyr Ser Gln Gln Arg Gly
                        260                 265                 270
        Val Gly Trp Leu Ala Trp Ser Trp Lys Gly Asn Gly Thr Gln Trp Glu
                        275                 280                 285
        Tyr Leu Asp Leu Ser Tyr Asp Trp Gln Gly Thr Asn Leu Thr Ser Trp
                        290                 295                 300
        Gly Asn Thr Ile Val His Gly Pro Asn Gly Leu Leu Glu Thr Ser Ile
        305                 310                 315                 320
        Pro Ser Ser Ile Phe His Thr Ala Pro Asn Asn Gly Asp Pro Pro Pro
                        325                 330                 335
        His Asn Gly Asn Glu Thr Ile Leu Tyr Asp Phe Glu His Gly Thr Gln
                        340                 345                 350
        Gly Trp Ser Gly Ser Ser Leu Leu Gly Gly Pro Trp Thr Thr Asn Glu
                        355                 360                 365
        Trp Ser Thr Asn Gly Asn His Ser Leu Lys Ala Asp Ile Phe Leu Ser
                        370                 375                 380
        Ala Asn Ser Lys His Glu Leu Ala Lys Val Glu Asn Arg Asn Leu Ser
        385                 390                 395                 400
        Gly Tyr Ser Thr Leu Gln Ala Thr Val Arg His Ala His Trp Gly Asn
                        405                 410                 415
        Val Gly Asn Leu Thr Ala Arg Met Tyr Val Lys Thr Gly Ser Asn Tyr
                        420                 425                 430
        Ser Trp Phe Asn Gly Asp Pro Ile Pro Val Asn Ser Ala Asn Gly Thr
                        435                 440                 445
        Thr Val Thr Leu Pro Leu Ser Ser Ile Pro Asn Leu Asn Asp Val Lys
                        450                 455                 460
        Glu Ile Gly Val Glu Phe Ile Gly Ala Ser Asn Ser Asn Gly Gln Thr
        465                 470                 475                 480
        Ala Ile Tyr Leu Asp His Val Thr Ile Gln
                        485                 490
```

<210> SEQ ID NO 3
<211> LENGTH: 464
<212> TYPE: PRT
<213> ORGANISM: Bacillus hemicellulosilyticus

<400> SEQUENCE: 3

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125

Trp Tyr Gly Ala Trp Asp Gly Gln Gly Trp Ala Asn Gly Tyr Lys Glu
    130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ser Met Val Gln Ser Asn
        195                 200                 205

Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Thr Gln Trp Glu Tyr Leu Asp Leu Ser Tyr Asp Trp Gln Gly
            260                 265                 270

Thr Asn Leu Thr Ser Trp Gly Asn Thr Ile Val His Gly Pro Asn Gly
        275                 280                 285

Leu Leu Glu Thr Ser Ile Pro Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
```

```
              370                 375                 380
His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
                420                 425                 430

Asn Leu Asn Asp Val Lys Glu Ile Gly Val Glu Phe Ile Gly Ala Ser
                435                 440                 445

Asn Ser Asn Gly Gln Thr Ala Ile Tyr Leu Asp His Val Thr Ile Gln
                450                 455                 460

<210> SEQ ID NO 4
<211> LENGTH: 305
<212> TYPE: PRT
<213> ORGANISM: Artificial Sequence
<220> FEATURE:
<223> OTHER INFORMATION: variant

<400> SEQUENCE: 4

Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
                20                  25                  30

Tyr Lys His Asp Ser Asn Val Ala Ile Pro Ala Ile Ala Asn Gln Gly
            35                  40                  45

Ala Asn Thr Ile Arg Ile Val Leu Ser Asp Gly Gly Gln Trp Ala Lys
50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
                100                 105                 110

Ala Leu Ile Gly Lys Glu Asp Arg Val Ile Ile Asn Ile Ala Asn Glu
            115                 120                 125

Trp Tyr Gly Ala Trp Asp Gly Gln Gly Trp Ala Asn Gly Tyr Lys Glu
130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
                180                 185                 190

His Met Tyr Glu Tyr Ala Gly Gly Asn Ala Ser Met Val Gln Ser Asn
            195                 200                 205

Ile Asp Gly Val Val Asp Gln Gly Leu Ala Leu Val Ile Gly Glu Phe
210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Thr Gln Trp Glu Tyr Leu Asp Leu Ser Tyr Asp Trp Gln Gly
                260                 265                 270

Thr Asn Leu Thr Ser Trp Gly Asn Thr Ile Val His Gly Pro Asn Gly
```

```
                275                 280                 285
Leu Leu Glu Thr Ser Ile Pro Ser Ser Ile Phe His Thr Ala Pro Asn
    290                 295                 300

Asn
305
```

<210> SEQ ID NO 5
<211> LENGTH: 1395
<212> TYPE: DNA
<213> ORGANISM: Artificial Sequence
<220> FEATURE:
<223> OTHER INFORMATION: variant

<400> SEQUENCE: 5

```
cagacccact ccggcttcta catcgagggc agcacgctct acgacgctaa cggcgagcct      60
tttgtcatgc gcggcatcaa ccacggccac gcctggtaca agcacgactc caacgtcgcc     120
atccctgcta tcgccaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggca gcaactcgat cgccgacctc     300
aaccgcgccg tcgactactg gatcgagatg aaggacgccc tgatcggcaa ggaagaccgc     360
gtcatcatca acatcgccaa cgagtggtac ggcgcttggg acggccaggg ctgggccaac     420
ggctacaagg aagtcatccc cgcctgcgc aacgctggct tcacccacac cctcatggtc     480
gacgctgctg gctggggcca gtaccccag agcatccacg actacggcca agaggtcttc     540
aacgccgacc tctggccaa caccatgttc agcatccaca tgtacgagta cgctggcggc     600
aacgctgcta tggtccagtc gaacatcgac ggcgtcgtcg accagggcct cgctctggtc     660
atcggcgagt cgccacat gcacacggac ggcgacgtcg acgaggctac catcctctcg     720
tactcgcagc agcgccaggt cggctggctc gcttggagct ggaagggcaa cggcgctcag     780
tgggagtacc tcgacctgtc gtacgactgg cagggcacca acctcacgtc ctggggcaac     840
accatcgtcc acggccctaa cggcctcctg gagacgtcga tccctagctc gatctttcac     900
accgctccta caacggcga ccctcctccc cacaacggca acgagacgat cctgtacgac     960
ttcgagcacg gcacgcaggg ctggtcgggc tccagcctgc tgggcggccc ttggaccacc    1020
aacgagtgga gcacgaacgg caaccactcg ctcaaggccg acatcttcct gagcgccaac    1080
tcgaagcacg agctcgccaa ggtcgagaac cgcaacctct cgggctactc gacgctgcag    1140
gctaccgtcc gccacgctca ctggggcaac gtcggcaacc tgacggctcg catgtacgtc    1200
aagacgggct cgaactactc ctggttcaac ggcgacccca tccctgtcaa ctcggctaac    1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                    1395
```

<210> SEQ ID NO 6
<211> LENGTH: 464
<212> TYPE: PRT
<213> ORGANISM: Artificial Sequence
<220> FEATURE:
<223> OTHER INFORMATION: variant

<400> SEQUENCE: 6

```
Gln Thr His Ser Gly Phe Tyr Ile Glu Gly Ser Thr Leu Tyr Asp Ala
1               5                   10                  15
```

-continued

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gln Trp Ala Lys
50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Ile Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125

Trp Tyr Gly Ala Trp Asp Gly Gln Gly Trp Ala Asn Gly Tyr Lys Glu
    130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Asn Ala Ala Met Val Gln Ser Asn
        195                 200                 205

Ile Asp Gly Val Val Asp Gln Gly Leu Ala Leu Val Ile Gly Glu Phe
210                 215                 220

Gly His Met His Thr Asp Gly Asp Val Asp Glu Ala Thr Ile Leu Ser
225                 230                 235                 240

Tyr Ser Gln Gln Arg Gln Val Gly Trp Leu Ala Trp Ser Trp Lys Gly
                245                 250                 255

Asn Gly Ala Gln Trp Glu Tyr Leu Asp Leu Ser Tyr Asp Trp Gln Gly
            260                 265                 270

Thr Asn Leu Thr Ser Trp Gly Asn Thr Ile Val His Gly Pro Asn Gly
        275                 280                 285

Leu Leu Glu Thr Ser Ile Pro Ser Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser

```
                435                 440                 445
Asn Ser Asn Gly Gln Thr Ala Ile Tyr Leu Asp His Val Thr Ile Gln
    450                 455                 460
```

<210> SEQ ID NO 7
<211> LENGTH: 1395
<212> TYPE: DNA
<213> ORGANISM: Artificial Sequence
<220> FEATURE:
<223> OTHER INFORMATION: variant

<400> SEQUENCE: 7

```
cagacccact ccggcttcta catcgagggc agcacgctct acgacgctaa cggcgagcct      60
tttgtcatgc gcggcatcaa ccacggccac gcctggtaca agcacgactc caacgtcgcc     120
atccctgcta tcgccaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggca gcaactcgat ggccgacctc     300
aaccgcgccg tcgactactg gatcgagatg aaggacgccc tgatcggcaa ggaagaccgc     360
gtcatcatca catcgccaa cgagtggtac ggcagctggg acggccaggg ctgggccaac     420
ggctacaagg aagtcatccc ccgcctgcgc aacgctggct cacccacac cctcatggtc      480
gacgctgctg ctggggcca gtaccccag tcgatccacg actacggcca agaggtcttc       540
aacgccgacc ctctggccaa caccatgttc agcatccaca tgtacgagta cgctggcggc     600
aacgctgcta tggtccagtc gaacatcgac ggcgtcgtcg accagggcct cgctctggtc     660
atcggcgagt tcggccacat gcacacggac ggcgacgtcg acgaggctac catcctgtcc     720
tactcgcagc agcgcggcgt cggctggctc gcttggtcgt ggaagggcaa cggcgctcag     780
tgggagtacc tcgacctgtc gtacgactgg cagggcacca acctcacctc gtggggcaac     840
cgcatcgtcc acggcctaa cggcctcctg gagacgtcga tccctagctc gatctttcac     900
accgctccta caacggcga ccctcctccc cacaacggca acgagacgat cctgtacgac     960
ttcgagcacg gcacgcaggg ctggtcgggc tccagcctgc tggcggccc ttggaccacc     1020
aacgagtgga gcaccaacgg caaccactcg ctcaaggccc acatcttcct gagcgccaac    1080
tcgaagcacg agctcgccaa ggtcgagaac cgcaacctct cgggctactc gacgctgcag    1140
gctaccgtcc gccacgctca ctgggcaac gtcggcaacc tgacggctcg catgtacgtc     1200
aagacgggct cgaactactc ctggttcaac ggcgacccca tccctgtcaa ctcggctaac    1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                      1395
```

<210> SEQ ID NO 8
<211> LENGTH: 464
<212> TYPE: PRT
<213> ORGANISM: Artificial Sequence
<220> FEATURE:
<223> OTHER INFORMATION: variant

<400> SEQUENCE: 8

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30
```

```
Tyr Lys His Asp Ser Asn Val Ala Ile Pro Ala Ile Ala Asn Gln Gly
         35                  40                  45
Ala Asn Thr Ile Arg Ile Val Leu Ser Asp Gly Gly Gln Trp Ala Lys
 50                  55                  60
Asp Asp Ile Asn Thr Leu Asn Gln Val Leu Asp Leu Ala Glu Glu His
65                  70                  75                  80
Glu Met Ile Ala Val Val Glu Val His Asp Ala Thr Gly Ser Asn Ser
                 85                  90                  95
Met Ala Asp Leu Asn Arg Ala Val Asp Tyr Trp Ile Glu Met Lys Asp
                100                 105                 110
Ala Leu Ile Gly Lys Glu Asp Arg Val Ile Ile Asn Ile Ala Asn Glu
            115                 120                 125
Trp Tyr Gly Ser Trp Asp Gly Gln Gly Trp Ala Asn Gly Tyr Lys Glu
        130                 135                 140
Val Ile Pro Arg Leu Arg Asn Ala Gly Phe Thr His Thr Leu Met Val
145                 150                 155                 160
Asp Ala Ala Gly Trp Gly Gln Tyr Pro Gln Ser Ile His Asp Tyr Gly
                165                 170                 175
Gln Glu Val Phe Asn Ala Asp Pro Leu Ala Asn Thr Met Phe Ser Ile
                180                 185                 190
His Met Tyr Glu Tyr Ala Gly Gly Asn Ala Ala Met Val Gln Ser Asn
            195                 200                 205
Ile Asp Gly Val Val Asp Gln Gly Leu Ala Leu Val Ile Gly Glu Phe
        210                 215                 220
Gly His Met His Thr Asp Gly Asp Val Asp Glu Ala Thr Ile Leu Ser
225                 230                 235                 240
Tyr Ser Gln Gln Arg Gly Val Gly Trp Leu Ala Trp Ser Trp Lys Gly
                245                 250                 255
Asn Gly Ala Gln Trp Glu Tyr Leu Asp Leu Ser Tyr Asp Trp Gln Gly
            260                 265                 270
Thr Asn Leu Thr Ser Trp Gly Asn Arg Ile Val His Gly Pro Asn Gly
        275                 280                 285
Leu Leu Glu Thr Ser Ile Pro Ser Ser Ile Phe His Thr Ala Pro Asn
290                 295                 300
Asn Gly Asp Pro Pro His Asn Gly Asn Glu Thr Ile Leu Tyr Asp
305                 310                 315                 320
Phe Glu His Gly Thr Gln Gly Trp Ser Gly Ser Leu Leu Gly Gly
                325                 330                 335
Pro Trp Thr Thr Asn Glu Trp Ser Thr Asn Gly Asn His Ser Leu Lys
            340                 345                 350
Ala Asp Ile Phe Leu Ser Ala Asn Ser Lys His Glu Leu Ala Lys Val
        355                 360                 365
Glu Asn Arg Asn Leu Ser Gly Tyr Ser Thr Leu Gln Ala Thr Val Arg
370                 375                 380
His Ala His Trp Gly Asn Val Gly Asn Leu Thr Ala Arg Met Tyr Val
385                 390                 395                 400
Lys Thr Gly Ser Asn Tyr Ser Trp Phe Asn Gly Asp Pro Ile Pro Val
                405                 410                 415
Asn Ser Ala Asn Gly Thr Thr Val Thr Leu Pro Leu Ser Ser Ile Pro
            420                 425                 430
Asn Leu Asn Asp Val Lys Glu Ile Gly Val Glu Phe Ile Gly Ala Ser
        435                 440                 445
Asn Ser Asn Gly Gln Thr Ala Ile Tyr Leu Asp His Val Thr Ile Gln
```

<210> SEQ ID NO 9
<211> LENGTH: 1395
<212> TYPE: DNA
<213> ORGANISM: Artificial Sequence
<220> FEATURE:
<223> OTHER INFORMATION: variant

<400> SEQUENCE: 9

```
cagacccact ccggcttcta catcgagggc agcacgctct acgacgctaa cggcgagcct      60
tttgtcatgc gcggcatcaa ccacggccac gcctggtaca agcacgactc caacgtcgcc     120
atccctgcta tcgccaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggca gcaactcgat ggccgacctc     300
aaccgcgccg tcgactactg gatcgagatg aaggacgccc tgatcggcaa ggaagaccgc     360
gtcatcatca acatcgccaa cgagtggtac ggcgcttggg acggccaggg ctgggccaac     420
ggctacaagg aagtcatccc cgcctgcgc aacgctggct tcacccacac cctcatggtc     480
gacgctgctg ctggggcca gtaccccag agcatccacg actacggcca agaggtcttc      540
aacgccgacc ctctcgccaa caccatgttc agcatccaca tgtacgagta cgctggcggc     600
aacgctgcta tggtccagtc gaacatcgac ggcgtcgtcg accagggcct cgctctggtc     660
atcggcgagt cggccacat gcacacggac ggcgacgtcg acgaggctac catcctgtcc      720
tactcgcagc agcgcggcgt cggctggctc gcttggagct ggaagggcaa cggcgctcag     780
tgggagtacc tcgacctgtc gtacgactgg cagggcacca acctcacgtc ctggggcaac     840
accatcgtcc acgccctaa cggcctgaag agacgtcga tccctagctc gatcttttcac     900
accgctccta acaacggcga ccctcctccc cacaacggca acgagacgat cctgtacgac     960
ttcgagcacg cacgcagggg ctggtcgggc tccagcctgc tgggcggccc ttggaccacc    1020
aacgagtgga gcacgaacgg caaccactcg ctcaaggccg acatcttcct gagcgccaac    1080
tcgaagcacg agctcgccaa ggtcgagaac cgcaacctct cgggctactc gacgctgcag    1140
gctaccgtcc gccacgctca ctggggcaac gtcggcaacc tgacggctcg catgtacgtc    1200
aagacgggct cgaactactc ctggttcaac ggcgacccca tccctgtcaa ctcggctaac    1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                    1395
```

<210> SEQ ID NO 10
<211> LENGTH: 464
<212> TYPE: PRT
<213> ORGANISM: Artificial Sequence
<220> FEATURE:
<223> OTHER INFORMATION: variant

<400> SEQUENCE: 10

```
Gln Thr His Ser Gly Phe Tyr Ile Glu Gly Ser Thr Leu Tyr Asp Ala
1               5                   10                  15
Asn Gly Glu Pro Phe Val Met Arg Gly Ile Asn His Gly His Ala Trp
            20                  25                  30
Tyr Lys His Asp Ser Asn Val Ala Ile Pro Ala Ile Ala Asn Gln Gly
        35                  40                  45
```

-continued

```
Ala Asn Thr Ile Arg Ile Val Leu Ser Asp Gly Gly Gln Trp Ala Lys
 50                  55                  60
Asp Asp Ile Asn Thr Leu Asn Gln Val Leu Asp Leu Ala Glu Glu His
 65                  70                  75                  80
Glu Met Ile Ala Val Val Glu Val His Asp Ala Thr Gly Ser Asn Ser
                 85                  90                  95
Met Ala Asp Leu Asn Arg Ala Val Asp Tyr Trp Ile Glu Met Lys Asp
            100                 105                 110
Ala Leu Ile Gly Lys Glu Asp Arg Val Ile Ile Asn Ile Ala Asn Glu
        115                 120                 125
Trp Tyr Gly Ala Trp Asp Gly Gln Gly Trp Ala Asn Gly Tyr Lys Glu
    130                 135                 140
Val Ile Pro Arg Leu Arg Asn Ala Gly Phe Thr His Thr Leu Met Val
145                 150                 155                 160
Asp Ala Ala Gly Trp Gly Gln Tyr Pro Gln Ser Ile His Asp Tyr Gly
                165                 170                 175
Gln Glu Val Phe Asn Ala Asp Pro Leu Ala Asn Thr Met Phe Ser Ile
            180                 185                 190
His Met Tyr Glu Tyr Ala Gly Gly Asn Ala Ala Met Val Gln Ser Asn
        195                 200                 205
Ile Asp Gly Val Val Asp Gln Gly Leu Ala Leu Val Ile Gly Glu Phe
    210                 215                 220
Gly His Met His Thr Asp Gly Asp Val Asp Glu Ala Thr Ile Leu Ser
225                 230                 235                 240
Tyr Ser Gln Gln Arg Gly Val Gly Trp Leu Ala Trp Ser Trp Lys Gly
                245                 250                 255
Asn Gly Ala Gln Trp Glu Tyr Leu Asp Leu Ser Tyr Asp Trp Gln Gly
            260                 265                 270
Thr Asn Leu Thr Ser Trp Gly Asn Thr Ile Val His Gly Pro Asn Gly
        275                 280                 285
Leu Lys Glu Thr Ser Ile Pro Ser Ser Ile Phe His Thr Ala Pro Asn
    290                 295                 300
Asn Gly Asp Pro Pro His Asn Gly Asn Glu Thr Ile Leu Tyr Asp
305                 310                 315                 320
Phe Glu His Gly Thr Gln Gly Trp Ser Gly Ser Ser Leu Leu Gly Gly
                325                 330                 335
Pro Trp Thr Thr Asn Glu Trp Ser Thr Asn Gly Asn His Ser Leu Lys
            340                 345                 350
Ala Asp Ile Phe Leu Ser Ala Asn Ser Lys His Glu Leu Ala Lys Val
        355                 360                 365
Glu Asn Arg Asn Leu Ser Gly Tyr Ser Thr Leu Gln Ala Thr Val Arg
    370                 375                 380
His Ala His Trp Gly Asn Val Gly Asn Leu Thr Ala Arg Met Tyr Val
385                 390                 395                 400
Lys Thr Gly Ser Asn Tyr Ser Trp Phe Asn Gly Asp Pro Ile Pro Val
                405                 410                 415
Asn Ser Ala Asn Gly Thr Thr Val Thr Leu Pro Leu Ser Ser Ile Pro
            420                 425                 430
Asn Leu Asn Asp Val Lys Glu Ile Gly Val Glu Phe Ile Gly Ala Ser
        435                 440                 445
Asn Ser Asn Gly Gln Thr Ala Ile Tyr Leu Asp His Val Thr Ile Gln
    450                 455                 460
```

<210> SEQ ID NO 11
<211> LENGTH: 1395
<212> TYPE: DNA
<213> ORGANISM: Artificial Sequence
<220> FEATURE:
<223> OTHER INFORMATION: variant

<400> SEQUENCE: 11

```
cagacccact ccggcttcta catcgagggc agcacgctct acgacgctaa cggcgagcct      60
tttgtcatgc gcggcatcaa ccacggccac gcctggtaca agcacgactc caacgtcgcc     120
atccctgcta tcgccaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggca gcaactcgat cgccgacctc     300
aaccgcgccg tcgactactg gatcgagatg aaggacgccc tgatcggcaa ggaagaccgc     360
gtcatcatca acatcgccaa cgagtggtac ggctcttggg acggccaggg ctgggccaac     420
ggctacaagg aagtcatccc cgcctgcgc aacgctggct tcacccacac cctcatggtc      480
gacgctgctg gctggggcca gtacccccag agcatccacg actacggcca agaggtcttc     540
aacgccgacc ctctggccaa caccatgttc agcatccaca tgtacgagta cgctggcggc     600
aacgctgcta tggtccagtc gaacatcgac ggcgtcgtcg accagggcct cgctctggtc     660
atcggcgagt tcggccacat gcacacggac ggcgacgtcg acgaggctac catcctctcg     720
tactcgcagc agcgccaggt cggctggctc gcttggagct ggaagggcaa cggcgctcag     780
tgggagtacc tcgacctgtc gtacgactgg cagggcacca acctcacgtc ctggggcaac     840
agaatcgtcc acggccctaa cggcctcctg gagacgtcga tccctagctc gatcttttcac    900
accgctccta caacggcga cccctcctcc cacaacggca acgagacgat cctgtacgac     960
ttcgagcacg gcacgcaggg ctggtcgggc tccagcctgc tgggcggccc ttggaccacc    1020
aacgagtgga gcacgaacgg caaccactcg ctcaaggccg acatcttcct gagcgccaac    1080
tcgaagcacg agctcgccaa ggtcgagaac cgcaacctct cgggctactc gacgctgcag    1140
gctaccgtcc gccacgctca ctggggcaac gtcggcaacc tgacggctcg catgtacgtc    1200
aagacgggct cgaactactc ctggttcaac ggcgacccca tccctgtcaa ctcggctaac    1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                     1395
```

<210> SEQ ID NO 12
<211> LENGTH: 464
<212> TYPE: PRT
<213> ORGANISM: Artificial Sequence
<220> FEATURE:
<223> OTHER INFORMATION: variant

<400> SEQUENCE: 12

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60
```

```
Asp Asp Ile Asn Thr Leu Asn Gln Val Leu Asp Leu Ala Glu Glu His
 65                  70                  75                  80

Glu Met Ile Ala Val Val Glu Val His Asp Ala Thr Gly Ser Asn Ser
             85                  90                  95

Ile Ala Asp Leu Asn Arg Ala Val Asp Tyr Trp Ile Glu Met Lys Asp
            100                 105                 110

Ala Leu Ile Gly Lys Glu Asp Arg Val Ile Asn Ile Ala Asn Glu
        115                 120                 125

Trp Tyr Gly Ser Trp Asp Gly Gln Gly Trp Ala Asn Gly Tyr Lys Glu
        130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ala Met Val Gln Ser Asn
        195                 200                 205

Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gln Val Gly Trp Leu Ala Trp Ser Trp Lys Gly
                245                 250                 255

Asn Gly Ala Gln Trp Glu Tyr Leu Asp Leu Ser Tyr Asp Trp Gln Gly
            260                 265                 270

Thr Asn Leu Thr Ser Trp Gly Asn Arg Ile Val His Gly Pro Asn Gly
        275                 280                 285

Leu Leu Glu Thr Ser Ile Pro Ser Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ile Pro
            420                 425                 430

Asn Leu Asn Asp Val Lys Glu Ile Gly Val Glu Phe Ile Gly Ala Ser
        435                 440                 445

Asn Ser Asn Gly Gln Thr Ala Ile Tyr Leu Asp His Val Thr Ile Gln
    450                 455                 460

<210> SEQ ID NO 13
<211> LENGTH: 1395
<212> TYPE: DNA
```

<213> ORGANISM: Artificial Sequence
<220> FEATURE:
<223> OTHER INFORMATION: variant

<400> SEQUENCE: 13

```
cagacccact ccggcttcta catcgagggc agcacgctct acgacgctaa cggcgagcct      60
tttgtcatgc gcggcatcaa ccacggccac gcctggtaca agcacgactc caacgtcgcc     120
atccctgcta tcgccaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggca gcaactcgat cgccgacctc     300
aaccgcgccg tcgactactg gatcgagatg aaggacgccc tgatcggcaa ggaagaccgc     360
gtcatcatca acatcgccaa cgagtggtac ggcgcttggg acggccaggg ctgggccaac     420
ggctacaagg aagtcatccc cgcctgcgc aacgctggct cacccacac cctcatggtc     480
gacgctgctg ctggggccac gtaccccccag agcatccacg actacggcca agaggtcttc     540
aacgccgacc ctctggccaa caccatgttc agcatccaca tgtacgagta cgctggcggc     600
aacgctgcta tggtccagtc gaacatcgac ggcgtcgtcg accagggcct cgctctggtc     660
atcggcgagt tcgccacat gcacacggac ggcgacgtcg acgaggctac catcctctcg     720
tactcgcagc agcgccaggt cggctggctc gcttggagct ggaagggcaa cggcgctcag     780
tgggagtacc tcgacctgtc gtacgactgg cagggcacca acctcacgtc ctggggcaac     840
accatcgtcc acggccctaa cggcctcaaa gagacgtcga tccctagctc gatctttcac     900
accgctccta caacggcga ccctcctccc cacaacggca acgagacgat cctgtacgac     960
ttcgagcacg gcacgcaggg ctggtcgggc tccagcctgc tgggcggccc ttggaccacc    1020
aacgagtgga gcacgaacgg caaccactcg ctcaaggccg acatcttcct gagcgccaac    1080
tcgaagcacg agctcgccaa ggtcgagaac cgcaacctct cgggctactc gacgctgcag    1140
gctaccgtcc gccacgctca ctgggcaac gtcggcaacc tgacggctcg catgtacgtc    1200
aagacgggct cgaactactc ctggttcaac ggcgacccca tccctgtcaa ctcggctaac    1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                     1395
```

<210> SEQ ID NO 14
<211> LENGTH: 464
<212> TYPE: PRT
<213> ORGANISM: Artificial Sequence
<220> FEATURE:
<223> OTHER INFORMATION: variant

<400> SEQUENCE: 14

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80
```

Glu Met Ile Ala Val Glu Val His Asp Ala Thr Gly Ser Asn Ser
            85                  90                  95

Ile Ala Asp Leu Asn Arg Ala Val Asp Tyr Trp Ile Glu Met Lys Asp
        100                 105                 110

Ala Leu Ile Gly Lys Glu Asp Arg Val Ile Ile Asn Ile Ala Asn Glu
        115                 120                 125

Trp Tyr Gly Ala Trp Asp Gly Gln Gly Trp Ala Asn Gly Tyr Lys Glu
        130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ala Met Val Gln Ser Asn
            195                 200                 205

Ile Asp Gly Val Val Asp Gln Gly Leu Ala Leu Val Gly Glu Phe
        210                 215                 220

Gly His Met His Thr Asp Gly Asp Val Asp Glu Ala Thr Ile Leu Ser
225                 230                 235                 240

Tyr Ser Gln Gln Arg Gln Val Gly Trp Leu Ala Trp Ser Trp Lys Gly
                245                 250                 255

Asn Gly Ala Gln Trp Glu Tyr Leu Asp Leu Ser Tyr Asp Trp Gln Gly
                260                 265                 270

Thr Asn Leu Thr Ser Trp Gly Asn Thr Ile Val His Gly Pro Asn Gly
            275                 280                 285

Leu Lys Glu Thr Ser Ile Pro Ser Ser Ile Phe His Thr Ala Pro Asn
        290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser
        435                 440                 445

Asn Ser Asn Gly Gln Thr Ala Ile Tyr Leu Asp His Val Thr Ile Gln
450                 455                 460

<210> SEQ ID NO 15
<211> LENGTH: 1395
<212> TYPE: DNA
<213> ORGANISM: Artificial Sequence
<220> FEATURE:
<223> OTHER INFORMATION: variant

<400> SEQUENCE: 15

```
cagacccact ccggcttcta catcgagggc agcacgctct acgacgctaa cggcgagcct      60
tttgtcatgc gcggcatcaa ccacggccac gcctggtaca agcacgactc caacgtcgcc     120
atccctgcta tcgccaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggca gcaactcgat ggccgacctc     300
aaccgcgccg tcgactactg gatcgagatg aaggacgccc tgatcggcaa ggaagaccgc     360
gtcatcatca catcgccaa cgagtggtac ggcagctggg acggccaggg ctgggccaac      420
ggctacaagg aagtcatccc ccgcctgcgc aacgctggct tcacccacac cctcatggtc     480
gacgctgctg gctggggcca gtaccccag tcgatccacg actacggcca agaggtcttc      540
aacgccgacc tctggccaa caccatgttc agcatccaca tgtacgagta cgctggcggc      600
aacgctgcta tggtccagtc gaacatcgac ggcgtcgtcg accagggcct cgctctggtc     660
atcggcgagt tcggccacat gcacacggac ggcgacgtcg acgaggctac catcctgtcc     720
tactcgcagc agcgcggcgt cggctggctc gcttggtcgt ggaagggcaa cggcgctcag     780
tgggagtacc tcgacctgtc gtacgactgg cagggcacca acctcacctc gtggggcaac     840
cgcatcgtcc acgccctaa cggcctcaaa gagacgtcga tccctagctc gatcttcac      900
accgctccta caacggcga ccctcctccc cacaacggca acgagacgat cctgtacgac      960
ttcgagcacg gcacgcaggg ctggtcgggc tccagcctgc tgggcggccc ttggaccacc    1020
aacgagtgga gcaccaacgg caaccactcg ctcaaggccg acatcttcct gagcgccaac    1080
tcgaagcacg agctcgccaa ggtcgagaac cgcaacctct cgggctactc gacgctgcag    1140
gctaccgtcc gccacgctca ctgggcaac gtcggcaacc tgacggctcg catgtacgtc     1200
aagacgggct cgaactactc ctggttcaac ggcgacccca tccctgtcaa ctcggctaac    1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                     1395
```

<210> SEQ ID NO 16
<211> LENGTH: 464
<212> TYPE: PRT
<213> ORGANISM: Artificial Sequence
<220> FEATURE:
<223> OTHER INFORMATION: variant

<400> SEQUENCE: 16

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95
```

Met Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125

Trp Tyr Gly Ser Trp Asp Gly Gln Gly Trp Ala Asn Gly Tyr Lys Glu
    130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ala Met Val Gln Ser Asn
        195                 200                 205

Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Ala Gln Trp Glu Tyr Leu Asp Leu Ser Tyr Asp Trp Gln Gly
            260                 265                 270

Thr Asn Leu Thr Ser Trp Gly Asn Arg Ile Val His Gly Pro Asn Gly
        275                 280                 285

Leu Lys Glu Thr Ser Ile Pro Ser Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser
        435                 440                 445

Asn Ser Asn Gly Gln Thr Ala Ile Tyr Leu Asp His Val Thr Ile Gln
    450                 455                 460

<210> SEQ ID NO 17
<211> LENGTH: 1395
<212> TYPE: DNA
<213> ORGANISM: Artificial Sequence
<220> FEATURE:
<223> OTHER INFORMATION: variant

<400> SEQUENCE: 17

```
cagacccact ccggcttcta catcgagggc agcacgctct acgacgctaa cggcgagcct    60
tttgtcatgc gcggcatcaa ccacggccac gcctggtaca agcacgactc caacgtcgcc   120
atccctgcta tcgccaacca gggcgctaac accatccgca tcgtcctcag cgacggtggc   180
cagtgggcca aggacgacat caacacgctg aaccaggtcc tcgacctggc cgaggagcac   240
gagatgatcg ctgtcgtcga ggtccacgac gctaccggca gcaactcgat ggccgacctc   300
aaccgcgccg tcgactactg gatcgagatg aaggacgccc tgatcggcaa ggaagaccgc   360
gtcatcatca acatcgccaa cgagtggtac ggcgcttggg acggccaggg ctgggccaac   420
ggctacaagg aagtcatccc ccgcctgcgc aacgctggct tgacccacac cctcatggtc   480
gacgctgctg gctggggcca gtaccccag agcatccacg actacggcca agaggtcttc    540
aacgccgacc ctctcgccaa caccatgttc agcatccaca tgtacgagta cgctggcggc   600
aacgctgcta tggtccagtc gaacatcgac ggcgtcgtcg accagggcct cgctctggtc   660
atcggcgagt tcggccacat gcacgcggac ggcgacgtcg acgaggctac catcctgtcc   720
tactcgcagc agcgcggcgt cggctggctc gcttggagct ggaagggcaa cggcgctcag   780
tgggagtacc tcgacctgtc gtacgactgg cagggcacca acctcacgtc ctggggcaac   840
accatcgtcc acgccctaa cggcctgaag gagacgtcga tccctagctc gatctttcac    900
accgctccta caacggcga ccctcctccc cacaacggca acgagacgat cctgtacgac    960
ttcgagcacg gcacgcaggg ctggtcgggc tccagcctgc tgggcggccc ttggaccacc  1020
aacgagtgga gcacgaacgg caaccactcg ctcaaggccg acatcttcct gagcgccaac  1080
tcgaagcacg agctcgccaa ggtcgagaac cgcaacctct cgggctactc gacgctgcag  1140
gctaccgtcc gccacgctca ctggggcaac gtcggcaacc tgacggctcg catgtacgtc  1200
aagacgggct cgaactactc ctggttcaac ggcgaccca tccctgtcaa ctcggctaac   1260
ggcaccaccg tcaccctccc tctgagctcc atccccaacc tcaacgacgt caaggagatc  1320
ggcgtcgagt tcatcggcgc tagcaactcg aacggccaga ccgccatcta cctggaccac  1380
gtcacgatcc agtag                                                   1395
```

<210> SEQ ID NO 18
<211> LENGTH: 464
<212> TYPE: PRT
<213> ORGANISM: Artificial Sequence
<220> FEATURE:
<223> OTHER INFORMATION: variant

<400> SEQUENCE: 18

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110
```

Ala Leu Ile Gly Lys Glu Asp Arg Val Ile Ile Asn Ile Ala Asn Glu
            115                 120                 125

Trp Tyr Gly Ala Trp Asp Gly Gln Gly Trp Ala Asn Gly Tyr Lys Glu
130                 135                 140

Val Ile Pro Arg Leu Arg Asn Ala Gly Leu Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ala Met Val Gln Ser Asn
        195                 200                 205

Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Ala Gln Trp Glu Tyr Leu Asp Leu Ser Tyr Asp Trp Gln Gly
            260                 265                 270

Thr Asn Leu Thr Ser Trp Gly Asn Thr Ile Val His Gly Pro Asn Gly
        275                 280                 285

Leu Lys Glu Thr Ser Ile Pro Ser Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser
        435                 440                 445

Asn Ser Asn Gly Gln Thr Ala Ile Tyr Leu Asp His Val Thr Ile Gln
    450                 455                 460

<210> SEQ ID NO 19
<211> LENGTH: 1395
<212> TYPE: DNA
<213> ORGANISM: Artificial Sequence
<220> FEATURE:
<223> OTHER INFORMATION: variant

<400> SEQUENCE: 19
cagacccact ccggcttcta catcgagggc agcacgctct acgacgctaa cggcgagcct      60
tttgtcatgc gcggcatcaa ccacggccac gcctggtaca agcacgactc caacgtcgcc     120

```
atccctgcta tcgccaacca gggcgctaac accatccgca tcgtcctcag cgacggtggc    180
cagtgggcca aggacgacat caacacgctg aaccaggtcc tcgacctggc cgaggagcac    240
gagatgatcg ctgtcgtcga ggtccacgac gctaccggca gcaactcgat ggccgacctc    300
aaccgcgccg tcgactactg gatcgagatg aaggacgccc tgatcggcaa ggaagaccgc    360
gtcatcatca acatcgccaa cgagtggtac ggcgcttggg acggccaggg ctgggccaac    420
ggctacaagg aagtcatccc cgcctgcgc aacgctggct tcacccacac cctcatggtc    480
gacgctgctg gctggggcca gtaccccag agcatccacg actacggcca agaggtcttc    540
aacgccgacc ctctcgccaa caccatgttc agcatccaca tgtacgagta cgctggcggc    600
aacgctgcta tggtccagtc gaacatcgac ggcgtcgtcg accagggcct cgctctggtc    660
atcggcgagt tcggccacat gcacacggac ggcgacgtcg acgaggctac catcctgtcc    720
tactcgcagc agcgcggcgt cggctggctc gcttggagct ggaagggcaa cggcgctcag    780
tgggagtacc tcgacctgtc gtacgactgg cagggcacca acctcacgtc ctggggcaac    840
accatcgtcc acggccctaa cggcctgttg agacgtcga tccctagctc gatctttcac    900
accgctccta caacggcga ccctcctccc cacaacggca acgagacgat cctgtacgac    960
ttcgagcacg gcacgcaggg ctggtcgggc tccagcctgc tgggcggccc ttggaccacc    1020
aacgagtgga gcacgaacgg caaccactcg ctcaaggccg acatcttcct gagcgccaac    1080
tcgaagcacg agctcgccaa ggtcgagaac cgcaacctct cgggctactc gacgctgcag    1140
gctaccgtcc gccacgctca ctggggcaac gtcggcaacc tgacggctcg catgtacgtc    1200
aagacgggct cgaactactc ctggttcaac ggcgacccca tccctgtcaa ctcggctaac    1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                      1395
```

<210> SEQ ID NO 20
<211> LENGTH: 464
<212> TYPE: PRT
<213> ORGANISM: Artificial Sequence
<220> FEATURE:
<223> OTHER INFORMATION: variant

<400> SEQUENCE: 20

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125
```

```
Trp Tyr Gly Ala Trp Asp Gly Gln Gly Trp Ala Asn Gly Tyr Lys Glu
            130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ala Met Val Gln Ser Asn
            195                 200                 205

Ile Asp Gly Val Val Asp Gln Gly Leu Ala Leu Val Ile Gly Glu Phe
210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Ala Gln Trp Glu Tyr Leu Asp Leu Ser Tyr Asp Trp Gln Gly
            260                 265                 270

Thr Asn Leu Thr Ser Trp Gly Asn Thr Ile Val His Gly Pro Asn Gly
            275                 280                 285

Leu Leu Glu Thr Ser Ile Pro Ser Ser Ile Phe His Thr Ala Pro Asn
290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
            355                 360                 365

Glu Asn Arg Asn Leu Ser Gly Tyr Ser Thr Leu Gln Ala Thr Val Arg
370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser
            435                 440                 445

Asn Ser Asn Gly Gln Thr Ala Ile Tyr Leu Asp His Val Thr Ile Gln
450                 455                 460
```

<210> SEQ ID NO 21
<211> LENGTH: 1395
<212> TYPE: DNA
<213> ORGANISM: Artificial Sequence
<220> FEATURE:
<223> OTHER INFORMATION: variant

<400> SEQUENCE: 21
cagacccact cgggcttcta catcgagggc tccacgctct acgacgctaa cggcgagcct        60
tttgtcatgc gcggcatcaa ccacggccac gcctggtaca agcacgacag caacgtcgcc       120
atccctgcta tcgccaacca gggcgctaac accatccgca tcgtcctctc ggacggtggc       180

| | |
|---|---|
| cagtgggcca aggacgacat caacacgctg aaccaggtcc tcgacctggc cgaggagcac | 240 |
| gagatgatcg ctgtcgtcga ggtccacgac gctaccggca gcaactcgat ggccgacctc | 300 |
| aaccgcgccg tcgactactg gatcgagatg aaggacgccc tgatcggcaa ggaagaccgc | 360 |
| gtcatcatca acatcgccaa cgagtggtac ggcgcttggg acggccaggg ctgggccaac | 420 |
| ggctacaagg aagtcatccc ccgcctgcgc aacgctggct caccacac cctcatggtc | 480 |
| gacgctgctg gctggggcca gtaccccag tcgatccacg actacggcca agaggtcttc | 540 |
| aacgccgacc ctctggccaa caccatgttc tcgatccaca tgtacgagta cgctggcggc | 600 |
| aacgctgcta tggtccagtc caacatcgac ggcgtcgtcg accagggcct cgctctggtc | 660 |
| atcggcgagt tcggccacat gcacacggac ggcgacgtcg acgaggctac catcctgtcc | 720 |
| tactcgcagc agcgcggcgt cggctggctc gcttggtcgt ggaagggcaa cggcgctcag | 780 |
| tgggagtacc tcgacctgag ctacgactgg cagggcaccc agctcaccag ctggggcaac | 840 |
| accatcgtcc acggccctaa cggcctcctg gagacgtcca tccctagctc gatctttcac | 900 |
| accgctccta caacggcga ccctcctccc cacaacggcc aggagacgat cctgtacgac | 960 |
| ttcgagcacg gcacgcaggg ctggtcgggc tccagcctgc tgggcggccc ttggaccacc | 1020 |
| aacgagtggt ccacgaacgg caaccacagc ctcaaggccg acatcttcct gagcgccaac | 1080 |
| tcgaagcacg agctcgccaa ggtcgagaac cgcaacctgg ctggctactc gacgctgcag | 1140 |
| gctaccgtcc gccacgctca ctggggcaac gtcggcgctc tgacggctcg catgtacgtc | 1200 |
| aagacgggct ccaactacgc ctggttcaac ggcgacccca tccctgtcaa ctcggctcag | 1260 |
| ggcaccaccg tcaccctccc tctgagctcc atccccaacc tcaacgacgt caaggagatc | 1320 |
| ggcgtcgagt tcatcggcgc tagcaactcg aacggccaga ccgccatcta cctggaccac | 1380 |
| gtcacgatcc agtag | 1395 |

<210> SEQ ID NO 22
<211> LENGTH: 464
<212> TYPE: PRT
<213> ORGANISM: Artificial Sequence
<220> FEATURE:
<223> OTHER INFORMATION: variant

<400> SEQUENCE: 22

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125

Trp Tyr Gly Ala Trp Asp Gly Gln Gly Trp Ala Asn Gly Tyr Lys Glu
    130                 135                 140
```

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
            165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ala Met Val Gln Ser Asn
            195                 200                 205

Ile Asp Gly Val Val Asp Gln Gly Leu Ala Leu Val Ile Gly Glu Phe
            210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
            245                 250                 255

Asn Gly Ala Gln Trp Glu Tyr Leu Asp Leu Ser Tyr Asp Trp Gln Gly
            260                 265                 270

Thr Gln Leu Thr Ser Trp Gly Asn Thr Ile Val His Gly Pro Asn Gly
            275                 280                 285

Leu Leu Glu Thr Ser Ile Pro Ser Ser Ile Phe His Thr Ala Pro Asn
290                 295                 300

Asn Gly Asp Pro Pro His Asn Gly Gln Glu Thr Ile Leu Tyr Asp
305                 310                 315                 320

Phe Glu His Gly Thr Gln Gly Trp Ser Gly Ser Ser Leu Leu Gly Gly
            325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
            355                 360                 365

Glu Asn Arg Asn Leu Ala Gly Tyr Ser Thr Leu Gln Ala Thr Val Arg
370                 375                 380

His Ala His Trp Gly Asn Val Gly Ala Leu Thr Ala Arg Met Tyr Val
385                 390                 395                 400

Lys Thr Gly Ser Asn Tyr Ala Trp Phe Asn Gly Asp Pro Ile Pro Val
            405                 410                 415

Asn Ser Ala Gln Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser
            435                 440                 445

Asn Ser Asn Gly Gln Thr Ala Ile Tyr Leu Asp His Val Thr Ile Gln
            450                 455                 460

<210> SEQ ID NO 23
<211> LENGTH: 1395
<212> TYPE: DNA
<213> ORGANISM: Artificial Sequence
<220> FEATURE:
<223> OTHER INFORMATION: variant

<400> SEQUENCE: 23
cagacccact ccggcttcta catcgagggc agcacgctct acgacgctaa cggcgagcct    60
tttgtcatgc gcggcatcaa ccacggccac gcctggtaca agcacgactc caacgtcgcc    120
atccctgcta tcgccaacca gggcgctaac accatccgca tcgtcctcag cgacggtggc    180
cagtgggcca aggacgacat caacacgctg aaccaggtcc tcgacctggc cgaggagcac    240
gagatgatcg ctgtcgtcga ggtccacgac gctaccggca gcaactcgat ggccgacctc    300

```
aaccgcgccg tcgactactg gatcgagatg aaggacgccc tgatcggcaa ggaagaccgc    360
gtcatcatca acatcgccaa cgagtggtac ggcagctggg acggccaggg ctgggccaac    420
ggctacaagg aagtcatccc ccgcctgcgc aacgctggct tcacccacac cctcatggtc    480
gacgctgctg gctggggcca gtaccccag tcgatccacg actacggcca agaggtcttc     540
aacgccgacc ctctggccaa caccatgttc agcatccaca tgtacgagta cgctggcggc    600
aacgctgcta tggtccagtc gaacatcgac ggcgtcgtcg accagggcct cgctctggtc    660
atcggcgagt tcggccacat gcacacggac ggcgacgtcg acgaggctac catcctgtcc    720
tactcgcaga gcgcggcgt cggctggctc gcttggtcgt ggaagggcaa cggcacgcag      780
tgggagtacc tcgacctgtc gtacgactgg cagggcacca acctcacctc gtggggcaac    840
cgcatcgtcc acgccctaa cggcctcaaa gagacgtcga tccctagctc gatctttcac     900
accgctccta caacggcga ccctcctccc cacaacggca acgagacgat cctgtacgac     960
ttcgagcacg gcacgcaggg ctggtcgggc tccagcctgc tgggcggccc ttggaccacc    1020
aacgagtgga gcaccaacgg caaccactcg ctcaaggccg acatcttcct gagcgccaac    1080
tcgaagcacg agctcgccaa ggtcgagaac cgcaacctct cgggctactc gacgctgcag    1140
gctaccgtcc gccacgctca ctggggcaac gtcggcaacc tgacggctcg catgtacgtc    1200
aagacgggct cgaactactc ctggttcaac ggcgaccca tccctgtcaa ctcggctaac     1260
ggcaccaccg tcaccctccc tctgagctcc atccccaacc tcaacgacgt caaggagatc    1320
ggcgtcgagt tcatcggcgc tagcaactcg aacggccaga ccgccatcta cctggaccac    1380
gtcacgatcc agtag                                                      1395
```

<210> SEQ ID NO 24
<211> LENGTH: 464
<212> TYPE: PRT
<213> ORGANISM: Artificial Sequence
<220> FEATURE:
<223> OTHER INFORMATION: variant

<400> SEQUENCE: 24

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110

Ala Leu Ile Gly Lys Glu Asp Arg Val Ile Asn Ile Ala Asn Glu
        115                 120                 125

Trp Tyr Gly Ser Trp Asp Gly Gln Gly Trp Ala Asn Gly Tyr Lys Glu
    130                 135                 140

Val Ile Pro Arg Leu Arg Asn Ala Gly Phe Thr His Thr Leu Met Val
145                 150                 155                 160
```

Asp Ala Ala Gly Trp Gly Gln Tyr Pro Gln Ser Ile His Asp Tyr Gly
            165                 170                 175

Gln Glu Val Phe Asn Ala Asp Pro Leu Ala Asn Thr Met Phe Ser Ile
        180                 185                 190

His Met Tyr Glu Tyr Ala Gly Gly Asn Ala Ala Met Val Gln Ser Asn
        195                 200                 205

Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Thr Gln Trp Glu Tyr Leu Asp Leu Ser Tyr Asp Trp Gln Gly
            260                 265                 270

Thr Asn Leu Thr Ser Trp Gly Asn Arg Ile Val His Gly Pro Asn Gly
        275                 280                 285

Leu Lys Glu Thr Ser Ile Pro Ser Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser
        435                 440                 445

Asn Ser Asn Gly Gln Thr Ala Ile Tyr Leu Asp His Val Thr Ile Gln
    450                 455                 460

```
<210> SEQ ID NO 25
<211> LENGTH: 1395
<212> TYPE: DNA
<213> ORGANISM: Artificial Sequence
<220> FEATURE:
<223> OTHER INFORMATION: variant

<400> SEQUENCE: 25
cagacccact ccggcttcta catcgagggc agcacgctct acgacgctaa cggcgagcct      60
tttgtcatgc gcggcatcaa ccacggccac gcctggtaca agcacgactc caacgtcgcc     120
atccctgcta tcgccaacca gggcgctaac accatccgca tcgtcctcag cgacggtggc     180
cagtgggcca aggacgacat caacacgctg aaccaggtcc tcgacctggc cgaggagcac     240
gagatgatcg ctgtcgtcga ggtccacgac gctaccggca gcaactcgat ggccgacctc     300
aaccgcgccg tcgactactg gatcgagatg aaggacgccc tgatcggcaa ggaagaccgc     360
```

```
gtcatcatca acatcgccaa cgagtggtac ggcagctggg acggccaggg ctgggccaac    420
ggctacaagg aagtcatccc ccgcctgcgc aacgctggct tcacccacac cctcatggtc    480
gacgctgctg gctggggcca gtaccccag  tcgatccacg actacggcca agaggtcttc     540
aacgccgacc ctctggccaa caccatgttc agcatccaca tgtacgagta cgctggcggc    600
aacgcttcga tggtccagtc gaacatcgac ggcgtcgtcg accagggcct cgctctggtc    660
atcggcgagt cggccacat  gcacacggac ggcgacgtcg acgaggctac catcctgtcc     720
tactcgcagc agcgcggcgt cggctggctc gcttggtcgt ggaagggcaa cggcgctcag    780
tgggagtacc tcgacctgtc gtacgactgg cagggcacca acctcacctc gtggggcaac    840
cgcatcgtcc acggccctaa cggcctcaaa gagacgtcga tccctagctc gatctttcac    900
accgctccta caacggcga  ccctcctccc cacaacggca acgagacgat cctgtacgac    960
ttcgagcacg gcacgcaggg ctggtcgggc tccagcctgc tgggcggccc ttggaccacc   1020
aacgagtgga gcaccaacgg caaccactcg ctcaaggccg acatcttcct gagcgccaac   1080
tcgaagcacg agctcgccaa ggtcgagaac cgcaacctct cgggctactc gacgctgcag   1140
gctaccgtcc gccacgctca ctggggcaac gtcggcaacc tgacggctcg catgtacgtc   1200
aagacgggct cgaactactc ctggttcaac ggcgaccca  tccctgtcaa ctcggctaac   1260
ggcaccaccg tcaccctccc tctgagctcc atccccaacc tcaacgacgt caaggagatc   1320
ggcgtcgagt tcatcggcgc tagcaactcg aacggccaga ccgccatcta cctggaccac   1380
gtcacgatcc agtag                                                    1395
```

<210> SEQ ID NO 26
<211> LENGTH: 464
<212> TYPE: PRT
<213> ORGANISM: Artificial Sequence
<220> FEATURE:
<223> OTHER INFORMATION: variant

<400> SEQUENCE: 26

```
Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125

Trp Tyr Gly Ser Trp Asp Gly Gln Gly Trp Ala Asn Gly Tyr Lys Glu
    130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175
```

Gln Glu Val Phe Asn Ala Asp Pro Leu Ala Asn Thr Met Phe Ser Ile
            180                 185                 190

His Met Tyr Glu Tyr Ala Gly Gly Asn Ala Ser Met Val Gln Ser Asn
        195                 200                 205

Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Ala Gln Trp Glu Tyr Leu Asp Leu Ser Tyr Asp Trp Gln Gly
            260                 265                 270

Thr Asn Leu Thr Ser Trp Gly Asn Arg Ile Val His Gly Pro Asn Gly
        275                 280                 285

Leu Lys Glu Thr Ser Ile Pro Ser Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ile Pro
            420                 425                 430

Asn Leu Asn Asp Val Lys Glu Ile Gly Val Glu Phe Ile Gly Ala Ser
        435                 440                 445

Asn Ser Asn Gly Gln Thr Ala Ile Tyr Leu Asp His Val Thr Ile Gln
    450                 455                 460

<210> SEQ ID NO 27
<211> LENGTH: 1410
<212> TYPE: DNA
<213> ORGANISM: Artificial Sequence
<220> FEATURE:
<223> OTHER INFORMATION: variant

<400> SEQUENCE: 27
tctgatggtc atagccaaac acattctggt ttttatatcg aaggttcaac cctttatgac        60
gccaacggag agccctttgt aatgagaggt atcaatcatg acatgcctg gtataaacat        120 gattctaacg tcgctatacc agctattgct aatcaaggag caaatacaat tcgtattgtt       180
ctgtcagatg gtggtcaatg gcaaaagat gatataaaca cattaaatca gtgctcgat         240 ttagcagagg aacatgagat gattgctgtt gttgaggttc acgatgcaac aggatctaat       300
tctattgctg acttaaatcg tgctgtcgat tattggattg aaatgaaaga cgctttaatt       360
ggaaaagaag atcgcgtcat aattaacatt gccaatgaat ggtatggagc atgggacgga      420
caaggctggg caaatggcta taaggaggtt attccacgtt tacgaaatgc tggcttcact      480

```
catacattaa tggtagatgc agctggttgg ggacaatacc ctcaatcgat tcatgattat      540
ggtcaagagg tatttaatgc tgatccttta gcaaatacga tgttttccat ccatatgtat      600
gaatatgctg gcggaaatgc ttcaatggta caatctaata tcgatggtgt cgtcgatcaa      660
gggttagctc ttgtaatagg agaatttggg catatgcata cggacggaga tgttgatgaa      720
gcaacgatat tgagctactc gcaacaaaga caagtcggtt ggctagcttg gtcttggaaa      780
ggcaatggga ctcaatggga atatctagat ttatcttatg attggcaagg aacaaactta      840
acttcttggg gaaataccat tgtccacggg cctaatggat tactcgaaac atccattcca      900
agctcgattt tccataccgc tccaaacaat ggagatcccc ctcctcataa cggtaatgaa      960
acgatcttat atgatttcga acatggcact caaggctggt caggttcttc acttcttgga     1020
ggaccttgga cgacgaatga atggagtaca aatggtaacc attcattaaa ggccgatatt     1080
ttcttatcag ctaactccaa acatgaatta gcaaaagttg aaaatcgaaa tttatcaggc     1140
tactctactt tacaagccac tgtccgccat gcacattggg gaaatgttgg taatttaacg     1200
gcgagaatgt atgtaaaaac gggctcaaac tatagctggt ttaatggtga tcctatccca     1260
gtaaactcag caaatggtac gactgtcact ttgcctcttt catctattcc aaacctaaat     1320
gacgtaaaag aaattggcgt tgaatttatt ggagcttcaa atagcaatgg acaaaccgcc     1380
atttatttag atcatgtaac aatccaataa                                      1410
```

<210> SEQ ID NO 28
<211> LENGTH: 469
<212> TYPE: PRT
<213> ORGANISM: Artificial Sequence
<220> FEATURE:
<223> OTHER INFORMATION: variant

<400> SEQUENCE: 28

```
Ser Asp Gly His Ser Gln Thr His Ser Gly Phe Tyr Ile Glu Gly Ser
1               5                   10                  15

Thr Leu Tyr Asp Ala Asn Gly Glu Pro Phe Val Met Arg Gly Ile Asn
            20                  25                  30

His Gly His Ala Trp Tyr Lys His Asp Ser Asn Val Ala Ile Pro Ala
        35                  40                  45

Ile Ala Asn Gln Gly Ala Asn Thr Ile Arg Ile Val Leu Ser Asp Gly
    50                  55                  60

Gly Gln Trp Ala Lys Asp Asp Ile Asn Thr Leu Asn Gln Val Leu Asp
65                  70                  75                  80

Leu Ala Glu Glu His Glu Met Ile Ala Val Val Glu Val His Asp Ala
                85                  90                  95

Thr Gly Ser Asn Ser Ile Ala Asp Leu Asn Arg Ala Val Asp Tyr Trp
            100                 105                 110

Ile Glu Met Lys Asp Ala Leu Ile Gly Lys Glu Asp Arg Val Ile Ile
        115                 120                 125

Asn Ile Ala Asn Glu Trp Tyr Gly Ala Trp Asp Gly Gln Gly Trp Ala
    130                 135                 140

Asn Gly Tyr Lys Glu Val Ile Pro Arg Leu Arg Asn Ala Gly Phe Thr
145                 150                 155                 160

His Thr Leu Met Val Asp Ala Ala Gly Trp Gly Gln Tyr Pro Gln Ser
                165                 170                 175

Ile His Asp Tyr Gly Gln Glu Val Phe Asn Ala Asp Pro Leu Ala Asn
            180                 185                 190
```

Thr Met Phe Ser Ile His Met Tyr Glu Tyr Ala Gly Gly Asn Ala Ser
    195                 200                 205

Met Val Gln Ser Asn Ile Asp Gly Val Val Asp Gln Gly Leu Ala Leu
    210                 215                 220

Val Ile Gly Glu Phe Gly His Met His Thr Asp Gly Asp Val Asp Glu
225                 230                 235                 240

Ala Thr Ile Leu Ser Tyr Ser Gln Gln Arg Gln Val Gly Trp Leu Ala
                245                 250                 255

Trp Ser Trp Lys Gly Asn Gly Thr Gln Trp Glu Tyr Leu Asp Leu Ser
            260                 265                 270

Tyr Asp Trp Gln Gly Thr Asn Leu Thr Ser Trp Gly Asn Thr Ile Val
        275                 280                 285

His Gly Pro Asn Gly Leu Leu Glu Thr Ser Ile Pro Ser Ser Ile Phe
    290                 295                 300

His Thr Ala Pro Asn Asn Gly Asp Pro Pro His Asn Gly Asn Glu
305                 310                 315                 320

Thr Ile Leu Tyr Asp Phe Glu His Gly Thr Gln Gly Trp Ser Gly Ser
                325                 330                 335

Ser Leu Leu Gly Gly Pro Trp Thr Thr Asn Glu Trp Ser Thr Asn Gly
            340                 345                 350

Asn His Ser Leu Lys Ala Asp Ile Phe Leu Ser Ala Asn Ser Lys His
        355                 360                 365

Glu Leu Ala Lys Val Glu Asn Arg Asn Leu Ser Gly Tyr Ser Thr Leu
    370                 375                 380

Gln Ala Thr Val Arg His Ala His Trp Gly Asn Val Gly Asn Leu Thr
385                 390                 395                 400

Ala Arg Met Tyr Val Lys Thr Gly Ser Asn Tyr Ser Trp Phe Asn Gly
                405                 410                 415

Asp Pro Ile Pro Val Asn Ser Ala Asn Gly Thr Thr Val Thr Leu Pro
            420                 425                 430

Leu Ser Ser Ile Pro Asn Leu Asn Asp Val Lys Glu Ile Gly Val Glu
        435                 440                 445

Phe Ile Gly Ala Ser Asn Ser Asn Gly Gln Thr Ala Ile Tyr Leu Asp
    450                 455                 460

His Val Thr Ile Gln
465

<210> SEQ ID NO 29
<211> LENGTH: 1410
<212> TYPE: DNA
<213> ORGANISM: Artificial Sequence
<220> FEATURE:
<223> OTHER INFORMATION: variant

<400> SEQUENCE: 29
tctgatggtc atagccaaac acattctggt ttttatatcg aaggttcaac cctttatgac      60
gccaacggag agccctttgt aatgagaggt atcaatcatg acatgcctg gtataaacat     120 gattctaacg tcgctatacc agctattgct aatcaaggag caaatacaat tcgtattgtt     180
ctgtcagatg gtggtcaatg gcaaaagat gatataaaca cattaaatca agtgctcgat     240
ttagcagagg aacatgagat gattgctgtt gttgaggttc acgatgcaac aggatctaat     300
tctatggctg acttaaatcg tgctgtcgat tattggattg aaatgaaaga cgctttaatt     360
ggaaaagaag atcgcgtcat aattaacatt gccaatgaat ggtatggatc atgggacgga     420
caaggctggg caaatggcta taaggaggtt attccacgtt tacgaaatgc tggcttcact     480

```
catacattaa tggtagatgc agctggttgg ggacaatacc ctcaatcgat tcatgattat    540
ggtcaagagg tatttaatgc tgatccttta gcaaatacga tgttttccat ccatatgtat    600
gaatatgctg gcggaaatgc ttcaatggta caatctaata tcgatggtgt cgtcgatcaa    660
gggttagctc ttgtaatagg agaatttggg catatgcata cggacggaga tgttgatgaa    720
gcaacgatat tgagctactc gcaacaaaga ggagtcggtt ggctagcttg gtcttggaaa    780
ggcaatggga ctcaatggga atatctagat ttatcttatg attggcaagg aacaaactta    840
acttcttggg gaaatagaat tgtccacggg cctaatggat tactcgaaac atccattcca    900
agctcgattt tccataccgc tccaaacaat ggagatcccc ctcctcataa cggtaatgaa    960
acgatcttat atgatttcga acatggcact caaggctggt caggttcttc acttcttgga   1020
ggaccttgga cgacgaatga atggagtaca aatggtaacc attcattaaa ggccgatatt   1080
ttcttatcag ctaactccaa acatgaatta gcaaaagttg aaaatcgaaa tttatcaggc   1140
tactctactt tacaagccac tgtccgccat gcacattggg gaaatgttgg taatttaacg   1200
gcgagaatgt atgtaaaaac gggctcaaac tatagctggt ttaatggtga tcctatccca   1260
gtaaactcag caaatggtac gactgtcact ttgcctcttt catctattcc aaacctaaat   1320
gacgtaaaag aaattggcgt tgaatttatt ggagcttcaa atagcaatgg acaaaccgcc   1380
atttatttag atcatgtaac aatccaataa                                    1410
```

<210> SEQ ID NO 30
<211> LENGTH: 469
<212> TYPE: PRT
<213> ORGANISM: Artificial Sequence
<220> FEATURE:
<223> OTHER INFORMATION: variant
<400> SEQUENCE: 30

```
Ser Asp Gly His Ser Gln Thr His Ser Gly Phe Tyr Ile Glu Gly Ser
1               5                   10                  15

Thr Leu Tyr Asp Ala Asn Gly Glu Pro Phe Val Met Arg Gly Ile Asn
            20                  25                  30

His Gly His Ala Trp Tyr Lys His Asp Ser Asn Val Ala Ile Pro Ala
        35                  40                  45

Ile Ala Asn Gln Gly Ala Asn Thr Ile Arg Ile Val Leu Ser Asp Gly
    50                  55                  60

Gly Gln Trp Ala Lys Asp Ile Asn Thr Leu Asn Gln Val Leu Asp
65                  70                  75                  80

Leu Ala Glu Glu His Glu Met Ile Ala Val Val Glu Val His Asp Ala
                85                  90                  95

Thr Gly Ser Asn Ser Met Ala Asp Leu Asn Arg Ala Val Asp Tyr Trp
            100                 105                 110

Ile Glu Met Lys Asp Ala Leu Ile Gly Lys Glu Asp Arg Val Ile Ile
        115                 120                 125

Asn Ile Ala Asn Glu Trp Tyr Gly Ser Trp Asp Gly Gln Gly Trp Ala
    130                 135                 140

Asn Gly Tyr Lys Glu Val Ile Pro Arg Leu Arg Asn Ala Gly Phe Thr
145                 150                 155                 160

His Thr Leu Met Val Asp Ala Ala Gly Trp Gly Gln Tyr Pro Gln Ser
                165                 170                 175

Ile His Asp Tyr Gly Gln Glu Val Phe Asn Ala Asp Pro Leu Ala Asn
            180                 185                 190
```

```
Thr Met Phe Ser Ile His Met Tyr Glu Tyr Ala Gly Gly Asn Ala Ser
        195                 200                 205

Met Val Gln Ser Asn Ile Asp Gly Val Val Asp Gln Gly Leu Ala Leu
    210                 215                 220

Val Ile Gly Glu Phe Gly His Met His Thr Asp Gly Asp Val Asp Glu
225                 230                 235                 240

Ala Thr Ile Leu Ser Tyr Ser Gln Gln Arg Gly Val Gly Trp Leu Ala
                245                 250                 255

Trp Ser Trp Lys Gly Asn Gly Thr Gln Trp Glu Tyr Leu Asp Leu Ser
                260                 265                 270

Tyr Asp Trp Gln Gly Thr Asn Leu Thr Ser Trp Gly Asn Arg Ile Val
                275                 280                 285

His Gly Pro Asn Gly Leu Leu Glu Thr Ser Ile Pro Ser Ser Ile Phe
            290                 295                 300

His Thr Ala Pro Asn Asn Gly Asp Pro Pro His Asn Gly Asn Glu
305                 310                 315                 320

Thr Ile Leu Tyr Asp Phe Glu His Gly Thr Gln Gly Trp Ser Gly Ser
                325                 330                 335

Ser Leu Leu Gly Gly Pro Trp Thr Thr Asn Glu Trp Ser Thr Asn Gly
            340                 345                 350

Asn His Ser Leu Lys Ala Asp Ile Phe Leu Ser Ala Asn Ser Lys His
        355                 360                 365

Glu Leu Ala Lys Val Glu Asn Arg Asn Leu Ser Gly Tyr Ser Thr Leu
        370                 375                 380

Gln Ala Thr Val Arg His Ala His Trp Gly Asn Val Gly Asn Leu Thr
385                 390                 395                 400

Ala Arg Met Tyr Val Lys Thr Gly Ser Asn Tyr Ser Trp Phe Asn Gly
                405                 410                 415

Asp Pro Ile Pro Val Asn Ser Ala Asn Gly Thr Thr Val Thr Leu Pro
                420                 425                 430

Leu Ser Ser Ile Pro Asn Leu Asn Asp Val Lys Glu Ile Gly Val Glu
                435                 440                 445

Phe Ile Gly Ala Ser Asn Ser Asn Gly Gln Thr Ala Ile Tyr Leu Asp
        450                 455                 460

His Val Thr Ile Gln
465

<210> SEQ ID NO 31
<211> LENGTH: 1410
<212> TYPE: DNA
<213> ORGANISM: Artificial Sequence
<220> FEATURE:
<223> OTHER INFORMATION: variant

<400> SEQUENCE: 31
tctgatggtc atagccaaac acattctggt ttttatatcg aaggttcaac cctttatgac      60
gccaacggag agccctttgt aatgagaggt atcaatcatg acatgcctg gtataaacat      120 gattctaacg tcgctatacc agctattgct aatcaaggag caaatacaat tcgtattgtt      180
ctgtcagatg gtggtcaatg gcaaaagat gatataaaca cattaaatca agtgctcgat      240
ttagcagagg aacatgagat gattgctgtt gttgaggttc acgatgcaac aggatctaat      300
tctattgctg acttaaatcg tgctgtcgat tattggattg aaatgaaaga cgctttaatt      360
ggaaaagaag atcgcgtcat aattaacatt gccaatgaat ggtatggatc atgggacgga      420
caaggctggg caaatggcta taaggaggtt attccacgtt tacgaaatgc tggcttcact      480
```

```
catacattaa tggtagatgc agctggttgg ggacaatacc ctcaatcgat tcatgattat    540
ggtcaagagg tatttaatgc tgatccttta gcaaatacga tgttttccat ccatatgtat    600
gaatatgctg gcggaaatgc ttcaatggta caatctaata tcgatggtgt cgtcgatcaa    660
gggttagctc ttgtaatagg agaatttggg catatgcata cggacggaga tgttgatgaa    720
gcaacgatat tgagctactc gcaacaaaga caagtcggtt ggctagcttg gtcttggaaa    780
ggcaatggga ctcaatggga atatctagat ttatcttatg attggcaagg aacaaactta    840
acttcttggg gaaatagaat tgtccacggg cctaatggat tactcgaaac atccattcca    900
agctcgattt tccataccgc tccaaacaat ggagatcccc ctcctcataa cggtaatgaa    960
acgatcttat atgatttcga acatggcact caaggctggt caggttcttc acttcttgga   1020
ggaccttgga cgacgaatga atggagtaca aatggtaacc attcattaaa ggccgatatt   1080
ttcttatcag ctaactccaa acatgaatta gcaaaagttg aaaatcgaaa tttatcaggc   1140
tactctactt tacaagccac tgtccgccat gcacattggg gaaatgttgg taatttaacg   1200
gcgagaatgt atgtaaaaac gggctcaaac tatagctggt ttaatggtga tcctatccca   1260
gtaaactcag caaatggtac gactgtcact ttgcctcttt catctattcc aaacctaaat   1320
gacgtaaaag aaattggcgt tgaatttatt ggagcttcaa atagcaatgg acaaaccgcc   1380
atttatttag atcatgtaac aatccaataa                                     1410
```

<210> SEQ ID NO 32
<211> LENGTH: 469
<212> TYPE: PRT
<213> ORGANISM: Artificial Sequence
<220> FEATURE:
<223> OTHER INFORMATION: variant

<400> SEQUENCE: 32

```
Ser Asp Gly His Ser Gln Thr His Ser Gly Phe Tyr Ile Glu Gly Ser
1               5                   10                  15

Thr Leu Tyr Asp Ala Asn Gly Glu Pro Phe Val Met Arg Gly Ile Asn
            20                  25                  30

His Gly His Ala Trp Tyr Lys His Asp Ser Asn Val Ala Ile Pro Ala
        35                  40                  45

Ile Ala Asn Gln Gly Ala Asn Thr Ile Arg Ile Val Leu Ser Asp Gly
    50                  55                  60

Gly Gln Trp Ala Lys Asp Asp Ile Asn Thr Leu Asn Gln Val Leu Asp
65                  70                  75                  80

Leu Ala Glu Glu His Glu Met Ile Ala Val Val Glu Val His Asp Ala
                85                  90                  95

Thr Gly Ser Asn Ser Ile Ala Asp Leu Asn Arg Ala Val Asp Tyr Trp
            100                 105                 110

Ile Glu Met Lys Asp Ala Leu Ile Gly Lys Glu Asp Arg Val Ile Ile
        115                 120                 125

Asn Ile Ala Asn Glu Trp Tyr Gly Ser Trp Asp Gly Gln Gly Trp Ala
    130                 135                 140

Asn Gly Tyr Lys Glu Val Ile Pro Arg Leu Arg Asn Ala Gly Phe Thr
145                 150                 155                 160

His Thr Leu Met Val Asp Ala Ala Gly Trp Gly Gln Tyr Pro Gln Ser
                165                 170                 175

Ile His Asp Tyr Gly Gln Glu Val Phe Asn Ala Asp Pro Leu Ala Asn
            180                 185                 190
```

```
Thr Met Phe Ser Ile His Met Tyr Glu Tyr Ala Gly Gly Asn Ala Ser
        195                 200                 205

Met Val Gln Ser Asn Ile Asp Gly Val Val Asp Gln Gly Leu Ala Leu
    210                 215                 220

Val Ile Gly Glu Phe Gly His Met His Thr Asp Gly Asp Val Asp Glu
225                 230                 235                 240

Ala Thr Ile Leu Ser Tyr Ser Gln Gln Arg Gln Val Gly Trp Leu Ala
                245                 250                 255

Trp Ser Trp Lys Gly Asn Gly Thr Gln Trp Glu Tyr Leu Asp Leu Ser
            260                 265                 270

Tyr Asp Trp Gln Gly Thr Asn Leu Thr Ser Trp Gly Asn Arg Ile Val
        275                 280                 285

His Gly Pro Asn Gly Leu Leu Glu Thr Ser Ile Pro Ser Ser Ile Phe
    290                 295                 300

His Thr Ala Pro Asn Asn Gly Asp Pro Pro His Asn Gly Asn Glu
305                 310                 315                 320

Thr Ile Leu Tyr Asp Phe Glu His Gly Thr Gln Gly Trp Ser Gly Ser
                325                 330                 335

Ser Leu Leu Gly Gly Pro Trp Thr Thr Asn Glu Trp Ser Thr Asn Gly
            340                 345                 350

Asn His Ser Leu Lys Ala Asp Ile Phe Leu Ser Ala Asn Ser Lys His
        355                 360                 365

Glu Leu Ala Lys Val Glu Asn Arg Asn Leu Ser Gly Tyr Ser Thr Leu
    370                 375                 380

Gln Ala Thr Val Arg His Ala His Trp Gly Asn Val Gly Asn Leu Thr
385                 390                 395                 400

Ala Arg Met Tyr Val Lys Thr Gly Ser Asn Tyr Ser Trp Phe Asn Gly
                405                 410                 415

Asp Pro Ile Pro Val Asn Ser Ala Asn Gly Thr Thr Val Thr Leu Pro
            420                 425                 430

Leu Ser Ser Ile Pro Asn Leu Asn Asp Val Lys Glu Ile Gly Val Glu
        435                 440                 445

Phe Ile Gly Ala Ser Asn Ser Asn Gly Gln Thr Ala Ile Tyr Leu Asp
    450                 455                 460

His Val Thr Ile Gln
465

<210> SEQ ID NO 33
<211> LENGTH: 1410
<212> TYPE: DNA
<213> ORGANISM: Artificial Sequence
<220> FEATURE:
<223> OTHER INFORMATION: variant

<400> SEQUENCE: 33
tctgatggtc atagccaaac acattctggt tttatatcg aaggttcaac cctttatgac      60
gccaacggag agccctttgt aatgagaggt atcaatcatg acatgcctg gtataaacat     120 gattctaacg tcgctatacc agctattgct aatcaaggag caaatacaat tcgtattgtt     180
ctgtcagatg gtggtcaatg gcaaaagat gatataaaca cattaaatca agtgctcgat     240
ttagcagagg aacatgagat gattgctgtt gttgaggttc acgatgcaac aggatctaat     300
tctattgctg acttaaatcg tgctgtcgat tattggattg aaatgaaaga cgctttaatt     360
ggaaaagaag atcgcgtcat aattaacatt gccaatgaat ggtatggagc atgggacgga     420
caaggctggg caaatggcta taaggaggtt attccacgtt tacgaaatgc tggcttcact     480
```

-continued

```
catacattaa tggtagatgc agctggttgg ggacaatacc ctcaatcgat tcatgattat    540
ggtcaagagg tatttaatgc tgatccttta gcaaatacga tgttttccat ccatatgtat    600
gaatatgctg gcggaaatgc ttcaatggta caatctaata tcgatggtgt cgtcgatcaa    660
gggttagctc ttgtaatagg agaatttggg catatgcata cggacggaga tgttgatgaa    720
gcaacgatat tgagctactc gcaacaaaga caagtcggtt ggctagcttg gtcttggaaa    780
ggcaatggga ctcaatggga atatctagat ttatcttatg attggcaagg aacaaactta    840
acttcttggg gaaataccat tgtccacggg cctaatggat taaagaaac atccattcca      900
agctcgattt tccataccgc tccaaacaat ggagatcccc ctcctcataa cggtaatgaa    960
acgatcttat atgatttcga acatggcact caaggctggt caggttcttc acttcttgga   1020
ggaccttgga cgacgaatga atggagtaca aatggtaacc attcattaaa ggccgatatt   1080
ttcttatcag ctaactccaa acatgaatta gcaaaagttg aaaatcgaaa tttatcaggc   1140
tactctactt tacaagccac tgtccgccat gcacattggg gaaatgttgg taatttaacg   1200
gcgagaatgt atgtaaaaac gggctcaaac tatagctggt ttaatggtga tcctatccca   1260
gtaaactcag caaatggtac gactgtcact ttgcctcttt catctattcc aaacctaaat   1320
gacgtaaaag aaattggcgt tgaatttatt ggagcttcaa atagcaatgg acaaaccgcc   1380
atttatttag atcatgtaac aatccaataa                                    1410
```

<210> SEQ ID NO 34
<211> LENGTH: 469
<212> TYPE: PRT
<213> ORGANISM: Artificial Sequence
<220> FEATURE:
<223> OTHER INFORMATION: variant

<400> SEQUENCE: 34

```
Ser Asp Gly His Ser Gln Thr His Ser Gly Phe Tyr Ile Glu Gly Ser
1               5                   10                  15

Thr Leu Tyr Asp Ala Asn Gly Glu Pro Phe Val Met Arg Gly Ile Asn
            20                  25                  30

His Gly His Ala Trp Tyr Lys His Asp Ser Asn Val Ala Ile Pro Ala
        35                  40                  45

Ile Ala Asn Gln Gly Ala Asn Thr Ile Arg Ile Val Leu Ser Asp Gly
    50                  55                  60

Gly Gln Trp Ala Lys Asp Ile Asn Thr Leu Asn Gln Val Leu Asp
65                  70                  75                  80

Leu Ala Glu Glu His Glu Met Ile Ala Val Val Glu Val His Asp Ala
                85                  90                  95

Thr Gly Ser Asn Ser Ile Ala Asp Leu Asn Arg Ala Val Asp Tyr Trp
            100                 105                 110

Ile Glu Met Lys Asp Ala Leu Ile Gly Lys Glu Asp Arg Val Ile Ile
        115                 120                 125

Asn Ile Ala Asn Glu Trp Tyr Gly Ala Trp Asp Gly Gln Gly Trp Ala
    130                 135                 140

Asn Gly Tyr Lys Glu Val Ile Pro Arg Leu Arg Asn Ala Gly Phe Thr
145                 150                 155                 160

His Thr Leu Met Val Asp Ala Ala Gly Trp Gly Gln Tyr Pro Gln Ser
                165                 170                 175

Ile His Asp Tyr Gly Gln Glu Val Phe Asn Ala Asp Pro Leu Ala Asn
            180                 185                 190
```

```
Thr Met Phe Ser Ile His Met Tyr Glu Tyr Ala Gly Gly Asn Ala Ser
        195                 200                 205

Met Val Gln Ser Asn Ile Asp Gly Val Val Asp Gln Gly Leu Ala Leu
    210                 215                 220

Val Ile Gly Glu Phe Gly His Met His Thr Asp Gly Asp Val Asp Glu
225                 230                 235                 240

Ala Thr Ile Leu Ser Tyr Ser Gln Gln Arg Gln Val Gly Trp Leu Ala
                245                 250                 255

Trp Ser Trp Lys Gly Asn Gly Thr Gln Trp Glu Tyr Leu Asp Leu Ser
            260                 265                 270

Tyr Asp Trp Gln Gly Thr Asn Leu Thr Ser Trp Gly Asn Thr Ile Val
        275                 280                 285

His Gly Pro Asn Gly Leu Lys Glu Thr Ser Ile Pro Ser Ser Ile Phe
    290                 295                 300

His Thr Ala Pro Asn Asn Gly Asp Pro Pro His Asn Gly Asn Glu
305                 310                 315                 320

Thr Ile Leu Tyr Asp Phe Glu His Gly Thr Gln Gly Trp Ser Gly Ser
                325                 330                 335

Ser Leu Leu Gly Gly Pro Trp Thr Thr Asn Glu Trp Ser Thr Asn Gly
            340                 345                 350

Asn His Ser Leu Lys Ala Asp Ile Phe Leu Ser Ala Asn Ser Lys His
        355                 360                 365

Glu Leu Ala Lys Val Glu Asn Arg Asn Leu Ser Gly Tyr Ser Thr Leu
    370                 375                 380

Gln Ala Thr Val Arg His Ala His Trp Gly Asn Val Gly Asn Leu Thr
385                 390                 395                 400

Ala Arg Met Tyr Val Lys Thr Gly Ser Asn Tyr Ser Trp Phe Asn Gly
                405                 410                 415

Asp Pro Ile Pro Val Asn Ser Ala Asn Gly Thr Thr Val Thr Leu Pro
            420                 425                 430

Leu Ser Ser Ile Pro Asn Leu Asn Asp Val Lys Glu Ile Gly Val Glu
        435                 440                 445

Phe Ile Gly Ala Ser Asn Ser Asn Gly Gln Thr Ala Ile Tyr Leu Asp
    450                 455                 460

His Val Thr Ile Gln
465

<210> SEQ ID NO 35
<211> LENGTH: 1410
<212> TYPE: DNA
<213> ORGANISM: Artificial Sequence
<220> FEATURE:
<223> OTHER INFORMATION: variant

<400> SEQUENCE: 35
tctgatggtc atagccaaac acattctggt ttttatatcg aaggttcaac cctttatgac      60
gccaacggag agccctttgt aatgagaggt atcaatcatg acatgcctg gtataaacat     120 gattctaacg tcgctatacc agctattgct aatcaaggag caaatacaat tcgtattgtt     180
ctgtcagatg gtggtcaatg gcaaaagat gatataaaca cattaaatca agtgctcgat     240
ttagcagagg aacatgagat gattgctgtt gttgaggttc acgatgcaac aggatctaat     300
tctatggctg acttaaatcg tgctgtcgat tattggattg aaatgaaaga cgctttaatt     360
ggaaaagaag atcgcgtcat aattaacatt gccaatgaat ggtatggatc atgggacgga     420
caaggctggg caaatggcta taaggaggtt attccacgtt tacgaaatgc tggcttcact     480
```

-continued

```
catacattaa tggtagatgc agctggttgg ggacaatacc ctcaatcgat tcatgattat    540
ggtcaagagg tatttaatgc tgatccttta gcaaatacga tgttttccat ccatatgtat    600
gaatatgctg gcggaaatgc ttcaatggta caatctaata tcgatggtgt cgtcgatcaa    660
gggttagctc ttgtaatagg agaatttggg catatgcata cggacggaga tgttgatgaa    720
gcaacgatat tgagctactc gcaacaaaga ggagtcggtt ggctagcttg gtcttggaaa    780
ggcaatggga ctcaatggga atatctagat ttatcttatg attggcaagg aacaaactta    840
acttcttggg gaaatagaat tgtccacggg cctaatggat taaagaaac atccattcca     900
agctcgattt tccataccgc tccaaacaat ggagatcccc ctcctcataa cggtaatgaa    960
acgatcttat atgatttcga acatggcact caaggctggt caggttcttc acttcttgga   1020
ggaccttgga cgacgaatga atggagtaca aatggtaacc attcattaaa ggccgatatt   1080
ttcttatcag ctaactccaa acatgaatta gcaaaagttg aaaatcgaaa tttatcaggc   1140
tactctactt tacaagccac tgtccgccat gcacattggg gaaatgttgg taatttaacg   1200
gcgagaatgt atgtaaaaac gggctcaaac tatagctggt ttaatggtga tcctatccca   1260
gtaaactcag caaatggtac gactgtcact ttgcctcttt catctattcc aaacctaaat   1320
gacgtaaaag aaattggcgt tgaatttatt ggagcttcaa atagcaatgg acaaaccgcc   1380
atttatttag atcatgtaac aatccaataa                                     1410
```

<210> SEQ ID NO 36
<211> LENGTH: 469
<212> TYPE: PRT
<213> ORGANISM: Artificial Sequence
<220> FEATURE:
<223> OTHER INFORMATION: variant

<400> SEQUENCE: 36

```
Ser Asp Gly His Ser Gln Thr His Ser Gly Phe Tyr Ile Glu Gly Ser
1               5                   10                  15

Thr Leu Tyr Asp Ala Asn Gly Glu Pro Phe Val Met Arg Gly Ile Asn
            20                  25                  30

His Gly His Ala Trp Tyr Lys His Asp Ser Asn Val Ala Ile Pro Ala
        35                  40                  45

Ile Ala Asn Gln Gly Ala Asn Thr Ile Arg Ile Val Leu Ser Asp Gly
    50                  55                  60

Gly Gln Trp Ala Lys Asp Ile Asn Thr Leu Asn Gln Val Leu Asp
65                  70                  75                  80

Leu Ala Glu Glu His Glu Met Ile Ala Val Glu Val His Asp Ala
                85                  90                  95

Thr Gly Ser Asn Ser Met Ala Asp Leu Asn Arg Ala Val Asp Tyr Trp
            100                 105                 110

Ile Glu Met Lys Asp Ala Leu Ile Gly Lys Glu Asp Arg Val Ile Ile
        115                 120                 125

Asn Ile Ala Asn Glu Trp Tyr Gly Ser Trp Asp Gly Gln Gly Trp Ala
    130                 135                 140

Asn Gly Tyr Lys Glu Val Ile Pro Arg Leu Arg Asn Ala Gly Phe Thr
145                 150                 155                 160

His Thr Leu Met Val Asp Ala Ala Gly Trp Gly Gln Tyr Pro Gln Ser
                165                 170                 175

Ile His Asp Tyr Gly Gln Glu Val Phe Asn Ala Asp Pro Leu Ala Asn
            180                 185                 190
```

```
Thr Met Phe Ser Ile His Met Tyr Glu Tyr Ala Gly Gly Asn Ala Ser
        195                 200                 205

Met Val Gln Ser Asn Ile Asp Gly Val Val Asp Gln Gly Leu Ala Leu
    210                 215                 220

Val Ile Gly Glu Phe Gly His Met His Thr Asp Gly Asp Val Asp Glu
225                 230                 235                 240

Ala Thr Ile Leu Ser Tyr Ser Gln Gln Arg Gly Val Gly Trp Leu Ala
                245                 250                 255

Trp Ser Trp Lys Gly Asn Gly Thr Gln Trp Glu Tyr Leu Asp Leu Ser
                260                 265                 270

Tyr Asp Trp Gln Gly Thr Asn Leu Thr Ser Trp Gly Asn Arg Ile Val
                275                 280                 285

His Gly Pro Asn Gly Leu Lys Glu Thr Ser Ile Pro Ser Ser Ile Phe
            290                 295                 300

His Thr Ala Pro Asn Asn Gly Asp Pro Pro His Asn Gly Asn Glu
305                 310                 315                 320

Thr Ile Leu Tyr Asp Phe Glu His Gly Thr Gln Gly Trp Ser Gly Ser
                325                 330                 335

Ser Leu Leu Gly Gly Pro Trp Thr Thr Asn Glu Trp Ser Thr Asn Gly
            340                 345                 350

Asn His Ser Leu Lys Ala Asp Ile Phe Leu Ser Ala Asn Ser Lys His
            355                 360                 365

Glu Leu Ala Lys Val Glu Asn Arg Asn Leu Ser Gly Tyr Ser Thr Leu
        370                 375                 380

Gln Ala Thr Val Arg His Ala His Trp Gly Asn Val Gly Asn Leu Thr
385                 390                 395                 400

Ala Arg Met Tyr Val Lys Thr Gly Ser Asn Tyr Ser Trp Phe Asn Gly
                405                 410                 415

Asp Pro Ile Pro Val Asn Ser Ala Asn Gly Thr Thr Val Thr Leu Pro
                420                 425                 430

Leu Ser Ser Ile Pro Asn Leu Asn Asp Val Lys Glu Ile Gly Val Glu
            435                 440                 445

Phe Ile Gly Ala Ser Asn Ser Asn Gly Gln Thr Ala Ile Tyr Leu Asp
450                 455                 460

His Val Thr Ile Gln
465

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
gatgcaacag gatctaattc tattgctgac                                     30

<210> SEQ ID NO 38
<211> LENGTH: 34
<212> TYPE: DNA
<213> ORGANISM: Artificial Sequence
<220> FEATURE:
<223> OTHER INFORMATION: primer

<400> SEQUENCE: 38
gctagccaac cgacttgtct ttgttgcgag tagc                                34
```

```
<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
gatcctgttg catcgtgaac c                                              21

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
gtcggttggc tagcttggtc                                                20

<210> SEQ ID NO 41
<211> LENGTH: 25
<212> TYPE: DNA
<213> ORGANISM: Artificial Sequence
<220> FEATURE:
<223> OTHER INFORMATION: primer

<400> SEQUENCE: 41
atgaatggta tggatcatgg gacgg                                          25

<210> SEQ ID NO 42
<211> LENGTH: 25
<212> TYPE: DNA
<213> ORGANISM: Artificial Sequence
<220> FEATURE:
<223> OTHER INFORMATION: primer

<400> SEQUENCE: 42
ggcccgtgga caattctatt tcccc                                          25

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
tccataccat tcattggcaa tg                                             22

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
attgtccacg ggcctaatgg                                                20

<210> SEQ ID NO 45
<211> LENGTH: 21
<212> TYPE: DNA
<213> ORGANISM: Artificial Sequence
<220> FEATURE:
<223> OTHER INFORMATION: primer
```

```
<400> SEQUENCE: 45
gaaacatcca ttccaagctc g                                         21

<210> SEQ ID NO 46
<211> LENGTH: 31
<212> TYPE: DNA
<213> ORGANISM: Artificial Sequence
<220> FEATURE:
<223> OTHER INFORMATION: primer

<400> SEQUENCE: 46
aatggatgtt tcttttaatc cattaggccc g                              31

<210> SEQ ID NO 47
<211> LENGTH: 36
<212> TYPE: DNA
<213> ORGANISM: Artificial Sequence
<220> FEATURE:
<223> OTHER INFORMATION: primer

<400> SEQUENCE: 47
cggtatatct ctgtcttatt ggattgttac atgatc                         36

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
gacagagata taccgacagt g                                         21
```